(12) United States Patent
Benting et al.

(10) Patent No.: US 9,206,137 B2
(45) Date of Patent: *Dec. 8, 2015

(54) N-ARYL PYRAZOLE(THIO)CARBOXAMIDES

(75) Inventors: Juergen Benting, Leichlingen (DE); Philippe Desbordes, Lyons (FR); Stephanie Gary, Champagne-au-Mont-d'Or (FR); Joerg Greul, Leverkusen (DE); Tomoki Tsuchiya, Lyons (FR); Ulrike Wachendorff-Neumann, Neuwied (DE)

(73) Assignee: BAYER INTELLECTUAL PROPERTY GMBH, Monheim (DE)

( * ) Notice: Subject to any disclaimer, the term of this patent is extended or adjusted under 35 U.S.C. 154(b) by 132 days.

This patent is subject to a terminal disclaimer.

(21) Appl. No.: 13/884,938

(22) PCT Filed: Nov. 14, 2011

(86) PCT No.: PCT/EP2011/070036
§ 371 (c)(1),
(2), (4) Date: May 10, 2013

(87) PCT Pub. No.: WO2012/065944
PCT Pub. Date: May 24, 2012

(65) Prior Publication Data
US 2013/0237500 A1  Sep. 12, 2013

Related U.S. Application Data

(60) Provisional application No. 61/441,028, filed on Feb. 9, 2011.

(30) Foreign Application Priority Data

| Nov. 15, 2010 | (EP) | ..... 10191269 |
| Nov. 15, 2010 | (EP) | ..... 10356031 |
| Nov. 18, 2010 | (EP) | ..... 10191761 |
| Jun. 9, 2011 | (EP) | ..... 11356008 |

(51) Int. Cl.

| C07D 231/16 | (2006.01) |
| C07D 409/12 | (2006.01) |
| A01N 55/00 | (2006.01) |
| C07D 231/14 | (2006.01) |
| A01N 43/56 | (2006.01) |
| C07D 405/12 | (2006.01) |
| C07F 7/08 | (2006.01) |

(52) U.S. Cl.
CPC .............. *C07D 231/16* (2013.01); *A01N 43/56* (2013.01); *A01N 55/00* (2013.01); *C07D 231/14* (2013.01); *C07D 405/12* (2013.01); *C07D 409/12* (2013.01); *C07F 7/0812* (2013.01)

(58) Field of Classification Search
None
See application file for complete search history.

(56) References Cited

U.S. PATENT DOCUMENTS

| 1,794,306 | A | 2/1931 | Liberge |
| 4,761,373 | A | 8/1988 | Anderson et al. |
| 5,013,659 | A | 5/1991 | Bedbrook et al. |
| 5,084,082 | A | 1/1992 | Sebastian et al. |
| 5,141,870 | A | 8/1992 | Bedbrook et al. |
| 5,198,599 | A | 3/1993 | Thill et al. |
| 5,273,894 | A | 12/1993 | Strauch et al. |
| 5,276,268 | A | 1/1994 | Strauch et al. |
| 5,304,732 | A | 4/1994 | Anderson |
| 5,331,107 | A | 7/1994 | Anderson et al. |
| 5,378,824 | A | 1/1995 | Bedbrook et al. |
| 5,434,175 | A | 7/1995 | Babin et al. |
| 5,434,283 | A | 7/1995 | Wong et al. |
| 5,561,236 | A | 10/1996 | Leemans et al. |
| 5,605,011 | A | 2/1997 | Bedbrook et al. |
| 5,637,489 | A | 6/1997 | Strauch et al. |
| 5,646,024 | A | 7/1997 | Leemans et al. |
| 5,648,477 | A | 7/1997 | Leemans et al. |
| 5,712,107 | A | 1/1998 | Nichols et al. |
| 5,731,180 | A | 3/1998 | Dietrich et al. |
| 5,739,082 | A | 4/1998 | Donn et al. |
| 5,767,361 | A | 6/1998 | Dietrich et al. |
| 5,773,702 | A | 6/1998 | Penner et al. |
| 5,776,760 | A | 7/1998 | Barry et al. |
| 5,824,790 | A | 10/1998 | Keeling et al. |
| 5,840,946 | A | 11/1998 | Wong et al. |
| 5,908,810 | A | 6/1999 | Donn et al. |
| 5,908,975 | A | 6/1999 | Caimi et al. |
| 5,928,937 | A | 7/1999 | Kakefuda et al. |
| 5,965,755 | A | 10/1999 | Sernyk et al. |
| 5,969,169 | A | 10/1999 | Fan et al. |
| 6,013,861 | A | 1/2000 | Bird et al. |
| 6,040,497 | A | 3/2000 | Spencer et al. |
| 6,063,947 | A | 5/2000 | DeBonte et al. |

(Continued)

FOREIGN PATENT DOCUMENTS

| CA | 2561992 A1 | 3/2007 |
| CN | 102057925 A | 5/2011 |

(Continued)

OTHER PUBLICATIONS

Patani et al. (Chem. Rev. 1996, 3147-3176).*
Schnepf et al. "Characterization of CRY34/CRY35 Binary Insecticidal Proteins From Diverse Bacillus Thuringiensis Strain Collections", Applied and Environmental Microbiology, Apr. 2005, vol. 71, No. 4, p. 1765-1774.
Barry et al. "Inhibitors of Amino Acid Biosynthesis: Strategies for Imparting Glyphosate Tolerance to Crop Plants", "Current Topics in Plant Physiology", (1992) vol. 7, p. 139-145.

(Continued)

*Primary Examiner* — Kamal Saeed
(74) *Attorney, Agent, or Firm* — Miles & Stockbridge PC

(57) ABSTRACT

The present invention relates to novel (thio)carboxamides, their process of preparation, their use as fungicide active agents, particularly in the form of fungicide compositions, and methods for the control of phytopathogenic fungi, notably of plants, using these compounds or compositions.

20 Claims, No Drawings

(56) References Cited

U.S. PATENT DOCUMENTS

| | | |
|---|---|---|
| 6,169,190 B1 | 1/2001 | Lanuza et al. |
| 6,229,072 B1 | 5/2001 | Burns et al. |
| 6,270,828 B1 | 8/2001 | DeBonte et al. |
| 6,284,479 B1 | 9/2001 | Nichols et al. |
| 6,323,392 B1 | 11/2001 | Charne et al. |
| 6,566,587 B1 | 5/2003 | Lebrun et al. |
| 6,570,066 B1 | 5/2003 | Willmitzer et al. |
| 6,734,341 B2 | 5/2004 | Singletary et al. |
| 6,768,044 B1 | 7/2004 | Boudec et al. |
| 7,112,665 B1 | 9/2006 | Leemans et al. |
| 7,157,281 B2 | 1/2007 | Dizigan et al. |
| 7,435,807 B1 | 10/2008 | Barbour et al. |
| 7,504,561 B2 | 3/2009 | Hammer et al. |
| 7,659,376 B2 | 2/2010 | Hammer et al. |
| 7,692,068 B2 | 4/2010 | Carozzi et al. |
| 7,718,850 B2 | 5/2010 | Vancanneyt et al. |
| 7,803,925 B2 | 9/2010 | Carozzi et al. |
| 7,811,598 B2 | 10/2010 | Carozzi et al. |
| 7,820,708 B2 | 10/2010 | Dunkel et al. |
| 7,842,853 B2 | 11/2010 | Uwer et al. |
| 7,932,283 B2 | 4/2011 | Schwarz et al. |
| 7,960,616 B2 | 6/2011 | Heinrichs et al. |
| 8,097,775 B2 | 1/2012 | Hammer et al. |
| 8,113,101 B1 | 2/2012 | McCants, Jr. |
| 8,147,856 B2 | 4/2012 | Carozzi et al. |
| 8,173,590 B2 | 5/2012 | Carozzi et al. |
| 8,226,966 B2 | 7/2012 | Desbordes et al. |
| 8,309,332 B2 | 11/2012 | Peters et al. |
| 8,314,292 B2 | 11/2012 | Carozzi et al. |
| 8,334,431 B2 | 12/2012 | Sampson et al. |
| 8,450,562 B2 | 5/2013 | De Block et al. |
| 8,461,421 B2 | 6/2013 | Sampson et al. |
| 2002/0031826 A1 | 3/2002 | Nichols et al. |
| 2003/0126634 A1 | 7/2003 | Spencer et al. |
| 2004/0107461 A1 | 6/2004 | Commuri et al. |
| 2004/0117870 A1 | 6/2004 | Weyens |
| 2004/0148666 A1 | 7/2004 | Rangwala et al. |
| 2004/0177399 A1 | 9/2004 | Hammer et al. |
| 2004/0180373 A1 | 9/2004 | Levine |
| 2004/0197916 A1 | 10/2004 | Carozzi et al. |
| 2004/0210964 A1 | 10/2004 | Carozzi et al. |
| 2004/0216186 A1 | 10/2004 | Carozzi et al. |
| 2004/0250317 A1 | 12/2004 | Huber et al. |
| 2005/0049410 A1 | 3/2005 | Carozzi et al. |
| 2005/0208506 A1 | 9/2005 | Zhao et al. |
| 2005/0257283 A1 | 11/2005 | Matringe et al. |
| 2006/0010514 A1 | 1/2006 | Birk et al. |
| 2006/0021094 A1 | 1/2006 | Hammer et al. |
| 2006/0070139 A1 | 3/2006 | Bing et al. |
| 2006/0095986 A1 | 5/2006 | Cavato |
| 2006/0115545 A1 | 6/2006 | Frohberg et al. |
| 2006/0130175 A1 | 6/2006 | Ellis et al. |
| 2006/0150269 A1 | 7/2006 | Hammer et al. |
| 2006/0150270 A1 | 7/2006 | Hammer et al. |
| 2006/0150278 A1 | 7/2006 | Frohberg et al. |
| 2006/0162007 A1 | 7/2006 | Guo et al. |
| 2006/0230473 A1 | 10/2006 | Johnson et al. |
| 2006/0242732 A1 | 10/2006 | Carozzi et al. |
| 2006/0253921 A1 | 11/2006 | Carozzi et al. |
| 2006/0253929 A1 | 11/2006 | Frohberg |
| 2006/0282915 A1 | 12/2006 | Malven et al. |
| 2007/0011777 A1 | 1/2007 | Frohberg |
| 2007/0022496 A1 | 1/2007 | Moor et al. |
| 2007/0056056 A1 | 3/2007 | Behr et al. |
| 2007/0067868 A1 | 3/2007 | Negrotto et al. |
| 2007/0071782 A1 | 3/2007 | Deyn et al. |
| 2007/0136840 A1 | 6/2007 | Peters et al. |
| 2007/0163003 A1 | 7/2007 | Frohberg et al. |
| 2007/0169218 A1 | 7/2007 | Carr et al. |
| 2007/0238646 A1 | 10/2007 | Carozzi et al. |
| 2007/0289031 A1 | 12/2007 | Koziel et al. |
| 2007/0289035 A1 | 12/2007 | Vande Berg et al. |
| 2007/0294787 A1 | 12/2007 | Carozzi et al. |
| 2007/0295251 A1 | 12/2007 | Heinrichs |
| 2007/0300326 A1 | 12/2007 | Peters et al. |
| 2008/0063678 A1 | 3/2008 | Von Deyn et al. |
| 2008/0250533 A1 | 10/2008 | Frohberg |
| 2008/0251225 A1 | 10/2008 | Landschuetze et al. |
| 2008/0276336 A1 | 11/2008 | Frohberg et al. |
| 2008/0289060 A1 | 11/2008 | De Beuckeleer et al. |
| 2009/0013431 A1 | 1/2009 | Van et al. |
| 2009/0018016 A1 | 1/2009 | Duck et al. |
| 2009/0029860 A1 | 1/2009 | Moffatt et al. |
| 2009/0036377 A1 | 2/2009 | Carozzi et al. |
| 2009/0064372 A1 | 3/2009 | Kok-Jacon et al. |
| 2009/0069317 A1 | 3/2009 | Pohlman et al. |
| 2009/0099081 A1 | 4/2009 | Carozzi et al. |
| 2009/0100543 A1 | 4/2009 | Carozzi et al. |
| 2009/0105469 A1 | 4/2009 | Soyka et al. |
| 2009/0123561 A1 | 5/2009 | Gewehr et al. |
| 2009/0124498 A1 | 5/2009 | Von Deyn |
| 2009/0126044 A1 | 5/2009 | Carozzi et al. |
| 2009/0144852 A1 | 6/2009 | Tomso et al. |
| 2009/0151016 A1 | 6/2009 | Frohberg et al. |
| 2009/0151018 A1 | 6/2009 | Hammer et al. |
| 2009/0151021 A1 | 6/2009 | Bots et al. |
| 2009/0176844 A1 | 7/2009 | Dunkel et al. |
| 2009/0193545 A1 | 7/2009 | Watson |
| 2009/0199311 A1 | 8/2009 | Frohberg et al. |
| 2009/0203075 A1 | 8/2009 | Hammer et al. |
| 2009/0241219 A1 | 9/2009 | Hammer et al. |
| 2009/0247551 A1 | 10/2009 | Jeschke et al. |
| 2009/0270605 A1 | 10/2009 | Soyka et al. |
| 2009/0300798 A1 | 12/2009 | Kok-Jacon et al. |
| 2009/0313717 A1 | 12/2009 | Hernandez et al. |
| 2009/0317535 A1 | 12/2009 | Frohberg et al. |
| 2010/0034953 A1 | 2/2010 | Frohberg et al. |
| 2010/0048646 A1 | 2/2010 | Jeschke et al. |
| 2010/0056469 A1 | 3/2010 | Langewald et al. |
| 2010/0235951 A1 | 9/2010 | Van Rie et al. |
| 2010/0240705 A1 | 9/2010 | Jeschke et al. |
| 2010/0256195 A1 | 10/2010 | Fischer et al. |
| 2010/0292461 A1 | 11/2010 | Hoehne et al. |
| 2010/0316786 A1 | 12/2010 | Frohberg et al. |
| 2010/0317058 A1 | 12/2010 | Frohberg et al. |
| 2010/0319081 A1 | 12/2010 | Watson |
| 2011/0030106 A1 | 2/2011 | Laga et al. |
| 2011/0039706 A1 | 2/2011 | Busch et al. |
| 2011/0047646 A1 | 2/2011 | Manzanero |
| 2011/0076345 A1 | 3/2011 | Avila |
| 2011/0093970 A1 | 4/2011 | Arioli et al. |
| 2011/0145944 A1 | 6/2011 | Laga et al. |
| 2011/0190493 A1 | 8/2011 | Bretschneider et al. |
| 2011/0212949 A1 | 9/2011 | Bretschneider et al. |
| 2011/0236950 A1 | 9/2011 | Schouten et al. |
| 2011/0262995 A1 | 10/2011 | Peters et al. |
| 2011/0263488 A1 | 10/2011 | Carozzi et al. |
| 2011/0269195 A1 | 11/2011 | Frohberg et al. |
| 2011/0306499 A1 | 12/2011 | Bretschneider et al. |
| 2012/0023603 A1 | 1/2012 | Laga et al. |
| 2012/0117693 A1 | 5/2012 | De Beuckeleer |
| 2012/0172224 A1 | 7/2012 | Livore et al. |
| 2013/0059300 A1 | 3/2013 | Trolinder et al. |
| 2013/0065761 A1 | 3/2013 | Metzlaff et al. |
| 2013/0117894 A1 | 5/2013 | Frohberg et al. |
| 2013/0123506 A1 | 5/2013 | Jeschke et al. |
| 2013/0283482 A1 | 10/2013 | De Block, et al. |
| 2013/0312138 A1 | 11/2013 | Frohberg et al. |
| 2013/0312141 A1 | 11/2013 | De Block et al. |
| 2013/0316348 A1 | 11/2013 | Trolinder et al. |
| 2014/0026262 A1 | 1/2014 | De Beuckeleer |

FOREIGN PATENT DOCUMENTS

| | | |
|---|---|---|
| EP | 0539588 A1 | 5/1993 |
| EP | 0633956 A1 | 1/1995 |
| EP | 0719338 A1 | 7/1996 |
| EP | 0728213 A1 | 8/1996 |
| EP | 0571427 B1 | 8/2003 |
| EP | 1559320 A1 | 3/2005 |
| EP | 0837944 B1 | 3/2006 |
| EP | 20060773017 | 6/2006 |
| EP | 1999141 B1 | 1/2011 |
| EP | 1999263 B1 | 4/2013 |

(56) References Cited

FOREIGN PATENT DOCUMENTS

| | | | |
|---|---|---|---|
| JP | 2006304779 A | 11/2006 | |
| JP | 2010018586 A | 1/2010 | |
| WO | 8910396 A1 | 11/1989 | |
| WO | 9102069 A1 | 2/1991 | |
| WO | 9205251 A1 | 4/1992 | |
| WO | 93180170 A1 | 9/1993 | |
| WO | 9404693 A2 | 3/1994 | |
| WO | 9409144 A1 | 4/1994 | |
| WO | 9411520 A2 | 5/1994 | |
| WO | 9421795 A1 | 9/1994 | |
| WO | 9423043 A2 | 10/1994 | |
| WO | 9601904 A1 | 1/1995 | |
| WO | 9504826 A1 | 2/1995 | |
| WO | 9509910 A1 | 4/1995 | |
| WO | 9509911 A1 | 4/1995 | |
| WO | 9520669 A2 | 8/1995 | |
| WO | 9526407 A1 | 10/1995 | |
| WO | 9531553 A1 | 11/1995 | |
| WO | 9535026 A1 | 12/1995 | |
| WO | 9615248 A1 | 5/1996 | |
| WO | 9619581 A1 | 6/1996 | |
| WO | 9621023 A1 | 7/1996 | |
| WO | 9627674 A1 | 9/1996 | |
| WO | 9630517 A1 | 10/1996 | |
| WO | 9630529 A1 | 10/1996 | |
| WO | 9633270 A1 | 10/1996 | |
| WO | 9634968 A2 | 11/1996 | |
| WO | 9638567 A2 | 12/1996 | |
| WO | 9711188 A1 | 3/1997 | |
| WO | 9713865 A1 | 4/1997 | |
| WO | 9720936 A1 | 6/1997 | |
| WO | 9726362 A1 | 6/1997 | |
| WO | 9730163 A1 | 8/1997 | |
| WO | 9732985 A1 | 9/1997 | |
| WO | 9741218 A1 | 11/1997 | |
| WO | 9742328 A1 | 11/1997 | |
| WO | 9744472 A1 | 11/1997 | |
| WO | 9745545 A1 | 12/1997 | |
| WO | 9746080 A1 | 12/1997 | |
| WO | 9747806 A1 | 12/1997 | |
| WO | 9747807 A1 | 12/1997 | |
| WO | 9747808 A1 | 12/1997 | |
| WO | 9800549 A1 | 1/1998 | |
| WO | 9812335 A1 | 3/1998 | |
| WO | 9820145 A2 | 5/1998 | |
| WO | 9822604 A1 | 5/1998 | |
| WO | 9827212 A1 | 6/1998 | |
| WO | 9827806 A1 | 7/1998 | |
| WO | 9832326 A2 | 7/1998 | |
| WO | 9839460 A1 | 9/1998 | |
| WO | 9840503 A1 | 9/1998 | |
| WO | 9900502 A1 | 1/1999 | |
| WO | 9912950 A2 | 3/1999 | |
| WO | 9924585 A1 | 5/1999 | |
| WO | 9924586 A1 | 5/1999 | |
| WO | 9924593 A1 | 5/1999 | |
| WO | 9934008 A1 | 7/1999 | |
| WO | 9953072 A1 | 10/1999 | |
| WO | 9957965 A1 | 11/1999 | |
| WO | 9958654 A2 | 11/1999 | |
| WO | 9958688 A2 | 11/1999 | |
| WO | 9958690 A2 | 11/1999 | |
| WO | 9960141 A1 | 11/1999 | |
| WO | 9966050 A1 | 12/1999 | |
| WO | 00/04173 A1 | 1/2000 | |
| WO | 00/08175 A2 | 2/2000 | |
| WO | 00/08184 A1 | 2/2000 | |
| WO | 00/08185 A1 | 2/2000 | |
| WO | 00/11192 A2 | 3/2000 | |
| WO | 00/14249 A1 | 3/2000 | |
| WO | 00/22140 A1 | 4/2000 | |
| WO | 00/47727 A2 | 4/2000 | |
| WO | 00/28052 A2 | 5/2000 | |
| WO | 0063432 | 10/2000 | |
| WO | 00/66746 A1 | 11/2000 | |
| WO | 00/66747 A1 | 11/2000 | |
| WO | 00/73422 A1 | 12/2000 | |
| WO | 0073475 A1 | 12/2000 | |
| WO | 0077229 A2 | 12/2000 | |
| WO | 01/12782 A2 | 2/2001 | |
| WO | 01/12826 A2 | 2/2001 | |
| WO | 01/14569 A2 | 3/2001 | |
| WO | 01/17333 A1 | 3/2001 | |
| WO | 01/19975 A2 | 3/2001 | |
| WO | 01/24615 A1 | 4/2001 | |
| WO | 01/31042 A2 | 5/2001 | |
| WO | 01/41558 A1 | 6/2001 | |
| WO | 01/51627 A2 | 7/2001 | |
| WO | 01/51654 A2 | 7/2001 | |
| WO | 01/65922 A2 | 9/2001 | |
| WO | 01/66704 | 9/2001 | |
| WO | 01/83818 A2 | 11/2001 | |
| WO | 01/98509 A2 | 12/2001 | |
| WO | 0202776 A1 | 1/2002 | |
| WO | 02/12172 A1 | 2/2002 | |
| WO | 02/22836 A2 | 3/2002 | |
| WO | 02/26995 A1 | 4/2002 | |
| WO | 02/34923 A2 | 5/2002 | |
| WO | 02/36782 A2 | 5/2002 | |
| WO | 02/36787 A2 | 5/2002 | |
| WO | 02/36831 A2 | 5/2002 | |
| WO | 02/45485 A1 | 6/2002 | |
| WO | 02/46387 A2 | 6/2002 | |
| WO | 02/059086 A1 | 8/2002 | |
| WO | 02/061043 A2 | 8/2002 | |
| WO | 02059086 A1 | 8/2002 | |
| WO | 02/079410 A2 | 10/2002 | |
| WO | 02/085105 A2 | 10/2002 | |
| WO | 02/099385 A2 | 12/2002 | |
| WO | 02/101059 A2 | 12/2002 | |
| WO | 02096882 A1 | 12/2002 | |
| WO | 03/013226 A2 | 2/2003 | |
| WO | 03/033540 A2 | 4/2003 | |
| WO | 03/033651 A2 | 4/2003 | |
| WO | 03/035617 A2 | 5/2003 | |
| WO | 03/052073 A2 | 6/2003 | |
| WO | 03/071860 A2 | 9/2003 | |
| WO | 03/092360 A2 | 11/2003 | |
| WO | 03/106457 A1 | 12/2003 | |
| WO | 2004/014138 A1 | 2/2004 | |
| WO | 2004/024928 A2 | 3/2004 | |
| WO | 2004/040012 A2 | 5/2004 | |
| WO | 2004/049786 A1 | 6/2004 | |
| WO | 2004/053219 A2 | 6/2004 | |
| WO | 2004/056999 A1 | 7/2004 | |
| WO | 2004/058723 A1 | 7/2004 | |
| WO | 2004056179 A2 | 7/2004 | |
| WO | 2004/072109 A2 | 8/2004 | |
| WO | 2004/072235 A2 | 8/2004 | |
| WO | 2004/074492 A1 | 9/2004 | |
| WO | 2004/078983 A2 | 9/2004 | |
| WO | 2004/090140 A2 | 10/2004 | |
| WO | 2004/099160 A1 | 11/2004 | |
| WO | 2004/101751 A2 | 11/2004 | |
| WO | 2004/106529 A2 | 12/2004 | |
| WO | 2004/113542 A1 | 12/2004 | |
| WO | 2005/000007 A2 | 1/2005 | |
| WO | 2005/002324 A2 | 1/2005 | |
| WO | 2005/002359 A2 | 1/2005 | |
| WO | 2005003362 A2 | 1/2005 | |
| WO | 2005/012515 A2 | 2/2005 | |
| WO | 2005/012529 A2 | 2/2005 | |
| WO | 2005/017157 A1 | 2/2005 | |
| WO | 2005/020673 A1 | 3/2005 | |
| WO | 2005021585 A2 | 3/2005 | |
| WO | 2005/030941 A1 | 4/2005 | |
| WO | 2005/030942 A1 | 4/2005 | |
| WO | 2005/033318 A2 | 4/2005 | |
| WO | 2005/035486 A1 | 4/2005 | |
| WO | 2005/042474 A1 | 5/2005 | |
| WO | 2005/063094 A1 | 7/2005 | |
| WO | 2005/077934 A1 | 8/2005 | |
| WO | 2005070917 A1 | 8/2005 | |
| WO | 2005/085216 A1 | 9/2005 | |

(56) References Cited

FOREIGN PATENT DOCUMENTS

| | | |
|---|---|---|
| WO | 2005090578 A1 | 9/2005 |
| WO | 2005/093093 A2 | 10/2005 |
| WO | 2005/095617 A2 | 10/2005 |
| WO | 2005/095618 A2 | 10/2005 |
| WO | 2005/095619 A1 | 10/2005 |
| WO | 2005/095632 A2 | 10/2005 |
| WO | 2005/103266 A1 | 11/2005 |
| WO | 2005/103270 A2 | 11/2005 |
| WO | 2005/103301 A2 | 11/2005 |
| WO | 2005/123927 A1 | 12/2005 |
| WO | 2006/007373 A2 | 1/2006 |
| WO | 2006/009649 A2 | 1/2006 |
| WO | 2006/015376 A2 | 2/2006 |
| WO | 2006/018319 A1 | 2/2006 |
| WO | 2006/021972 A1 | 3/2006 |
| WO | 2006/024351 A1 | 3/2006 |
| WO | 2006/032538 A1 | 3/2006 |
| WO | 2006/038794 A2 | 4/2006 |
| WO | 2006/043635 A1 | 4/2006 |
| WO | 2006/045633 A1 | 5/2006 |
| WO | 2006/046861 A2 | 5/2006 |
| WO | 2006/055851 A2 | 5/2006 |
| WO | 2006/056433 A2 | 6/2006 |
| WO | 2006/060634 A2 | 6/2006 |
| WO | 2006/063862 A1 | 6/2006 |
| WO | 2006/072603 A2 | 7/2006 |
| WO | 2006/085966 A2 | 8/2006 |
| WO | 2006/089633 A2 | 8/2006 |
| WO | 2006/100288 A2 | 9/2006 |
| WO | 2006/103107 A1 | 10/2006 |
| WO | 2006/108674 A2 | 10/2006 |
| WO | 2006/108675 A2 | 10/2006 |
| WO | 2006/108702 A1 | 10/2006 |
| WO | 2006/125065 A2 | 11/2006 |
| WO | 2006/128568 A2 | 12/2006 |
| WO | 2006/128569 A2 | 12/2006 |
| WO | 2006/128570 A1 | 12/2006 |
| WO | 2006/128571 A2 | 12/2006 |
| WO | 2006/128572 A1 | 12/2006 |
| WO | 2006/128573 A2 | 12/2006 |
| WO | 2006/129204 A2 | 12/2006 |
| WO | 2006/133827 A2 | 12/2006 |
| WO | 2006/135717 A1 | 12/2006 |
| WO | 2006/136351 A2 | 12/2006 |
| WO | WO 2006/131230 * | 12/2006 |
| WO | 2007/006806 A2 | 1/2007 |
| WO | 2007/009823 A1 | 1/2007 |
| WO | 2007006806 A2 | 1/2007 |
| WO | 2007/014290 A2 | 2/2007 |
| WO | 2007/017186 A1 | 2/2007 |
| WO | 2007/024782 A2 | 3/2007 |
| WO | 2007/027777 A2 | 3/2007 |
| WO | 2007/035650 A2 | 3/2007 |
| WO | 2007/039314 A2 | 4/2007 |
| WO | 2007/039315 A1 | 4/2007 |
| WO | 2007/039316 A1 | 4/2007 |
| WO | 2007/040280 A1 | 4/2007 |
| WO | 2007/053015 A2 | 5/2007 |
| WO | 2007/057407 A2 | 5/2007 |
| WO | 2007/068373 A1 | 6/2007 |
| WO | 2007/073167 A1 | 6/2007 |
| WO | 2007068373 A1 | 6/2007 |
| WO | 2007/074405 A2 | 7/2007 |
| WO | 2007/075459 A2 | 7/2007 |
| WO | 2007/076115 A2 | 7/2007 |
| WO | 2007/080126 A2 | 7/2007 |
| WO | 2007/080127 A2 | 7/2007 |
| WO | 2007/091277 A2 | 8/2007 |
| WO | 2007/092704 A2 | 8/2007 |
| WO | 2007/101369 A1 | 9/2007 |
| WO | 2007/103567 A2 | 9/2007 |
| WO | 2007/107302 A2 | 9/2007 |
| WO | 2007/107326 A1 | 9/2007 |
| WO | 2007107326 A1 | 9/2007 |
| WO | 2007/115643 A1 | 10/2007 |
| WO | 2007/115644 A1 | 10/2007 |
| WO | 2007/115646 A1 | 10/2007 |
| WO | 2007113327 A2 | 10/2007 |
| WO | 2007/149134 A1 | 12/2007 |
| WO | 2008/002480 A2 | 1/2008 |
| WO | 2008/009360 A2 | 1/2008 |
| WO | 2008/013622 A2 | 1/2008 |
| WO | 2008/054747 A2 | 5/2008 |
| WO | 2008/056915 A1 | 5/2008 |
| WO | 2008/066153 A1 | 6/2008 |
| WO | 2008/067043 A2 | 6/2008 |
| WO | 2008/067911 A1 | 6/2008 |
| WO | 2008/095972 A1 | 8/2008 |
| WO | 2008/104503 A1 | 9/2008 |
| WO | 2008/112019 A2 | 9/2008 |
| WO | 2008/114282 A2 | 9/2008 |
| WO | 2008/122406 A1 | 10/2008 |
| WO | 2008/139334 A2 | 11/2008 |
| WO | 2008/148570 A1 | 12/2008 |
| WO | 2008/150473 A2 | 12/2008 |
| WO | 2009007091 A2 | 1/2009 |
| WO | 2009/016221 A1 | 2/2009 |
| WO | 2009/049110 A1 | 4/2009 |
| WO | 2009/049851 A1 | 4/2009 |
| WO | 2009/068313 A2 | 6/2009 |
| WO | 2009/094442 A2 | 7/2009 |
| WO | 2009/111263 A1 | 9/2009 |
| WO | 2009/144079 A1 | 12/2009 |
| WO | 2009143995 A1 | 12/2009 |
| WO | 2010/005692 A2 | 1/2010 |
| WO | 2010/006713 A2 | 1/2010 |
| WO | 2010/006732 A2 | 1/2010 |
| WO | 2010/019838 A2 | 2/2010 |
| WO | 2010/025451 A2 | 3/2010 |
| WO | 2010/049233 A1 | 5/2010 |
| WO | 2010/069502 A2 | 6/2010 |
| WO | 2010/074747 A1 | 7/2010 |
| WO | 2010074751 A1 | 7/2010 |

OTHER PUBLICATIONS

Gasser et al. "Structure, Expression, and Evolution of the 5-Enolpyruvylshikimate-3-Phosphate Synthase Genes of Petunia and Tomato", The Journal of Bio. Chem., vol. 263, No. 9, Mar. 1988, pp. 4280-4289.
Ley et al. "A Polymer-Supported Thionating Reagent", J. Chem. Soc., Perkin Trans., vol. 1 (2001), pp. 358-361.
Moellenbeck et al. "Insecticidal Proteins From Bacillus Thuringiensis Protect Corn From Corn Rootworms", Nature Biotechnology, vol. 19, Jul. 2001, pp. 668.
"An Altered Aroa Gene Product Confers Resistance to the Herbicide Glyphosate", Science, vol. 221, Jul. 22, 1983, pp. 370-371.
Shah et al. "Engineering Herbicide Tolerance in Transgenic Plants", Science, vol. 233, Jul. 25, 1986, pp. 478-481.
Tranel et al. "Resistance of Weeds to ALS-Inhibiting Herbicides: What Have We Learned?", Weed Science, vol. 50 (2002), pp. 700-712.
E-Mail From Stefan Hillebrand Dated Jul. 7, 2013, http://gmoinfo.jrc.ec.europa.eu.
E-Mail From Joerg Greul, http://www.aphis.usda/gov/biotechnology/brs_main.shtml.
"Biotechnology Regulatory Services", USDA, http://www.aphis.usda.gov/biotechnology/brs_main.shtml.
"The VIP Nomenclature", http://www.lifesci.sussex.ac.uk/home/neil_crickmore/bt/vip.html, VIP Proteins, Jul. 23, 2013.
Europen Search Report of EP 10 35 6031 Dated Mar. 1, 2011.
International Search Report for PCT/EP2011/070036 Mailed Feb. 1, 2012.

* cited by examiner

N-ARYL PYRAZOLE(THIO)CARBOXAMIDES

CROSS REFERENCE TO RELATED APPLICATIONS

This application is a §371 National Stage Application of PCT/EP2011/070036, filed Nov. 14, 2011, which claims priority to European Application No. 10191269.9; filed Nov. 15, 2010; European Application No. 10356031.4, filed Nov. 15, 2010; European Application No. 10191761.5, filed Nov. 18, 2010; U.S. Provisional Application No. 61/441,028, filed Feb. 9, 2011; and European Application No. 11356008.0, filed Jun. 9, 2011.

BACKGROUND OF THE INVENTION

1. Field of the Invention

The present invention relates to novel (thio)carboxamides, their process of preparation, their use as fungicide active agents, particularly in the form of fungicide compositions, and methods for the control of phytopathogenic fungi, notably of plants, using these compounds or compositions.

2. Description of Related Art

In international patent applications WO2007-068373 certain fungicidal (thio)carboxamide derivatives are generically embraced in a broad disclosure of numerous compounds of the following formula:

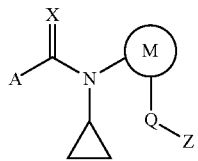

wherein A represents a substituted phenyl or (5 or 6)-membered heterocyclic group that can represent various rings among which a pyrazole ring, M represents monosubstituted phenyl, thiophene, pyridine, pyrimidine, pyridazine, or thiazol ring, Q and Z represents numerous organic residues. However, there is no explicite disclosure or suggestion to select in these documents of any such derivative wherein A represent a 1-methyl-3-(difluoro or dichloro)methyl-5-(chloro or fluoro)-4-pyrazolyl group.

It is always of high-interest in the field of agrochemicals to use pesticidal compounds more active than the compounds already known by the man ordinary skilled in the art whereby reduced amounts of compound can be used whilst retaining equivalent efficacy.

Furthermore, the provision of new pesticidal compounds with a higher efficacy strongly reduces the risk of appearance of resistant strains in the fungi to be treated.

We have now found a new family of compounds which show enhanced fungicidal activity over the general known family of such compounds.

SUMMARY

Thus this invention now provides novel (thio)carboxamides of the formula (I)

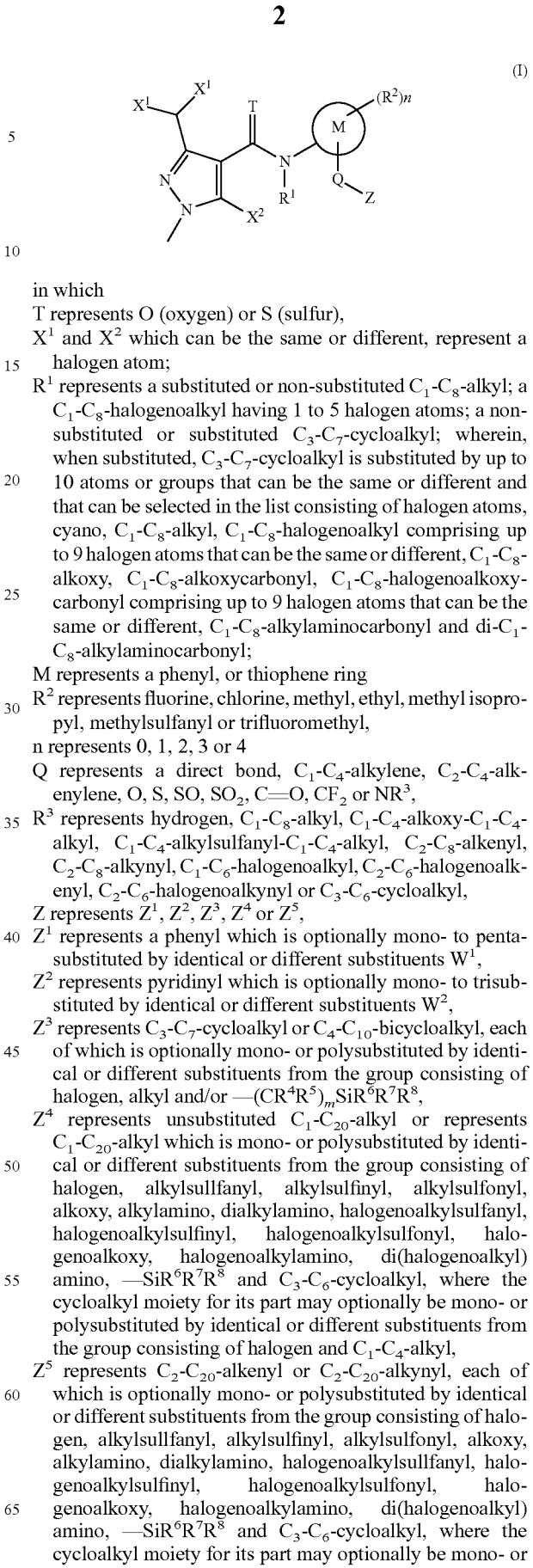

in which

T represents O (oxygen) or S (sulfur), $X^1$ and $X^2$ which can be the same or different, represent a halogen atom;

$R^1$ represents a substituted or non-substituted $C_1$-$C_8$-alkyl; a $C_1$-$C_8$-halogenoalkyl having 1 to 5 halogen atoms; a non-substituted or substituted $C_3$-$C_7$-cycloalkyl; wherein, when substituted, $C_3$-$C_7$-cycloalkyl is substituted by up to 10 atoms or groups that can be the same or different and that can be selected in the list consisting of halogen atoms, cyano, $C_1$-$C_8$-alkyl, $C_1$-$C_8$-halogenoalkyl comprising up to 9 halogen atoms that can be the same or different, $C_1$-$C_8$-alkoxy, $C_1$-$C_8$-alkoxycarbonyl, $C_1$-$C_8$-halogenoalkoxycarbonyl comprising up to 9 halogen atoms that can be the same or different, $C_1$-$C_8$-alkylaminocarbonyl and di-$C_1$-$C_8$-alkylaminocarbonyl;

M represents a phenyl, or thiophene ring $R^2$ represents fluorine, chlorine, methyl, ethyl, methyl isopropyl, methylsulfanyl or trifluoromethyl, n represents 0, 1, 2, 3 or 4

Q represents a direct bond, $C_1$-$C_4$-alkylene, $C_2$-$C_4$-alkenylene, O, S, SO, $SO_2$, C=O, $CF_2$ or $NR^3$, $R^3$ represents hydrogen, $C_1$-$C_8$-alkyl, $C_1$-$C_4$-alkoxy-$C_1$-$C_4$-alkyl, $C_1$-$C_4$-alkylsulfanyl-$C_1$-$C_4$-alkyl, $C_2$-$C_8$-alkenyl, $C_2$-$C_8$-alkynyl, $C_1$-$C_6$-halogenoalkyl, $C_2$-$C_6$-halogenoalkenyl, $C_2$-$C_6$-halogenoalkynyl or $C_3$-$C_6$-cycloalkyl, Z represents $Z^1$, $Z^2$, $Z^3$, $Z^4$ or $Z^5$, $Z^1$ represents a phenyl which is optionally mono- to pentasubstituted by identical or different substituents $W^1$, $Z^2$ represents pyridinyl which is optionally mono- to trisubstituted by identical or different substituents $W^2$, $Z^3$ represents $C_3$-$C_7$-cycloalkyl or $C_4$-$C_{10}$-bicycloalkyl, each of which is optionally mono- or polysubstituted by identical or different substituents from the group consisting of halogen, alkyl and/or —$(CR^4R^5)_m SiR^6R^7R^8$, $Z^4$ represents unsubstituted $C_1$-$C_{20}$-alkyl or represents $C_1$-$C_{20}$-alkyl which is mono- or polysubstituted by identical or different substituents from the group consisting of halogen, alkylsulfanyl, alkylsulfinyl, alkylsulfonyl, alkoxy, alkylamino, dialkylamino, halogenoalkylsulfanyl, halogenoalkylsulfinyl, halogenoalkylsulfonyl, halogenoalkoxy, halogenoalkylamino, di(halogenoalkyl)amino, —$SiR^6R^7R^8$ and $C_3$-$C_6$-cycloalkyl, where the cycloalkyl moiety for its part may optionally be mono- or polysubstituted by identical or different substituents from the group consisting of halogen and $C_1$-$C_4$-alkyl, $Z^5$ represents $C_2$-$C_{20}$-alkenyl or $C_2$-$C_{20}$-alkynyl, each of which is optionally mono- or polysubstituted by identical or different substituents from the group consisting of halogen, alkylsulfanyl, alkylsulfinyl, alkylsulfonyl, alkoxy, alkylamino, dialkylamino, halogenoalkylsulfanyl, halogenoalkylsulfinyl, halogenoalkylsulfonyl, halogenoalkoxy, halogenoalkylamino, di(halogenoalkyl)amino, —$SiR^6R^7R^8$ and $C_3$-$C_6$-cycloalkyl, where the cycloalkyl moiety for its part may optionally be mono- or polysubstituted by identical or different substituents from the group consisting of halogen and $C_1$-$C_4$-alkyl, $R^4$ represents hydrogen or $C_1$-$C_4$-alkyl, $R^5$ represents hydrogen or $C_1$-$C_4$-alkyl, m represents 0, 1, 2 or 3, $R^6$ and $R^7$ independently of one another represent hydrogen, $C_1$-$C_8$-alkyl, $C_1$-$C_8$-alkoxy, $C_1$-$C_4$-alkoxy-$C_1$-$C_4$-alkyl, $C_1$-$C_4$-alkylsulfanyl-$C_1$-$C_4$-alkyl or $C_1$-$C_6$-halogenoalkyl, $R^8$ represents hydrogen, $C_1$-$C_8$-alkyl, $C_1$-$C_8$-alkoxy, $C_1$-$C_4$-alkoxy-$C_1$-$C_4$-alkyl, $C_1$-$C_4$-alkylsulfanyl-$C_1$-$C_4$-alkyl, $C_2$-$C_8$-alkenyl, $C_2$-$C_8$-alkynyl, $C_1$-$C_6$-halogenoalkyl, $C_2$-$C_6$-halogenoalkenyl, $C_2$-$C_6$-halogenoalkynyl, $C_3$-$C_6$-cycloalkyl, or represents in each case optionally substituted phenyl or phenylalkyl;

$W^1$ represents halogen, cyano, nitro, amino, hydroxyl, formyl, carboxy, carbamoyl, thiocarbamoyl; or straight-chain or branched alkyl, hydroxyalkyl, oxoalkyl, alkoxy, alkoxyalkyl, alkylsulfanylalkyl, dialkoxyalkyl, alkylsulfanyl, alkylsulfinyl or alkylsulfonyl having in each case 1 to 8 carbon atoms; or straight-chain or branched alkenyl or alkenyloxy having in each case 2 to 6 carbon atoms; or straight-chain or branched halogenoalkyl, halogenoalkoxy, halogenoalkylsulfanyl, halogenoalkylsulfinyl or halogenoalkylsulfonyl having in each case 1 to 6 carbon atoms and 1 to 13 identical or different halogen atoms; or straight-chain or branched halogenoalkenyl or halogenoalkenyloxy having in each case 2 to 6 carbon atoms and 1 to 11 identical or different halogen atoms; or straight-chain or branched alkylamino, dialkylamino, alkylcarbonyl, alkylcarbonyloxy, alkoxycarbonyl, alkylaminocarbonyl, dialkylaminocarbonyl, arylalkylaminocarbonyl, or dialkylaminocarbonyloxy having 1 to 6 carbon atoms in the respective hydrocarbon chains, or alkenylcarbonyl or alkynylcarbonyl, having 2 to 6 carbon atoms in the respective hydrocarbon chains; or cycloalkyl or cycloalkyloxy having in each case 3 to 6 carbon atoms; or doubly attached alkylene having 3 or 4 carbon atoms, oxyalkylene having 2 or 3 carbon atoms or dioxyalkylene having 1 or 2 carbon atoms, each of which radicals is optionally mono- to tetrasubstituted by identical or different substituents from the group consisting of fluorine, chlorine, oxo, methyl, trifluoromethyl and ethyl;

or the groupings $-(CR^4R^5)_m SiR^6R^7R^8$ or $-C(Q^2)=N-Q^3$, in which $Q^2$ represents hydrogen, hydroxyl or alkyl having 1 to 4 carbon atoms, halogenoalkyl having 1 to 4 carbon atoms and 1 to 9 fluorine, chlorine and/or bromine atoms or cycloalkyl having 1 to 6 carbon atoms and $Q^3$ represents hydroxyl, amino, methylamino, phenyl, benzyl or represents in each case optionally cyano-, hydroxyl-, alkoxy-, alkylsulfanyl-, alkylamino-, dialkylamino- or phenyl-substituted alkyl or alkoxy having 1 to 4 carbon atoms, or represents alkenyloxy or alkynyloxy having in each case 2 to 4 carbon atoms, and also phenyl, phenoxy, phenylsulfanyl, benzoyl, benzoylethenyl, cinnamoyl, heterocyclyl or phenylalkyl, phenylalkyloxy, phenylalkylsulfanyl or heterocyclylalkyl having in each case 1 to 3 carbon atoms in the respective alkyl moieties, each of which radicals is optionally mono- to trisubstituted in the ring moiety by halogen and/or straight-chain or branched alkyl or alkoxy having 1 to 4 carbon atoms;

$W^2$ represents hydrogen, halogen, cyano, nitro, $C_1$-$C_6$-alkyl, $C_2$-$C_4$-alkenyl, $C_2$-$C_4$-alkynyl, $C_1$-$C_4$-alkoxy, $C_1$-$C_4$-alkylsulfanyl, $C_1$-$C_4$-alkylsulfinyl, $C_1$-$C_4$-alkylsulfonyl, $C_3$-$C_6$-cycloalkyl; represents $C_1$-$C_4$-halogenoalkyl, $C_1$-$C_4$-halogenoalkoxy, $C_1$-$C_4$-halogenoalkylsulfanyl, $C_1$-$C_4$-halogenoalkylsulfinyl, $C_1$-$C_4$-halogenoalkylsulfonyl having in each case 1 to 5 halogen atoms; represents $-SO_2NR^{10}R^{11}$, $-C(=Y)R^{12}$, $-Si(R^{13})_3$, $C_2$-$C_4$-alkenylene-$Si(R^{13})_3$, $C_2$-$C_4$-alkynylene-$Si(R^{13})_3$, $-NR^{15}R^{16}$, $CH_2-NR^{15}R^{16}$, in which Y represents O (oxygen) or S (sulfur), $R^{10}$ represents hydrogen, $C_1$-$C_4$-alkyl or $-C(=Y)R^{12}$, $R^{11}$ represents hydrogen, $C_1$-$C_4$-alkyl or $-C(=Y)R^{12}$, or $R^{10}$ and $R^{11}$ together with the nitrogen atom to which they are attached form a saturated heterocycle which has 5 to 8 ring atoms and is optionally mono- or polysubstituted by identical or different substituents from the group consisting of halogen and $C_1$-$C_4$-alkyl, where the heterocycle may contain 1 or 2 further non-adjacent heteroatoms from the group consisting of oxygen, sulfur and $NR^{14}$, $R^{12}$ represents hydrogen, $C_1$-$C_4$-alkyl, $C_1$-$C_4$-alkoxy or $-NR^{15}R^{16}$, $R^{13}$ represents hydrogen, $C_1$-$C_8$-alkyl, $C_1$-$C_8$-alkoxy, $C_1$-$C_4$-alkoxy-$C_1$-$C_4$-alkyl, $C_1$-$C_4$-alkylsulfanyl-$C_1$-$C_4$-alkyl or $C_1$-$C_6$-halogenoalkyl, where the three radicals $R^{13}$ may in each case be identical or different, $R^{14}$ represents hydrogen or $C_1$-$C_6$-alkyl, $R^{15}$ represents hydrogen or $C_1$-$C_4$-alkyl, $R^{16}$ represents hydrogen or $C_1$-$C_4$-alkyl, or $R^{15}$ and $R^{16}$ together with the nitrogen atom to which they are attached form a saturated heterocycle having 5 to 8 ring atoms which is optionally mono- or polysubstituted by identical or different substituents from the group consisting of halogen and $C_1$-$C_4$-alkyl, where the heterocycle may contain 1 or 2 further non-adjacent heteroatoms from the group consisting of oxygen, sulfur and $NR^{14}$, where, unless indicated otherwise, a group or a substituent which is substituted according to the invention is substituted by one or more group selected in the list consisting of halogen; nitro, cyano, $C_1$-$C_{12}$-alkyl; $C_1$-$C_6$-haloalkyl having 1 to 9 identical or different halogen atoms; $C_1$-$C_6$-alkoxy; $C_1$-$C_6$-haloalkoxy having 1 to 9 identical or different halogen atoms; $C_1$-$C_6$-alkylsulfanyl; $C_1$-$C_6$-haloalkylsulfanyl having 1 to 9 identical or different halogen atoms; $C_1$-$C_6$-alkylsulfonyl; $C_1$-$C_6$-haloalkylsulfonyl having 1 to 9 identical or different halogen atoms; $C_2$-$C_{12}$-alkenyl; $C_2$-$C_{12}$-alkynyl; $C_3$-$C_7$-cycloalkyl; phenyl; tri($C_1$-$C_8$)alkylsilyl; tri($C_1$-$C_8$)alkylsilyl-$C_1$-$C_8$-alkyl;

DETAILED DESCRIPTION OF A PREFERRED EMBODIMENT

Finally, it has been found that the novel (thio)carboxamides of the formula (I) have very good microbicidal properties and can be used for controlling unwanted microorganisms both in crop protection and in the protection of materials.

If appropriate, the compounds according to the invention can be present as mixtures of different possible isomeric forms, in particular of stereoisomers, such as, for example, E and Z, threo and erythro, and also optical isomers, and, if appropriate, also of tautomers. What is claimed are both the E and the Z isomers, and also the threo and erythro, and the optical isomers, any mixtures of these isomers, and the possible tautomeric forms.

The formula (I) provides a general definition of the (thio) carboxamides according to the invention. Preferred radical definitions of the formula mentioned above and below are given below. These definitions apply to the end products of the formula (I) and likewise all intermediates.

T preferably represents O (oxygen).
T also preferably represents S (sulfur).
$X^1$ preferably represents fluorine or chlorine.
$X^1$ particularly preferably represents fluorine.
$X^2$ preferably represents fluorine or chlorine.
$X^2$ particularly preferably represents fluorine.
$R^1$ preferably represents a substituted or non-substituted $C_1$-$C_8$-alkyl, a $C_1$-$C_8$-halogenoalkyl having 1 to 5 halogen atoms or a non-substituted $C_3$-$C_7$-cycloalkyl.
$R^1$ particularly preferably represents a substituted or non-substituted $C_1$-$C_6$-alkyl, a $C_1$-$C_6$-halogenoalkyl or a non-substituted $C_3$-$C_7$-cycloalkyl.
$R^1$ more particularly preferably represents methyl, or cyclopropyl.
M preferably represents one of the cycles below:

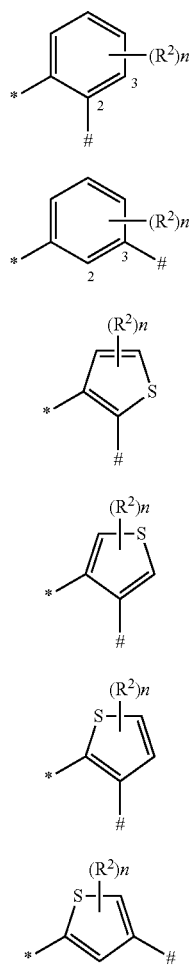

where the bond marked * is linked to the amide and the bond marked # is linked to the radical Q-Z and n is 0 or 1.
M particularly preferably represents M-1.
M furthermore particularly preferably represents the heterocycle M-3.
n preferably represents 0 or 1
$R^2$ preferably represents fluorine.
Q preferably represents a direct bond.
Q furthermore preferably represents O (oxygen).
$R^3$ preferably represents hydrogen, $C_1$-$C_6$-alkyl, $C_1$-$C_3$-alkoxy-$C_1$-$C_3$-alkyl, $C_1$-$C_3$-alkylsulfanyl-$C_1$-$C_3$-alkyl or $C_3$-$C_6$-cycloalkyl.

Z preferably represents $Z^1$.
$Z^1$ preferably represents phenyl which is optionally mono- to pentasubstituted by identical or different substituents, where the substituents are in each case selected from the list $W^1$.
$Z^1$ particularly preferably represents monosubstituted phenyl, where the substituents are selected from the list $W^1$.
$Z^1$ also particularly preferably represents phenyl which is disubstituted by identical or different substituents, where the substituents are selected from the list $W^1$.
$Z^1$ also particularly preferably represents phenyl which is trisubstituted by identical or different substituents, where the substituents are selected from the list $W^1$.
$W^1$ preferably represents fluorine, chlorine, bromine, methyl, ethyl, n- or i-propyl, n-, s- or t-butyl, methoxy, ethoxy, n- or i-propoxy, trifluoromethyl, trifluoroethyl, difluoromethoxy, trifluoromethoxy, difluorochloromethoxy, trifluoroethoxy, in each case doubly attached difluoromethylenedioxy or tetrafluoroethylenedioxy,
or the groupings —$CH_2Si(CH_3)_3$, —$Si(CH_3)_3$ or —$C(Q^2)$=N-$Q^3$, in which
$Q^2$ represents hydrogen, methyl, ethyl or trifluoromethyl and
$Q^3$ represents hydroxyl, methoxy, ethoxy, propoxy or isopropoxy.
Z furthermore, preferably represents $Z^2$.
$Z^2$ preferably represents 2-pyridinyl, 3-pyridinyl or 4-pyridinyl, each of which is optionally mono- to trisubstituted by identical or different substituents, where the substituents are in each case selected from the list $W^2$.
$W^2$ preferably represents hydrogen, fluorine, chlorine, bromine, cyano, nitro, methyl, ethyl, n- or isopropyl, n-, iso-, sec- or tert-butyl, allyl, propargyl, methoxy, ethoxy, n- or isopropoxy, n-, iso-, sec- or tert-butoxy, methylsulfanyl, ethysulfanyl, n- or isopropylsulfanyl, n-, iso-, sec- or tert-butylsulfanyl, methylsulfinyl, ethylsulfinyl, n- or isopropylsulfinyl, n-, iso-, sec- or tert-butylsulfinyl, methylsulfonyl, ethylsulfonyl, n- or iso-propylsulfonyl, n-, iso-, sec- or tert-butylsulfonyl, cyclopropyl, cyclopentyl, cyclohexyl, trifluoromethyl, difluoromethyl, trichloromethyl, trifluoroethyl, trifluoromethoxy, difluoromethoxy, trichloromethoxy, difluoromethylsulfanyl, difluorochloromethylsulfanyl, trifluoromethylsulfanyl, trifluoromethylsulfinyl, trifluoromethylsulfonyl, —$SO_2NMe_2$, —$C(=Y)R^{12}$, —$Si(R^{13})_3$, —CH=CH—Si$(R^{13})_3$, —$CH_2$—CH=CH—Si$(R^{13})_3$, —CH=CH—$CH_2$—Si$(R^{13})_3$, —C≡C—Si$(R^{13})_3$, —$CH_2$—C≡C—Si$(R^{13})_3$, —C≡C—$CH_2$—,
where Y represents O (oxygen) or S (sulfur),
Z furthermore, preferably represents $Z^3$.
$Z^3$ preferably represents $C_3$-$C_7$-cycloalkyl or $C_4$-$C_{10}$ bicycloalkyl having in each case 3 to 10 carbon atoms, each of which radicals is optionally mono- to tetrasubstituted by identical or different substituents from the group consisting of halogen, $C_1$-$C_4$-alkyl, —$CH_2Si(CH_3)_3$ and —Si$(CH_3)_3$.
$Z^3$ very particularly preferably represents chlorine- and methyl-substituted cyclopropyl.
Z furthermore, preferably represents $Z^4$.
$Z^4$ preferably represents unsubstituted $C_1$-$C_{20}$-alkyl or represents $C_1$-$C_{20}$-alkyl which is mono- or polysubstituted by identical or different substituents from the group consisting of fluorine, chlorine, bromine, iodine, $C_1$-$C_6$-alkylsulfanyl, $C_1$-$C_6$-alkylsulfinyl, $C_1$-$C_6$-alkylsulfonyl, $C_1$-$C_6$-alkoxy, $C_1$-$C_6$-alkylamino, di($C_1$-$C_6$-alkyl)amino, $C_1$-$C_6$-halogenoalkylsulfanyl, $C_1$-$C_6$-halogenoalkysulfinyl, $C_1$-$C_6$-halogenoalkylsulfonyl, $C_1$-$C_6$-halogenoalkoxy, $C_1$-$C_6$-halogenoalkylamino, di($C_1$-$C_6$-halogenoalkyl)

amino, —SiR⁶R⁷R⁸ and $C_3$-$C_6$-cycloalkyl, where the cycloalkyl moiety for its part may optionally be mono- or polysubstituted by identical or different substituents from the group consisting of fluorine, chlorine, bromine, iodine, $C_1$-$C_4$-alkyl and $C_1$-$C_4$-halogenoalkyl.

$Z^4$ particularly preferably represents unsubstituted $C_1$-$C_{20}$-alkyl.

$Z^4$ also particularly preferably represents $C_1$-$C_{20}$-alkyl which is substituted by fluorine, chlorine, bromine, iodine, $C_1$-$C_6$-alkylsulfanyl, $C_1$-$C_4$-alkylsulfinyl, $C_1$-$C_4$-alkylsulfonyl, $C_1$-$C_4$-alkoxy, $C_1$-$C_4$-alkylamino, di($C_1$-$C_4$-alkyl)amino, $C_1$-$C_4$-halogenoalkylsulfanyl, $C_1$-$C_4$-halogenoalkylsulfinyl, $C_1$-$C_4$-halogenoalkylsulfonyl, $C_1$-$C_4$-halogenoalkoxy, $C_1$-$C_4$-halogenoalkylamino, di($C_1$-$C_4$-halogenoalkyl)amino having in each case 1 to 9 fluorine, chlorine and/or bromine atoms, —SiR⁶R⁷R⁸, cyclopropyl, dichlorocyclopropyl, cyclobutyl, cyclopentyl or cyclohexyl;

$Z^4$ very particularly preferably represents $C_1$-$C_{20}$-alkyl which is substituted by fluorine, chlorine, methylsulfanyl, ethylsulfanyl, n- or isopropylsulfanyl, n-, iso-, sec-, tert-butylsulfanyl, pentylsulfanyl, hexylsulfanyl, methylsulfonyl, ethylsulfonyl, n- or isopropylsulfonyl, n-, iso-, sec-, tert-butylsulfonyl, methoxy, ethoxy, n- or isopropoxy, n-, iso-, sec-, tert-butoxy, methylamino, ethylamino, n- or isopropylamino, n-, iso-, sec-, tert-butylamino, dimethylamino, diisopropylamino, trifluoromethylsulfanyl, trifluoromethoxy, —SiR⁶R⁷R⁸, cyclopropyl, dichlorocyclopropyl, cyclobutyl, cyclopentyl or cyclohexyl.

Z furthermore, preferably represents $Z^5$.

$Z^5$ preferably represents $C_2$-$C_{20}$-alkenyl or $C_2$-$C_{20}$-alkynyl, each of which is optionally mono- or polysubstituted by identical or different substituents from the group consisting of fluorine, chlorine, bromine, iodine, $C_1$-$C_6$-alkylsulfanyl, $C_1$-$C_6$-alkylsulfinyl, $C_1$-$C_6$-alkylsulfonyl, $C_1$-$C_6$-alkoxy, $C_1$-$C_6$-alkylamino, di($C_1$-$C_6$-alkyl)amino, $C_1$-$C_6$-halogenoalkylsulfanyl, $C_1$-$C_6$-halogenoalkysulfinyl, $C_1$-$C_6$-halogenoalkylsulfonyl, $C_1$-$C_6$-halogenoalkoxy, $C_1$-$C_6$-halogenoalkylamino, di($C_1$-$C_6$-halogenoalkyl)amino, —SiR⁶R⁷R⁸ and $C_3$-$C_6$-cycloalkyl, where the cycloalkyl moiety for its part may optionally be mono- or polysubstituted by identical or different substituents from the group consisting of fluorine, chlorine, bromine, iodine, $C_1$-$C_4$-alkyl and $C_1$-$C_4$-halogenoalkyl.

$Z^5$ particularly preferably represents $C_2$-$C_{20}$-alkenyl or $C_2$-$C_{20}$-alkynyl, each of which is optionally substituted by fluorine, chlorine, bromine, iodine, $C_1$-$C_6$-alkylsulfanyl, $C_1$-$C_4$-alkylsulfinyl, $C_1$-$C_4$-alkylsulfonyl, $C_1$-$C_4$-alkoxy, $C_1$-$C_4$-alkylamino, di($C_1$-$C_4$-alkyl)amino, $C_1$-$C_4$-halogenoalkylsulfanyl, $C_1$-$C_4$-halogenoalkylsulfinyl, $C_1$-$C_4$-halogenoalkylsulfonyl, $C_1$-$C_4$-halogenoalkoxy, halogenoalkylamino, di($C_1$-$C_4$-halogenoalkyl)amino having in each case 1 to 9 fluorine, chlorine and/or bromine atoms, —SiR⁶R⁷R⁸, cyclopropyl, dichlorocyclopropyl, cyclobutyl, cyclopentyl or cyclohexyl;

$Z^5$ very particularly preferably represents $C_2$-$C_{20}$-alkenyl or $C_2$-$C_{20}$-alkynyl each of which is optionally substituted by fluorine, chlorine, bromine, iodine, cyclopropyl, dichlorocyclopropyl, cyclobutyl, cyclopentyl or cyclohexyl;

m preferably represents 0, 1 or 2.

$R^4$ preferably represents hydrogen or methyl.

$R^4$ particularly preferably represents hydrogen.

$R^5$ preferably represents hydrogen or methyl.

$R^5$ particularly preferably represents hydrogen.

$R^6$ and $R^7$ independently of one another preferably represent $C_1$-$C_6$-alkyl, $C_1$-$C_6$-alkoxy, $C_1$-$C_3$-alkoxy-$C_1$-$C_3$-alkyl or $C_1$-$C_3$-alkylsulfanyl-$C_1$-$C_3$-alkyl.

$R^6$ and $R^7$ independently of one another particularly preferably represent methyl, ethyl, methoxy, ethoxy, methoxymethyl, ethoxymethyl, methoxyethyl, ethoxyethyl, methylsulfanylmethyl, ethylsulfanylmethyl, methylsulfanylethyl or ethylsulfanylethyl.

$R^6$ and $R^7$ especially preferably each represent methyl.

$R^8$ preferably represents $C_1$-$C_6$-alkyl, $C_1$-$C_6$-alkoxy, $C_1$-$C_3$-alkoxy-$C_1$-$C_3$-alkyl, $C_1$-$C_3$-alkylsulfanyl-$C_1$-$C_3$-alkyl, $C_3$-$C_6$-cycloalkyl, phenyl or benzyl.

$R^8$ most preferably represents methyl.

Preference is given to those compounds of the formula (I) in which all radicals each have the meanings mentioned above as being preferred.

Particular preference is given to those compounds of the formula (I) in which all radicals each have the meanings mentioned above as being particularly preferred.

Preferred, and in each case to be understood as a sub-group of the compounds of the formula (I) mentioned above, are the following groups of novel carboxamides:

Group 1: Carboxamides of the formula (I-a)

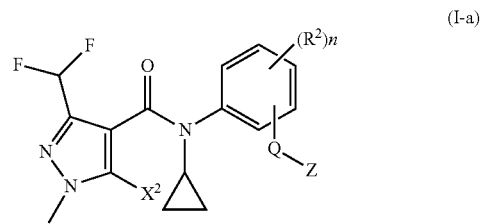

(I-a)

in which $X^2$, $R^2$, n, Q and Z are as defined above.

Group 2: Carboxamides of the formula (I-b)

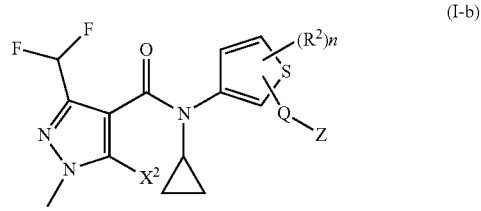

(I-b)

in which $X^2$, $R^2$, n, Q and Z are as defined above.

Group 3: Carboxamides of the formula (I-c)

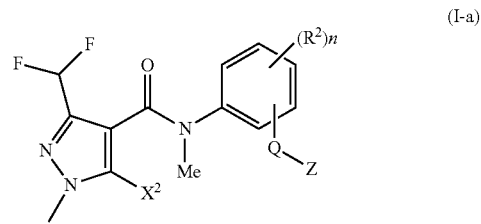

(I-a)

in which $X^2$, $R^2$, n, Q and Z are as defined above

Group 4: Carboxamides of the formula (I-d)

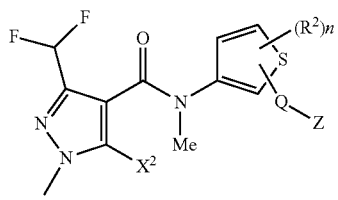

in which $X^2$, $R^2$, n, Q and Z are as defined above.

The definition $C_1$-$C_{20}$-alkyl comprises the largest range defined here for an alkyl radical. Specifically, this definition comprises the meanings methyl, ethyl, n-, isopropyl, n-, iso-, sec-, tert-butyl, and also in each case all isomeric pentyls, hexyls, heptyls, octyls, nonyls, decyls, undecyls, dodecyls, tridecyls, tetradecyls, pentadecyls, hexadecyls, heptadecyls, octadecyls, nonadecyls and eicosyls. A preferred range is $C_2$-$C_{12}$-alkyl, such as ethyl and straight-chain or branched propyl, butyl, pentyl, hexyl, heptyl, octyl, nonyl, decyl, undecyl and dodecyl, particularly straight-chain or branched $C_3$-$C_{10}$-alkyl, such as propyl, 1-methylethyl, butyl, 1-methylpropyl, 2-methylpropyl, 1,1-dimethylethyl, n-pentyl, 1-methylbutyl, 2-methylbutyl, 3-methylbutyl, 1,2-dimethylpropyl, 1,1-dimethylpropyl, 2,2-dimethylpropyl, 1-ethylpropyl, n-hexyl, 1-methylpentyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-3-methylpropyl, n-heptyl, 1-methylhexyl, 1-ethylpentyl, 2-ethylpentyl, 1-propylbutyl, octyl, 1-methylheptyl, 2-methylheptyl, 1-ethylhexyl, 2-ethylhexyl, 1-propylpentyl, 2-propylpentyl, nonyl, 1-methyloctyl, 2-methyloctyl, 1-ethylheptyl, 2-ethylheptyl, 1-propylhexyl, 2-propylhexyl, decyl, 1-methylnonyl, 2-methylnonyl, 1-ethyloctyl, 2-ethyloctyl, 1-propylheptyl and 2-propylheptyl, in particular propyl, 1-methylethyl, butyl, 1-methylbutyl, 2-methylbutyl, 3-methylbutyl, 1,1-dimethylethyl, 1,2-dimethylbutyl, 1,3-dimethylbutyl, pentyl, 1-methylbutyl, 1-ethylpropyl, hexyl, 3-methylpentyl, heptyl, 1-methylhexyl, 1-ethyl-3-methylbutyl, 1-methylheptyl, 1,2-dimethylhexyl, 1,3-dimethyloctyl, 4-methyloctyl, 1,2,2,3-tetramethylbutyl, 1,3,3-trimethylbutyl, 1,2,3-trimethylbutyl, 1,3-dimethylpentyl, 1,3-dimethylhexyl, 5-methyl-3-hexyl, 2-methyl-4-heptyl, 2,6-dimethyl-4-heptyl and 1-methyl-2-cyclopropylethyl.

Halogen-substituted alkyl represents, for example, chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 3-chloro-1-methylbutyl, 2-chloro-1-methylbutyl, 1-chlorobutyl, 3,3-dichloro-1-methylbutyl, 3-chloro-1-methylbutyl, 1-methyl-3-trifluoromethylbutyl, 3-methyl-1-trifluoromethylbutyl.

The substituent —$SiR^6R^7R^8$ preferably represents the following radicals: $SiMe_3$, $SiMe_2Et$, $SiMe_2CHMe_2$, $SiMe_2CH_2CHMe_2$, $SiMe_2CH_2CMe_3$, $SiMe_2OCHMe_2$, $SiMe_2OCH_2CHMe_2$, $SiMe_2OMe$, $SiMe_2CMe_3$, $SiMe_2CH_2CH_2Me$.

The definition $C_2$-$C_{20}$-alkenyl comprises the largest range defined here for an alkenyl radical. Specifically, this definition comprises the meanings ethenyl, n-, isopropenyl, n-, iso-, sec-, tert-butenyl, and also in each case all isomeric pentenyls, hexenyls, heptenyls, octenyls, nonenyls, decenyls, undecenyls, dodecenyls, tridecenyls, tetradecenyls, pentadecenyls, hexadecenyls, heptadecenyls, octadecenyls, nonadecenyls and eicosenyls, 1-methyl-1-propenyl, 1-ethyl-1-butenyl, 2,4-dimethyl-1-pentenyl, 2,4-dimethyl-2-pentenyl.

The definition $C_2$-$C_{20}$-alkynyl comprises the largest range defined here for an alkynyl radical. Specifically, this definition comprises the meanings ethynyl, n-, isopropynyl, n-, iso-, sec-, tert-butynyl, and also in each case all isomeric pentynyls, hexynyls, heptynyls, octynyls, nonynyls, decynyls, undecynyls, dodecynyls, tridecynyls, tetradecynyls, pentadecynyls, hexadecynyls, heptadecynyls, octadecynyls, nonadecynyls and eicosynyls.

Optionally substituted radicals may be mono- or polysubstituted, where in the case of polysubstitution, the substituents may be identical or different. Thus, the definition dialkylamino also embraces an amino group which is substituted asymmetrically by alkyl, such as, for example, methylethylamino.

Halogen-substituted radicals, such as, for example, halogenoalkyl, are mono- or polyhalogenated. In the case of polyhalogenation, the halogen atoms may be identical or different. Here, halogen represents fluorine, chlorine, bromine and iodine, in particular fluorine, chlorine and bromine.

However, the general or preferred radical definitions or illustrations given above can also be combined with one another as desired, i.e. including combinations between the respective ranges and preferred ranges. They apply to the end products and, correspondingly, to precursors and intermediates.

Carboxamides of the formula (Ia) where T represents oxygen are obtained when carbonyl halides or acids of formula (II)

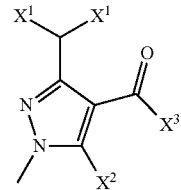

in which $X^1$ and $X^2$ are as defined above, $X^3$ represents halogen or hydroxy, are reacted with amines of formula (III)

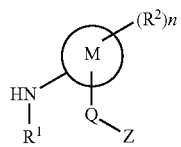

in which $R^1$, $R^2$, n, M, Q and Z are as defined above, if appropriate in the presence of a coupling agent, if appropriate in the presence of an acid binder and if appropriate in the presence of a diluent following the general process (a):

Process (a)

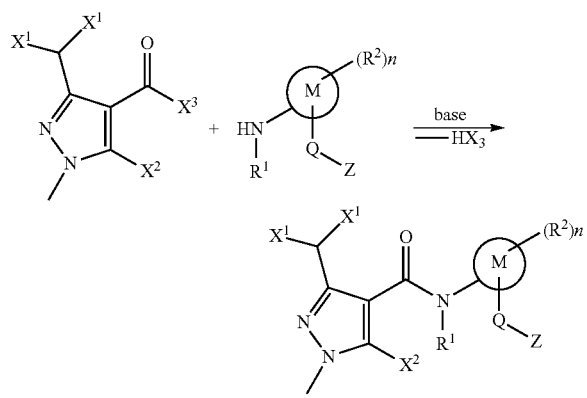

The formula (II) provides a general definition of the carbonyl halides or acids required as starting materials for carrying out the process (a) according to the invention. In this formula (II), $X^1$ and $X^2$ preferably, particularly preferably, very particularly preferably and especially preferably have those meanings which have already been mentioned in connection with the description of the compounds of the formula (I) according to the invention as being preferred, particularly preferred, etc., for this radical. $X^3$ preferably represents fluorine, chlorine or hydroxyl, particularly preferably chlorine or hydroxyl.

Thiocarboxamides of the formula (I) where T represents sulfur are obtained when carboxamides of the formula (I) where T represents oxygen are reacted according to process (b):

Process (b)

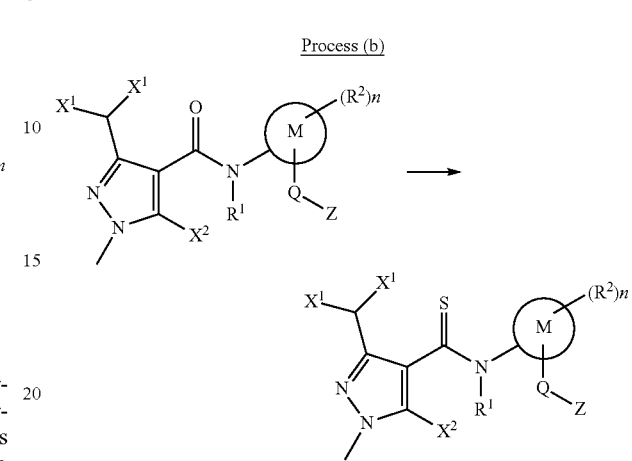

in the presence of a thionating agent and if appropriate in the presence of a catalytic or stoechiometric or more, quantity of a base.

The carbonyl halides or acids of the formula (II) can be prepared according to the process (c) illustrated according to the following reaction scheme:

Process (c)

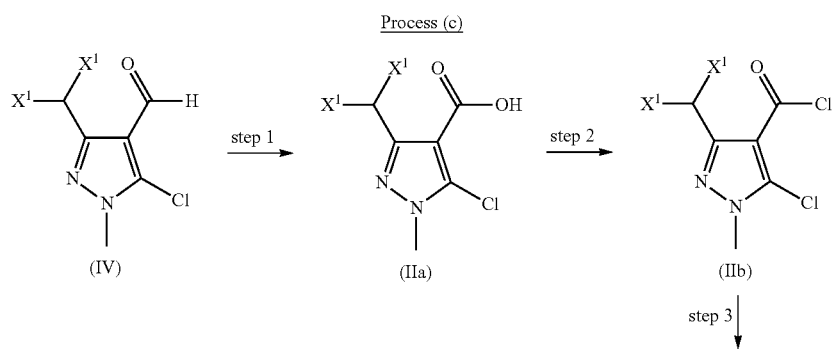

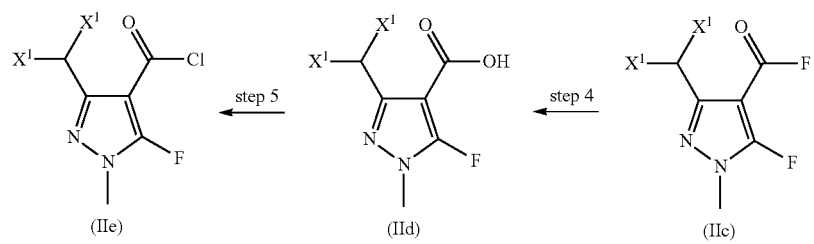

wherein X¹ is as herein-defined;
5-chloro-3-(difluoromethyl)-1-methyl-1H-pyrazole-4-carbaldehyde is known from WO-2004/014138 (reference example 35).

The amines of the formula (III) are known (e.g. WO-2007/068373).

Suitable diluents for carrying out the process (a) according to the invention are all inert organic solvents. These preferably include aliphatic, alicyclic or aromatic hydrocarbons, such as, for example, petroleum ether, hexane, heptane, cyclohexane, methylcyclohexane, benzene, toluene, xylene or decaline; halogenated hydrocarbons, such as, for example, chlorobenzene, dichlorobenzene, dichloromethane, chloroform, carbon tetrachloride, dichloroethane or trichloroethane; ethers, such as diethyl ether, diisopropyl ether, methyl t-butyl ether, methyl t-amyl ether, dioxane, tetrahydrofuran, 1,2-dimethoxyethane, 1,2-diethoxyethane or anisol; ketones, such as acetone, butanone, methyl isobutyl ketone or cyclohexanone; nitriles, such as acetonitrile, propionitrile, n- or i-butyronitrile or benzonitrile; amides, such as N,N-dimethylformamide, N,N-dimethylacetamide, N-methylformanilide, N-methylpyrrolidone or hexamethylphosphoric triamide; their mixtures with water or pure water.

The process (a) according to the invention is, if appropriate, carried out in the presence of a suitable acid acceptor when $X^3$ represents halogen. Suitable acid acceptors are all customary inorganic or organic bases. These preferably include alkaline earth metal or alkali metal hydrides, hydroxides, amides, alkoholates, acetates, carbonates or bicarbonates, such as, for example, sodium hydride, sodium amide, lithium diisopropylamide, sodium methoxide, sodium ethoxide, potassium tert-butoxide, sodium hydroxide, potassium hydroxide, sodium acetate, sodium carbonate, potassium carbonate, potassium bicarbonate, sodium bicarbonate or ammonium carbonate, and also tertiary amines, such as trimethylamine, triethylamine, tributylamine, N,N-dimethylaniline, N,N-dimethyl-benzylamine, pyridine, N-methylpiperidine, N-methylmorpholine, N,N-dimethylaminopyridine, diazabicyclooctane (DABCO), diaza-bicyclononene (DBN) or diazabicycloundecene (DBU).

The process (a) according to the invention is, if appropriate, carried out in the presence of a suitable coupling agent when $X^3$ represents hydroxy. Suitable coupling agents are all customary carbonyl activators. These preferably include N-[3-(dimethylamino)propyl]-N'-ethyl-carbodiimide-hydrochloride, N,N'-di-sec-butylcarbodiimide, N,N'-dicyclohexylcarbodiimide, N,N'-diisopropylcarbodiimide, 1-(3-(dimethylamino)propyl)-3-ethylcarbodiimide methiodide, 2-bromo-3-ethyl-4-methylthiazolium tetrafluoroborate, N,N-bis[2-oxo-3-oxazolidinyl]phosphorodiamidic chloride, chlorotri-pyrrolidinophosphonium hexafluorophosphate, bromtripyrrolidinophosphonium hexafluorophosphate, O-(1H-benzotriazol-1-yloxy)tris(dimethylamino)phosphonium hexafluorophosphate, O-(1H-benzotriazol-1-yl)-N,N,N',N'-tetramethyluronium hexafluorophosphate, O-(1H-benzotriazol-1-yl)-N,N,N',N'-bis(tetramethylene)uronium hexafluorophosphate, 0-(1H-benzotriazol-1-yl)-N,N,N',N'-bis-(tetramethylene)uronium tetrafluoroborate, N,N,N',N'-bis(tetramethylene)chlorouronium tetrafluoroborate, O-(7-azabenzotriazol-1-yl)-N,N,N,N-tetramethyluronium hexafluorophosphate and 1-hydroxybenzo-triazole. These reagents can be employed separately, but also in combination.

When carrying out the process (a) according to the invention, the reaction temperatures can be varied within a relatively wide range. In general, the process is carried out at temperatures of from 0° C. to 150° C., preferably at temperatures of from 20° C. to 110° C.

For carrying out the process (a) according to the invention for preparing the compounds of the formula (I) when T represents oxygen, in general from 0.2 to 5 mol, preferably from 0.5 to 2 mol, of amine of the formula (III) are employed per mole of the carbonyl halide or acid of the formula (II). Work-up is carried out by customary methods.

For carrying out the process (b) according to the invention for preparing the compounds of the formula (I) when T represents sulfur, starting amide derivatives of formula (I) when T represents oxygen can be prepared according to process (a).

Suitable thionating agents for carrying out process (c) according to the invention can be sulfur (S), sulfhydric acid ($H_2S$), sodium sulfide ($Na_2S$), sodium hydrosulfide (NaHS), boron trisulfide ($B_2S_3$), bis(diethylaluminium)sulfide (($AlEt_2)_2S$), ammonium sulfide (($NH_4)_2S$), phosphorous pentasulfide ($P_2S_5$), Lawesson's reagent (2,4-bis(4-methoxyphenyl)-1,2,3,4-dithiadiphosphetane 2,4-disulfide) or a polymer-supported thionating reagent such as described in Journal of the Chemical Society, Perkin 1 (2001), 358.

Step 1 of process (c) is performed in the presence of an oxidant, and if appropriate in the presence of a solvent.

Steps 2 and 5 of process (c) are performed in the presence of acid halide, and if appropriate in the presence of a solvent.

Step 3 of process (c) is performed in the presence of a fluorinating agent, and if appropriate in the presence of a solvent.

Step 4 of process (c) is performed in the presence of an acid or a base and if appropriate in the presence of a solvent.

Suitable oxidants for carrying out step 1 of process (c) according to the invention are in each case all inorganic and organic oxidant which are customary for such reactions. Preference is given to using benzyltriethylammonium permanganate, bromine, chlorine, m-chloroperbenzoic acid, chromic acid, chromium (VI) oxide, hydrogen peroxide, hydrogen peroxide-boron trifluoride, hydrogen peroxide-urea, 2-hydroxyperoxyhexafluoro-2-propanol; Iodine, oxygen-platinum catalyst, perbenzoic acid, peroxyacetyl nitrate, potassium permanganate, potassium ruthenate, pyridinium dichromate, ruthenium (VIII) oxide, silver (I) oxide, silver (II) oxide, silver nitrite, sodium chlorite, sodium hypochlorite, or 2,2,6,6-tetramethylpiperidin-1-oxyl.

Suitable acid halides for carrying out steps 2 and 5 of process (c) according to the invention are in each case all organic or inorganic acid halides which are customary for such reactions. Preference is given to using notably phosgene, phosphorous trichloride, phosphorous pentachloride, phosphorous trichloride oxide, thionyl chloride, or carbon tetrachloride-triphenylphosphine.

Suitable fluorinating agent for carrying out step 3 of process (c) according to the invention is in each case all fluorinating agents which are customary for such reactions. Preference is given to using cesium fluoride, potassium fluoride, potassium fluoride-calcium difluoride, or tetrabutylammonium fluoride.

When carrying out steps 1 to 5 of process (c) according to the invention, the reaction temperatures can independently be varied within a relatively wide range. Generally, processes according to the invention are carried out at temperatures between 0° C. and 160° C., preferably between 10° C. and 120° C. A way to control the temperature for the processes according to the invention is to use the micro-waves technology.

Steps 1 to 5 of process (c) according to the invention are generally independently carried out under atmospheric pressure. However, in each case, it is also possible to operate under elevated or reduced pressure.

When carrying out step 1 of process (c) according to the invention, generally one mole or other an excess of the oxidant is employed per mole of aldehyde of formula (IV). It is also possible to employ the reaction components in other ratios.

When carrying out carrying out steps 2 and 5 of process (c) to the invention, generally one mole or other an excess of the acid halides is employed per mole of acid of formula (IIIa) or (IIId). It is also possible to employ the reaction components in other ratios.

When carrying out steps 3 of process (c) according to the invention generally one mole or other an excess of fluorinating agent is employed per mole of acid chloride (IIIb). It is also possible to employ the reaction components in other ratios.

When carrying out steps 4 of process (c) according to the invention generally one mole or other an excess of acid or base is employed per mole of acid fluoride (IIIc). It is also possible to employ the reaction components in other ratios.

The processes (a), (b) and (c) according to the invention are generally carried out under atmospheric pressure. However, it is also possible to operate under elevated or reduced pressure—in general between 0.1 bar and 10 bar.

The compounds according to the invention exhibit a potent microbicidal activity and can be employed in plant protection and in the protection of materials for controlling undesirable microorganisms such as fungi and bacteria.

Fungicides can be employed in plant protection for controlling Plasmodiophoromycetes, Oomycetes, Chytridiomycetes, Zygomycetes, Ascomycetes, Basidiomycetes and Deuteromycetes.

Bactericides can be employed in plant protection for combating Pseudomonadaceae, Rhizobiaceae, Enterobacteriaceae, Corynebacteriaceae and Streptomycetaceae.

Examples which may be mentioned, but not by limitation, are some pathogens of fungal and bacterial diseases which come under the abovementioned general terms are:
diseases caused by powdery mildew pathogens, such as, for example
*Blumeria* species such as, for example, *Blumeria graminis;*
*Podosphaera* species such as, for example, *Podosphaera leucotricha;*
*Sphaerotheca* species such as, for example, *Sphaerotheca fuliginea;*
*Uncinula* species such as, for example, *Uncinula necator;*
diseases caused by rust pathogens such as, for example,
*Gymnosporangium* species such as, for example, *Gymnosporangium sabinae*
*Hemileia* species such as, for example, *Hemileia vastatrix;*
*Phakopsora* species such as, for example, *Phakopsora pachyrhizi* and *Phakopsora meibomiae;*
*Puccinia* species such as, for example, *Puccinia recondita* or *Puccina graminis;*
*Uromyces* species such as, for example, *Uromyces appendiculatus;*
diseases caused by pathogens from the Oomycetene group such as, for example,
*Bremia* species such as, for example, *Bremia lactucae;*
*Peronospora* species such as, for example, *Peronospora pisi* or *P. brassicae;*
*Phytophthora* species such as, for example, *Phytophthora infestans;*
*Plasmopara* species such as, for example, *Plasmopara viticola;*
*Pseudoperonospora* species such as, for example, *Pseudoperonospora humuli* or *Pseudoperonospora cubensis;*
*Pythium* species such as, for example, *Pythium ultimum;*
leaf spot diseases and leaf wilts caused by, for example,
*Alternaria* species such as, for example, *Alternaria solani;*
*Cercospora* species such as, for example, *Cercospora beticola;*
*Cladosporum* species such as, for example, *Cladosporium cucumerinum;*
*Cochliobolus* species such as, for example, *Cochliobolus sativus*
(conidial form: *Drechslera*, syn: *Helminthosporium*);
*Colletotrichum* species such as, for example, *Colletotrichum lindemuthanium;*
*Cycloconium* species such as, for example, *Cycloconium oleaginum;*
*Diaporthe* species such as, for example, *Diaporthe citri;*
*Elsinoe* species such as, for example, *Elsinoe fawcettii;*
*Gloeosporium* species such as, for example, *Gloeosporium laeticolor;*
*Glomerella* species such as, for example, *Glomerella cingulata;*
*Guignardia* species such as, for example, *Guignardia bidwelli;*
*Leptosphaeria* species such as, for example, *Leptosphaeria maculans;*
*Magnaporthe* species such as, for example, *Magnaporthe grisea;*
*Mycosphaerella* species such as, for example, *Mycosphaerella graminicola* and *Mycosphaerella fijiensis;*
*Phaeosphaeria* species such as, for example, *Phaeosphaeria nodorum;*
*Pyrenophora* species such as, for example, *Pyrenophora teres;*
*Ramularia* species such as, for example, *Ramularia collocygni;*
*Rhynchosporium* species such as, for example, *Rhynchosporium secalis;*
*Septoria* species such as, for example, *Septoria apii;*
*Typhula* species such as, for example, *Typhula incarnata;*
*Venturia* species such as, for example, *Venturia inaequalis;*
root and stem diseases caused by, for example,
*Corticium* species such as, for example, *Corticium graminearum;*
*Fusarium* species such as, for example, *Fusarium oxysporum;*
*Gaeumannomyces* species such as, for example, *Gaeumannomyces graminis;*
*Rhizoctonia* species such as, for example, *Rhizoctonia solani;*
*Tapesia* species such as, for example, *Tapesia acuformis* or *Tapesia yallundae;*
*Thielaviopsis* species such as, for example, *Thielaviopsis basicola;*
ear and panicle diseases (including maize cobs), caused by, for example,
*Alternaria* species such as, for example, *Alternaria* spp.;
*Aspergillus* species such as, for example, *Aspergillus flavus;*
*Cladosporium* species such as, for example, *Cladosporium cladosporioides;*
*Claviceps* species such as, for example, *Claviceps purpurea;*
*Fusarium* species such as, for example, *Fusarium culmorum;*
*Gibberella* species such as, for example, *Gibberella zeae;*
*Monographella* species such as, for example, *Monographella nivalis;*
diseases caused by smuts such as, for example,
*Sphacelotheca* species such as, for example, *Sphacelotheca reiliana;*
*Tilletia* species such as, for example, *Tilletia caries;*
*Urocystis* species such as, for example, *Urocystis occulta;*
*Ustilago* species such as, for example, *Ustilago nuda;* fruit rots caused by, for example,
*Aspergillus* species such as, for example, *Aspergillus flavus*;
*Botrytis* species such as, for example, *Botrytis cinerea*;
*Penicillium* species such as, for example, *Penicillium expansum* and *Penicillium purpurogenum*;
*Sclerotinia* species such as, for example, *Sclerotinia sclerotiorum*;
*Verticilium* species such as, for example, *Verticilium alboatrum*;
seed- and soil-borne rot and wilts, and seedling diseases, caused by, for example,
*Fusarium* species such as, for example, *Fusarium culmorum*;
*Phytophthora* species such as, for example, *Phytophthora cactorum*;
*Pythium* species such as, for example, *Pythium ultimum*;
*Rhizoctonia* species such as, for example, *Rhizoctonia solani*;
*Sclerotium* species such as, for example, *Sclerotium rolfsii*;
cancers, galls and witches' broom disease, caused by, for example,
*Nectria* species such as, for example, *Nectria galligena*;
wilts caused by, for example,
*Monilinia* species such as, for example, *Monilinia laxa*;
deformations of leaves, flowers and fruits, caused by, for example,
*Taphrina* species such as, for example, *Taphrina deformans*;
degenerative diseases of woody species, caused by, for example,
*Esca* species such as, for example, *Phaeomoniella clamydospora* and *Phaeoacremonium aleophilum* and *Fomitiporia mediterranea*;
diseases of flowers and seeds, caused by, for example,
*Botrytis* species such as, for example, *Botrytis cinerea*;
diseases of the plant tubers, caused by, for example,
*Rhizoctonia* species such as, for example, *Rhizoctonia solani*;
*Helminthosporium* species such as, for example, *Helminthosporium solani*;
diseases caused by bacterial pathogens such as, for example,
*Xanthomonas* species such as, for example, *Xanthomonas campestris* pv. *oryzae*;
*Pseudomonas* species such as, for example, *Pseudomonas syringae* pv. *lachrymans*;
*Erwinia* species such as, for example, *Erwinia amylovora*.

The following diseases of soybeans can preferably be controlled:
Fungal diseases on leaves, stems, pods and seeds caused by, for example,
alternaria leaf spot (*Alternaria* spec. *atrans tenuissima*), anthracnose (*Colletotrichum gloeosporoides dematium* var. *truncatum*), brown spot (*Septoria glycines*), cercospora leaf spot and blight (*Cercospora kikuchii*), choanephora leaf blight (*Choanephora infundibulifera trispora* (syn.)), dactuliophora leaf spot (*Dactuliophora glycines*), downy mildew (*Peronospora manshurica*), drechslera blight (*Drechslera glycini*), frogeye leaf spot (*Cercospora sojina*), leptosphaerulina leaf spot (*Leptosphaerulina trifolii*), phyllostica leaf spot (*Phyllosticta sojaecola*), pod and stem blight (*Phomopsis sojae*), powdery mildew (*Microsphaera diffusa*), pyrenochaeta leaf spot (*Pyrenochaeta glycines*), rhizoctonia aerial, foliage, and web blight (*Rhizoctonia solani*), rust (*Phakopsora pachyrhizi*), scab (*Sphaceloma glycines*), stemphylium leaf blight (*Stemphylium botryosum*), target spot (*Corynespora cassiicola*);
fungal diseases on roots and the stem base caused by, for example,
black root rot (*Calonectria crotalariae*), charcoal rot (*Macrophomina phaseolina*), fusarium blight or wilt, root rot, and pod and collar rot (*Fusarium oxysporum, Fusarium ortho-
ceras, Fusarium semitectum, Fusarium equiseti*), mycoleptodiscus root rot (*Mycoleptodiscus terrestris*), neocosmospora (*Neocosmospora vasinfecta*), pod and stem blight (*Diaporthe phaseolorum*), stem canker (*Diaporthe phaseolorum* var. *caulivora*), phytophthora rot (*Phytophthora megasperma*), brown stem rot (*Phialophora gregata*), pythium rot (*Pythium aphanidermatum, Pythium irregulare, Pythium debaryanum, Pythium myriotylum, Pythium ultimum*), rhizoctonia root rot, stem decay, and damping-off (*Rhizoctonia solani*), sclerotinia stem decay (*Sclerotinia sclerotiorum*), sclerotinia southern blight (*Sclerotinia rolfsii*), thielaviopsis root rot (*Thielaviopsis basicola*).

The active compounds according to the invention also have a potent strengthening effect in plants. They are therefore suitable for mobilizing the plants' defenses against attack by undesired microorganisms.

Plant-strengthening (resistance-inducing) substances are understood as meaning, in the present context, those substances which are capable of stimulating the defense system of plants in such a way that, when subsequently inoculated with undesired microorganisms, the treated plants display a substantial degree of resistance to these microorganisms.

In the present case, undesired microorganisms are understood as meaning phytopathogenic fungi, bacteria and viruses. Thus, the substances according to the invention can be employed for protecting plants against attack by the above-mentioned pathogens within a certain period of time after the treatment. The period of time within which their protection is effected is generally extended from 1 to 28 days, preferably from 1 to 14 days, particularly preferably from 1 to 7 days, after the plants have been treated with the active compounds.

The fact that the active compounds, at the concentrations required for the controlling of plant diseases, are well tolerated by plants permits the treatment of aerial plant parts, of vegetative propagation material and seed, and of the soil.

In this context, the active compounds according to the invention can be employed particularly successfully for controlling cereal diseases such as, for example, against *Puccinia* species and of diseases in viticulture, fruit production and vegetable production such as, for example against *Botrytis*, *Venturia* or *Alternaria* species.

The active compounds according to the invention are also suitable for increasing the yield. Moreover, they display a low degree of toxicity and are well tolerated by plants.

If appropriate, the active compounds according to the invention can also be used in certain concentrations and application rates as herbicides, for influencing plant growth and for controlling animal pests. If appropriate, they can also be employed as intermediates and precursors for the synthesis of further active compounds.

All plants and plant parts can be treated in accordance with the invention. Plants are understood as meaning, in the present context, all plants and plant populations, such as desired and undesired wild plants or crop plants (including naturally occurring crop plants). Crop plants may be plants which can be obtained by conventional breeding and optimization methods or else by biotechnological and genetic engineering methods or by combinations of these methods, including the transgenic plants and including the plant varieties capable or not capable of being protected by Plant Breeders' rights. Plant parts are understood as meaning all aerial and subterranean parts and organs of the plants, such as shoot, leaf, flower and root, examples which may be mentioned being leaves, needles, stalks, stems, flowers, fruiting bodies, fruits and seeds, and also roots, tubers and rhizomes. The plant parts also include harvested material and vegetative and generative propagation material, for example cuttings, tubers, rhizomes, slips and seeds.

The treatment according to the invention with the active compounds, of the plants and plant parts, is carried out directly or by acting on their environment, habitat, or store by the customary treatment methods, for example by immersion, spraying, vaporizing, fogging, broadcasting, painting on and, in the case of propagation material, in particular in the case of seeds, furthermore by coating with one or more coats.

In the protection of materials, the substances according to the invention can be employed for protecting industrial materials against attack and destruction by undesired microorganisms.

In the present context, industrial materials are understood as meaning non-live materials which have been made for use in technology. For example, industrial materials which are to be protected by active compounds according to the invention from microbial modification or destruction can be glues, sizes, paper and board, textiles, leather, timber, paints and plastic articles, cooling lubricants and other materials which are capable of being attacked or destroyed by microorganisms. Parts of production plants, for example cooling-water circuits, which can be adversely affected by the multiplication of microorganisms may also be mentioned within the materials to be protected. Industrial materials which may be mentioned with preference for the purposes of the present invention are glues, sizes, paper and board, leather, timber, paints, cooling lubricants and heat-transfer fluids, especially preferably wood.

Microorganisms which are capable of bringing about a degradation or modification of the industrial materials and which may be mentioned are, for example, bacteria, fungi, yeasts, algae and slime organisms. The active compounds according to the invention are preferably active against fungi, in particular moulds, wood-discolouring and wood-destroying fungi (Basidiomycetes) and against slime organisms and algae.

Examples which may be mentioned are microorganisms of the following genera:
*Alternaria* such as *Alternaria tenuis*,
*Aspergillus* such as *Aspergillus niger*,
*Chaetomium* such as *Chaetomium globosum*,
*Coniophora* such as *Coniophora puetana*,
*Lentinus* such as *Lentinus tigrinus*,
*Penicillium* such as *Penicillium glaucum*,
*Polyporus* such as *Polyporus versicolor*,
*Aureobasidium* such as *Aureobasidium pullulans*,
*Sclerophoma* such as *Sclerophoma pityophila*,
*Trichoderma* such as *Trichoderma viride*,
*Escherichia* such as *Escherichia coli*,
*Pseudomonas* such as *Pseudomonas aeruginosa*,
*Staphylococcus* such as *Staphylococcus aureus*.

Depending on their respective physical and/or chemical properties, the active compounds can be converted to the customary formulations, such as solutions, emulsions, suspensions, powders, foams, pastes, granules, aerosols, very fine capsules in polymeric substances and in coating compositions for seed, and also ULV cold- and warm-fogging formulations.

These formulations are produced in a known manner, for example by mixing the active compounds with extenders, that is, liquid solvents, pressurized liquefied gases and/or solid carriers, optionally with the use of surface-active agents, that is emulsifers and/or dispersants, and/or foam formers. If the extender used is water, it is also possible to employ for example organic solvents as cosolvents. Suitable liquid solvents are essentially: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulfoxide, and also water. Liquefied gaseous extenders or carriers are those liquids which are gaseous at ambient temperature and at atmospheric pressure, for example aerosol propellants such as halogenated hydrocarbons and also butane, propane, nitrogen and carbon dioxide. As solid carriers there are suitable: for example ground natural minerals, such as kaolins, clays, talc, chalk, quartz, attapulgite, montmorillonite or diatomaceous earth, and ground synthetic minerals, such as finely divided silica, alumina and silicates. As solid carriers for granules there are suitable: for example crushed and fractionated natural rocks such as calcite, pumice, marble, sepiolite and dolomite, and also synthetic granules of inorganic and organic meals, and granules of organic material such as sawdust, coconut shells, maize cobs and tobacco stalks. As emulsifiers and/or foam formers there are suitable: for example non-ionic and anionic emulsifiers, such as polyoxyethylene fatty acid esters, polyoxyethylene fatty alcohol ethers, for example alkylaryl polyglycol ethers, alkylsulfonates, alkylsulfates, arylsulfonates and protein hydrolysates. As dispersants there are suitable: for example lignin-sulfite waste liquors and methylcellulose.

Tackifiers such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other possible additives are mineral and vegetable oils.

It is possible to use colourants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95% by weight of active compound, preferably between 0.5 and 90%.

The active compounds according to the invention, as such or in their formulations, can also be used as a mixture with known fungicides, bactericides, acaricides, nematicides, or insecticides, for example, to improve the activity spectrum or prevent the development of resistance.

Examples of suitable fungicide mixing partners can be selected in the following lists:
(1) Inhibitors of the ergosterol biosynthesis, for example (1.1) aldimorph (1704-28-5), (1.2) azaconazole (60207-31-0), (1.3) bitertanol (55179-31-2), (1.4) bromuconazole (116255-48-2), (1.5) cyproconazole (113096-99-4), (1.6) diclobutrazole (75736-33-3), (1.7) difenoconazole (119446-68-3), (1.8) diniconazole (83657-24-3), (1.9) diniconazole-M (83657-18-5), (1.10) dodemorph (1593-77-7), (1.11) dodemorph acetate (31717-87-0), (1.12) epoxiconazole (106325-08-0), (1.13) etaconazole (60207-93-4), (1.14) fenarimol (60168-88-9), (1.15) fenbuconazole (114369-43-6), (1.16) fenhexamid (126833-17-8), (1.17) fenpropidin (67306-00-7), (1.18) fenpropimorph (67306-03-0), (1.19) fluquinconazole (136426-54-5), (1.20) flurprimidol (56425-91-3), (1.21) flusilazole (85509-19-9), (1.22) flutriafol (76674-21-0), (1.23) furconazole (112839-33-5), (1.24) furconazole-cis (112839-32-4), (1.25) hexaconazole (79983-71-4), (1.26) imazalil (60534-80-7), (1.27) imazalil sulfate (58594-72-2), (1.28) imibenconazole (86598-92-7), (1.29) ipconazole (125225-28-7), (1.30) metconazole (125116-23-6), (1.31) myclobutanil (88671-89-0), (1.32) naftifine (65472-88-0), (1.33) nuarimol (63284-71-9), (1.34) oxpoconazole (174212-12-5), (1.35) paclobutrazol (76738-62-0), (1.36) pefurazoate (101903-30-4), (1.37) penconazole (66246-88-6), (1.38) piperalin (3478-94-2), (1.39) prochloraz (67747-09-5), (1.40) propiconazole (60207-90-1), (1.41) prothioconazole (178928-70-6), (1.42) pyributicarb (88678-67-5), (1.43) pyrifenox (88283-41-4), (1.44) quinconazole (103970-75-8), (1.45) simeconazole (149508-90-7), (1.46) spiroxamine (118134-30-8), (1.47) tebuconazole (107534-96-3), (1.48) terbinafine (91161-71-6), (1.49) tetraconazole (112281-77-3), (1.50) triadimefon (43121-43-3), (1.51) triadimenol (89482-17-7), (1.52) tridemorph (81412-43-3), (1.53) triflumizole (68694-11-1), (1.54) triforine (26644-46-2), (1.55) triticonazole (131983-72-7), (1.56) uniconazole (83657-22-1), (1.57) uniconazole-p (83657-17-4), (1.58) viniconazole (77174-66-4), (1.59) voriconazole (137234-62-9), (1.60) 1-(4-chlorophenyl)-2-(1H-1,2,4-triazol-1-yl)cycloheptanol (129586-32-9), (1.61) methyl 1-(2,2-dimethyl-2,3-dihydro-1H-inden-1-yl)-1H-imidazole-5-carboxylate (110323-95-0), (1.62) N'-{5-(difluoromethyl)-2-methyl-4-[3-(trimethylsilyl)propoxy]phenyl}-N-ethyl-N-methylimidoformamide, (1.63) N-ethyl-N-methyl-N'-{2-methyl-5-(trifluoromethyl)-4-[3-(trimethylsilyl)propoxy]phenyl}imidoformamide and (1.64) O-[1-(4-methoxyphenoxy)-3,3-dimethylbutan-2-yl] 1H-imidazole-1-carbothioate (111226-71-2).

(2) inhibitors of the respiratory chain at complex I or II, for example (2.1) bixafen (581809-46-3), (2.2) boscalid (188425-85-6), (2.3) carboxin (5234-68-4), (2.4) diflumetorim (130339-07-0), (2.5) fenfuram (24691-80-3), (2.6) fluopyram (658066-35-4), (2.7) flutolanil (66332-96-5), (2.8) fluxapyroxad (907204-31-3), (2.9) furametpyr (123572-88-3), (2.10) furmecyclox (60568-05-0), (2.11) isopyrazam (mixture of syn-epimeric racemate 1RS,4SR,9RS and anti-epimeric racemate 1RS,4SR,9SR) (881685-58-1), (2.12) isopyrazam (anti-epimeric racemate 1RS,4SR,9SR), (2.13) isopyrazam (anti-epimeric enantiomer 1R,4S,9S), (2.14) isopyrazam (anti-epimeric enantiomer 1S,4R,9R), (2.15) isopyrazam (syn epimeric racemate 1RS,4SR,9RS), (2.16) isopyrazam (syn-epimeric enantiomer 1R,4S,9R), (2.17) isopyrazam (syn-epimeric enantiomer 1S,4R,9S), (2.18) mepronil (55814-41-0), (2.19) oxycarboxin (5259-88-1), (2.20) penflufen (494793-67-8), (2.21) penthiopyrad (183675-82-3), (2.22) sedaxane (874967-67-6), (2.23) thifluzamide (130000-40-7), (2.24) 1-methyl-N-[2-(1,1,2,2-tetrafluoroethoxy)phenyl]-3-(trifluoromethyl)-1H-pyrazole-4-carboxamide, (2.25) 3-(difluoromethyl)-1-methyl-N-[2-(1,1,2,2-tetrafluoroethoxy)phenyl]-1H-pyrazole-4-carboxamide, (2.26) 3-(difluoromethyl)-N-[4-fluoro-2-(1,1,2,3,3,3-hexafluoropropoxy)phenyl]-1-methyl-1H-pyrazole-4-carboxamide, (2.27) N-[1-(2,4-dichlorophenyl)-1-methoxypropan-2-yl]-3-(difluoromethyl)-1-methyl-1H-pyrazole-4-carboxamide (1092400-95-7) (WO 2008148570), (2.28) 5,8-difluoro-N-[2-(2-fluoro-4-{[4-(trifluoromethyl)pyridin-2-yl]oxy}phenyl)ethyl]quinazolin-4-amine (1210070-84-0) (WO2010025451), (2.29) N-[9-(dichloromethylene)-1,2,3,4-tetrahydro-1,4-methanonaphthalen-5-yl]-3-(difluoromethyl)-1-methyl-1H-pyrazole-4-carboxamide, (2.30) N-[(1S,4R)-9-(dichloromethylene)-1,2,3,4-tetrahydro-1,4-methanonaphthalen-5-yl]-3-(difluoromethyl)-1-methyl-1H-pyrazole-4-carboxamide and (2.31) N-[(1R,4S)-9-(dichloromethylene)-1,2,3,4-tetrahydro-1,4-methanonaphthalen-5-yl]-3-(difluoromethyl)-1-methyl-1H-pyrazole-4-carboxamide.

(3) inhibitors of the respiratory chain at complex III, for example (3.1) ametoctradin (865318-97-4), (3.2) amisulbrom (348635-87-0), (3.3) azoxystrobin (131860-33-8), (3.4) cyazofamid (120116-88-3), (3.5) coumethoxystrobin (850881-30-0), (3.6) coumoxystrobin (850881-70-8), (3.7) dimoxystrobin (141600-52-4), (3.8) enestroburin (238410-11-2) (WO 2004/058723), (3.9) famoxadone (131807-57-3) (WO 2004/058723), (3.10) fenamidone (161326-34-7) (WO 2004/058723), (3.11) fenoxystrobin (918162-02-4), (3.12) fluoxastrobin (361377-29-9) (WO 2004/058723), (3.13) kresoxim-methyl (143390-89-0) (WO 2004/058723), (3.14) metominostrobin (133408-50-1) (WO 2004/058723), (3.15) orysastrobin (189892-69-1) (WO 2004/058723), (3.16) picoxystrobin (117428-22-5) (WO 2004/058723), (3.17) pyraclostrobin (175013-18-0) (WO 2004/058723), (3.18) pyrametostrobin (915410-70-7) (WO 2004/058723), (3.19) pyraoxystrobin (862588-11-2) (WO 2004/058723), (3.20) pyribencarb (799247-52-2) (WO 2004/058723), (3.21) triclopyricarb (902760-40-1), (3.22) trifloxystrobin (141517-21-7) (WO 2004/058723), (3.23) (2E)-2-(2-{[6-(3-chloro-2-methylphenoxy)-5-fluoropyrimidin-4-yl]oxy}phenyl)-2-(methoxyimino)-N-methylethanamide (WO 2004/058723), (3.24) (2E)-2-(methoxyimino)-N-methyl-2-(2-{[({(1E)-1-[3-(trifluoromethyl)phenyl]ethylidene}amino)oxy]methyl}phenyl)ethanamide (WO 2004/058723), (3.25) (2E)-2-(methoxyimino)-N-methyl-2-{2-[(E)-({1-[3-(trifluoromethyl)phenyl]ethoxy}imino)methyl]phenyl}ethanamide (158169-73-4), (3.26) (2E)-2-{2-[({[(1E)-1-(3-{[(E)-1-fluoro-2-phenylethenyl]oxy}phenyl)ethylidene]amino}oxy)methyl]phenyl}-2-(methoxyimino)-N-methylethanamide (326896-28-0), (3.27) (2E)-2-{2-[({[(2E,3E)-4-(2,6-dichlorophenyl)but-3-en-2-ylidene]amino}oxy)methyl]phenyl}-2-(methoxyimino)-N-methylethanamide, (3.28) 2-chloro-N-(1,1,3-trimethyl-2,3-dihydro-1H-inden-4-yl)pyridine-3-carboxamide (119899-14-8), (3.29) 5-methoxy-2-methyl-4-(2-{[({(1E)-1-[3-(trifluoromethyl)phenyl]ethylidene}amino)oxy]methyl}phenyl)-2,4-dihydro-3H-1,2,4-triazol-3-one, (3.30) methyl (2E)-2-{2-[({cyclopropyl[(4-methoxyphenyl)imino]methyl}sulfanyl)methyl]phenyl}-3-methoxyprop-2-enoate (149601-03-6), (3.31) N-(3-ethyl-3,5,5-trimethylcyclohexyl)-3-(formylamino)-2-hydroxybenzamide (226551-21-9), (3.32) 2-{2-[(2,5-dimethylphenoxy)methyl]phenyl}-2-methoxy-N-methylacetamide (173662-97-0) and (3.33) (2R)-2-{2-[(2,5-dimethylphenoxy)methyl]phenyl}-2-methoxy-N-methylacetamide (394657-24-0).

(4) Inhibitors of the mitosis and cell division, for example (4.1) benomyl (17804-35-2), (4.2) carbendazim (10605-21-7), (4.3) chlorfenazole (3574-96-7), (4.4) diethofencarb (87130-20-9), (4.5) ethaboxam (162650-77-3), (4.6) fluopicolide (239110-15-7), (4.7) fuberidazole (3878-19-1), (4.8) pencycuron (66063-05-6), (4.9) thiabendazole (148-79-8), (4.10) thiophanate-methyl (23564-05-8), (4.11) thiophanate (23564-06-9), (4.12) zoxamide (156052-68-5), (4.13) 5-chloro-7-(4-methylpiperidin-1-yl)-6-(2,4,6-trifluorophenyl)[1,2,4]triazolo[1,5-a]pyrimidine (214706-53-3) and (4.14) 3-chloro-5-(6-chloropyridin-3-yl)-6-methyl-4-(2,4,6-trifluorophenyl)pyridazine (1002756-87-7).

(5) Compounds capable to have a multisite action, like for example (5.1) bordeaux mixture (8011-63-0), (5.2) captafol (2425-06-1), (5.3) captan (133-06-2) (WO 02/12172), (5.4) chlorothalonil (1897-45-6), (5.5) copper hydroxide (20427-59-2), (5.6) copper naphthenate (1338-02-9), (5.7) copper oxide (1317-39-1), (5.8) copper oxychloride (1332-40-7), (5.9) copper (2+) sulfate (7758-98-7), (5.10) dichlofluanid (1085-98-9), (5.11) dithianon (3347-22-6), (5.12) dodine (2439-10-3), (5.13) dodine free base, (5.14) ferbam (14484-64-1), (5.15) fluorofolpet (719-96-0), (5.16) folpet (133-07-3), (5.17) guazatine (108173-90-6), (5.18) guazatine acetate, (5.19) iminoctadine (13516-27-3), (5.20) iminoctadine albesilate (169202-06-6), (5.21) iminoctadine triacetate (57520-17-9), (5.22) mancopper (53988-93-5), (5.23) mancozeb (8018-01-7), (5.24) maneb (12427-38-2), (5.25) metiram (9006-42-2), (5.26) metiram zinc (9006-42-2), (5.27) oxine-copper (10380-28-6), (5.28) propamidine (104-32-5), (5.29) propineb (12071-83-9), (5.30) sulfur and sulfur preparations including calcium polysulfide (7704-34-9), (5.31) thiram (137-26-8), (5.32) tolylfluanid (731-27-1), (5.33) zineb (12122-67-7) and (5.34) ziram (137-30-4).

(6) Compounds capable to induce a host defence, for example (6.1) acibenzolar-S-methyl (135158-54-2), (6.2) isotianil (224049-04-1), (6.3) probenazole (27605-76-1) and (6.4) tiadinil (223580-51-6).

(7) Inhibitors of the amino acid and/or protein biosynthesis, for example (7.1) andoprim (23951-85-1), (7.2) blasticidin-S (2079-00-7), (7.3) cyprodinil (121552-61-2), (7.4) kasugamycin (6980-18-3), (7.5) kasugamycin hydrochloride hydrate (19408-46-9), (7.6) mepanipyrim (110235-47-7), (7.7) pyrimethanil (53112-28-0) and (7.8) 3-(5-fluoro-3,3,4,4-tetramethyl-3,4-dihydroisoquinolin-1-yl)quinoline (861647-32-7) (WO2005070917).

(8) Inhibitors of the ATP production, for example (8.1) fentin acetate (900-95-8), (8.2) fentin chloride (639-58-7), (8.3) fentin hydroxide (76-87-9) and (8.4) silthiofam (175217-20-6).

(9) Inhibitors of the cell wall synthesis, for example (9.1) benthiavalicarb (177406-68-7), (9.2) dimethomorph (110488-70-5), (9.3) flumorph (211867-47-9), (9.4) iprovalicarb (140923-17-7), (9.5) mandipropamid (374726-62-2), (9.6) polyoxins (11113-80-7), (9.7) polyoxorim (22976-86-9), (9.8) validamycin A (37248-47-8) and (9.9) valifenalate (283159-94-4; 283159-90-0).

(10) Inhibitors of the lipid and membrane synthesis, for example (10.1) biphenyl (92-52-4), (10.2) chloroneb (2675-77-6), (10.3) dicloran (99-30-9), (10.4) edifenphos (17109-49-8), (10.5) etridiazole (2593-15-9), (10.6) iodocarb (55406-53-6), (10.7) iprobenfos (26087-47-8), (10.8) isoprothiolane (50512-35-1), (10.9) propamocarb (25606-41-1), (10.10) propamocarb hydrochloride (25606-41-1), (10.11) prothiocarb (19622-08-3), (10.12) pyrazophos (13457-18-6), (10.13) quintozene (82-68-8), (10.14) tecnazene (117-18-0) and (10.15) tolclofos-methyl (57018-04-9).

(11) Inhibitors of the melanine biosynthesis, for example (11.1) carpropamid (104030-54-8), (11.2) diclocymet (139920-32-4), (11.3) fenoxanil (115852-48-7), (11.4) phthalide (27355-22-2), (11.5) pyroquilon (57369-32-1), (11.6) tricyclazole (41814-78-2) and (11.7) 2,2,2-trifluoroethyl {3-methyl-1-[(4-methylbenzoyl)amino]butan-2-yl}carbamate (851524-22-6) (WO2005042474).

(12) Inhibitors of the nucleic acid synthesis, for example (12.1) benalaxyl (71626-11-4), (12.2) benalaxyl-M (kiralaxyl) (98243-83-5), (12.3) bupirimate (41483-43-6), (12.4) clozylacon (67932-85-8), (12.5) dimethirimol (5221-53-4), (12.6) ethirimol (23947-60-6), (12.7) furalaxyl (57646-30-7), (12.8) hymexazol (10004-44-1), (12.9) metalaxyl (57837-19-1), (12.10) metalaxyl-M (mefenoxam) (70630-17-0), (12.11) ofurace (58810-48-3), (12.12) oxadixyl (77732-09-3) and (12.13) oxolinic acid (14698-29-4).

(13) Inhibitors of the signal transduction, for example (13.1) chlozolinate (84332-86-5), (13.2) fenpiclonil (74738-17-3), (13.3) fludioxonil (131341-86-1), (13.4) iprodione (36734-19-7), (13.5) procymidone (32809-16-8), (13.6) quinoxyfen (124495-18-7) and (13.7) vinclozolin (50471-44-8).

(14) Compounds capable to act as an uncoupler, for example (14.1) binapacryl (485-31-4), (14.2) dinocap (131-72-6), (14.3) ferimzone (89269-64-7), (14.4) fluazinam (79622-59-6) and (14.5) meptyldinocap (131-72-6).

(15) Further compounds, for example (15.1) benthiazole (21564-17-0), (15.2) bethoxazin (163269-30-5), (15.3) capsimycin (70694-08-5), (15.4) carvone (99-49-0), (15.5) chinomethionat (2439-01-2), (15.6) pyriofenone (chlazafenone) (688046-61-9), (15.7) cufraneb (11096-18-7), (15.8) cyflufenamid (180409-60-3), (15.9) cymoxanil (57966-95-7), (15.10) cyprosulfamide (221667-31-8), (15.11) dazomet (533-74-4), (15.12) debacarb (62732-91-6), (15.13) dichlorophen (97-23-4), (15.14) diclomezine (62865-36-5), (15.15) difenzoquat (49866-87-7), (15.16) difenzoquat methylsulfate (43222-48-6), (15.17) diphenylamine (122-39-4), (15.18) ecomate, (15.19) fenpyrazamine (473798-59-3), (15.20) flumetover (154025-04-4), (15.21) fluoroimide (41205-21-4), (15.22) flusulfamide (106917-52-6), (15.23) flutianil (304900-25-2), (15.24) fosetyl-aluminium (39148-24-8), (15.25) fosetyl-calcium, (15.26) fosetyl-sodium (39148-16-8), (15.27) hexachlorobenzene (118-74-1), (15.28) irumamycin (81604-73-1), (15.29) methasulfocarb (66952-49-6), (15.30) methyl isothiocyanate (556-61-6), (15.31) metrafenone (220899-03-6), (15.32) mildiomycin (67527-71-3), (15.33) natamycin (7681-93-8), (15.34) nickel dimethyldithiocarbamate (15521-65-0), (15.35) nitrothal-isopropyl (10552-74-6), (15.36) octhilinone (26530-20-1), (15.37) oxamocarb (917242-12-7), (15.38) oxyfenthiin (34407-87-9), (15.39) pentachlorophenol and salts (87-86-5), (15.40) phenothrin, (15.41) phosphorous acid and its salts (13598-36-2), (15.42) propamocarb-fosetylate, (15.43) propanosine-sodium (88498-02-6), (15.44) proquinazid (189278-12-4), (15.45) pyrimorph (868390-90-3), (15.45e) (2E)-3-(4-tert-butylphenyl)-3-(2-chloropyridin-4-yl)-1-(morpholin-4-yl)prop-2-en-1-one (1231776-28-5), (15.45z) (2Z)-3-(4-tert-butylphenyl)-3-(2-chloropyridin-4-yl)-1-(morpholin-4-yl)prop-2-en-1-one (1231776-29-6), (15.46) pyrrolnitrine (1018-71-9) (EP-A 1 559 320), (15.47) tebufloquin (376645-78-2), (15.48) tecloftalam (76280-91-6), (15.49) tolnifanide (304911-98-6), (15.50) triazoxide (72459-58-6), (15.51) trichlamide (70193-21-4), (15.52) zarilamid (84527-51-5), (15.53) (3S,6S,7R,8R)-8-benzyl-3-[({3-[(isobutyryloxy)methoxy]-4-methoxypyridin-2-yl}carbonyl)amino]-6-methyl-4,9-dioxo-1,5-dioxonan-7-yl 2-methylpropanoate (517875-34-2) (WO2003035617), (15.54) 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone (1003319-79-6) (WO 2008013622), (15.55) 1-(4-{4-[(5S)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone (1003319-80-9) (WO 2008013622), (15.56) 1-(4-{4-[5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone (1003318-67-9) (WO 2008013622), (15.57) 1-(4-methoxyphenoxy)-3,3-dimethylbutan-2-yl 1H-imidazole-1-carboxylate (111227-17-9), (15.58) 2,3,5,6-tetrachloro-4-(methylsulfonyl)pyridine (13108-52-6), (15.59) 2,3-dibutyl-6-chlorothieno[2,3-d]pyrimidin-4(3H)-one (221451-58-7), (15.60) 2,6-dimethyl-1H,5H-[1,4]dithiino[2,3-c:5,6-c']dipyrrole-1,3,5,7(2H,6H)-tetrone, (15.61) 2-[5-methyl-3-(trifluoromethyl)-1H-pyrazol-1-yl]-1-(4-{4-[(5R)-5-phenyl-4,5-dihydro-1,2-oxazol-3-yl]-1,3-thiazol-2-yl}piperidin-1-yl)ethanone (1003316-53-7) (WO 2008013622), (15.62)

2-[5-methyl-3-(trifluoromethyl)-1H-pyrazol-1-yl]-1-(4-{4-[(5S)-5-phenyl-4,5-dihydro-1,2-oxazol-3-yl]-1,3-thiazol-2-yl}piperidin-1-yl)ethanone (1003316-54-8) (WO 2008013622), (15.63) 2-[5-methyl-3-(trifluoromethyl)-1H-pyrazol-1-yl]-1-{4-[4-(5-phenyl-4,5-dihydro-1,2-oxazol-3-yl)-1,3-thiazol-2-yl]piperidin-1-yl}ethanone (1003316-51-5) (WO 2008013622), (15.64) 2-butoxy-6-iodo-3-propyl-4H-chromen-4-one, (15.65) 2-chloro-5-[2-chloro-1-(2,6-difluoro-4-methoxyphenyl)-4-methyl-1H-imidazol-5-yl]pyridine, (15.66) 2-phenylphenol and salts (90-43-7), (15.67) 3-(4,4,5-trifluoro-3,3-dimethyl-3,4-dihydroisoquinolin-1-yl)quinoline (861647-85-0) (WO2005070917), (15.68) 3,4,5-trichloropyridine-2,6-dicarbonitrile (17824-85-0), (15.69) 3-[5-(4-chlorophenyl)-2,3-dimethyl-1,2-oxazolidin-3-yl]pyridine, (15.70) 3-chloro-5-(4-chlorophenyl)-4-(2,6-difluorophenyl)-6-methylpyridazine, (15.71) 4-(4-chlorophenyl)-5-(2,6-difluorophenyl)-3,6-dimethylpyridazine, (15.72) 5-amino-1,3,4-thiadiazole-2-thiol, (15.73) 5-chloro-N'-phenyl-N'-(prop-2-yn-1-yl)thiophene-2-sulfonohydrazide (134-31-6), (15.74) 5-fluoro-2-[(4-fluorobenzyl)oxy]pyrimidin-4-amine (1174376-11-4) (WO2009094442), (15.75) 5-fluoro-2-[(4-methylbenzyl)oxy]pyrimidin-4-amine (1174376-25-0) (WO2009094442), (15.76) 5-methyl-6-octyl[1,2,4]triazolo[1,5-a]pyrimidin-7-amine, (15.77) ethyl (2Z)-3-amino-2-cyano-3-phenylprop-2-enoate, (15.78) N'-(4-{[3-(4-chlorobenzyl)-1,2,4-thiadiazol-5-yl]oxy}-2,5-dimethylphenyl)-N-ethyl-N-methylimidoformamide, (15.79) N-(4-chlorobenzyl)-3-[3-methoxy-4-(prop-2-yn-1-yloxy)phenyl]propanamide, (15.80) N-[(4-chlorophenyl)(cyano)methyl]-3-[3-methoxy-4-(prop-2-yn-1-yloxy)phenyl]propanamide, (15.81) N-[(5-bromo-3-chloropyridin-2-yl)methyl]-2,4-dichloropyridine-3-carboxamide, (15.82) N-[1-(5-bromo-3-chloropyridin-2-yl)ethyl]-2,4-dichloropyridine-3-carboxamide, (15.83) N-[1-(5-bromo-3-chloropyridin-2-yl)ethyl]-2-fluoro-4-iodopyridine-3-carboxamide, (15.84) N-{(E)-[(cyclopropylmethoxy)imino][6-(difluoromethoxy)-2,3-difluorophenyl]methyl}-2-phenylacetamide (221201-92-9), (15.85) N-{(Z)-[(cyclopropylmethoxy)imino][6-(difluoromethoxy)-2,3-difluorophenyl]methyl}-2-phenylacetamide (221201-92-9), (15.86) N'-{4-[(3-tert-butyl-4-cyano-1,2-thiazol-5-yl)oxy]-2-chloro-5-methylphenyl}-N-ethyl-N-methylimidoformamide, (15.87) N-methyl-2-(1-{[5-methyl-3-(trifluoromethyl)-1H-pyrazol-1-yl]acetyl}piperidin-4-yl)-N-(1,2,3,4-tetrahydronaphthalen-1-yl)-1,3-thiazole-4-carboxamide (922514-49-6) (WO 2007014290), (15.88) N-methyl-2-(1-{[5-methyl-3-(trifluoromethyl)-1H-pyrazol-1-yl]acetyl}piperidin-4-yl)-N-[(1R)-1,2,3,4-tetrahydronaphthalen-1-yl]-1,3-thiazole-4-carboxamide (922514-07-6) (WO 2007014290), (15.89) N-methyl-2-(1-{[5-methyl-3-(trifluoromethyl)-1H-pyrazol-1-yl]acetyl}piperidin-4-yl)-N-[(1S)-1,2,3,4-tetrahydronaphthalen-1-yl]-1,3-thiazole-4-carboxamide (922514-48-5) (WO 2007014290), (15.90) pentyl {6-[({[(1-methyl-1H-tetrazol-5-yl)(phenyl)methylidene]amino}oxy)methyl]pyridin-2-yl}carbamate, (15.91) phenazine-1-carboxylic acid, (15.92) quinolin-8-ol (134-31-6), (15.93) quinolin-8-ol sulfate (2:1) (134-31-6) and (15.94) tert-butyl {6-[({[(Z)-(1-methyl-1H-tetrazol-5-yl)(phenyl)methylene]amino}oxy)methyl]pyridin-2-yl}carbamate.

(16) Further compounds, for example (16.1) 1-methyl-3-(trifluoromethyl)-N-[2'-(trifluoromethyl)biphenyl-2-yl]-1H-pyrazole-4-carboxamide, (16.2) N-(4'-chlorobiphenyl-2-yl)-3-(difluoromethyl)-1-methyl-1H-pyrazole-4-carboxamide, (16.3) N-(2',4'-dichlorobiphenyl-2-yl)-3-(difluoromethyl)-1-methyl-1H-pyrazole-4-carboxamide, (16.4) 3-(difluoromethyl)-1-methyl-N-[4'-(trifluoromethyl)biphenyl-2-yl]-1H-pyrazole-4-carboxamide, (16.5) N-(2',5-difluorobiphenyl-2-yl)-1-methyl-3-(trifluoromethyl)-1H-pyrazole-4-carboxamide, (16.6) 3-(difluoromethyl)-1-methyl-N-[4'-(prop-1-yn-1-yl)biphenyl-2-yl]-1H-pyrazole-4-carboxamide (known from WO 2004/058723), (16.7) 5-fluoro-1,3-dimethyl-N-[4'-(prop-1-yn-1-yl)biphenyl-2-yl]-1H-pyrazole-4-carboxamide (known from WO 2004/058723), (16.8) 2-chloro-N-[4'-(prop-1-yn-1-yl)biphenyl-2-yl]pyridine-3-carboxamide (known from WO 2004/058723), (16.9) 3-(difluoromethyl)-N-[4'-(3,3-dimethylbut-1-yn-1-yl)biphenyl-2-yl]-1-methyl-1H-pyrazole-4-carboxamide (known from WO 2004/058723), (16.10) N-[4'-(3,3-dimethylbut-1-yn-1-yl)biphenyl-2-yl]-5-fluoro-1,3-dimethyl-1H-pyrazole-4-carboxamide (known from WO 2004/058723), (16.11) 3-(difluoromethyl)-N-(4'-ethynylbiphenyl-2-yl)-1-methyl-1H-pyrazole-4-carboxamide (known from WO 2004/058723), (16.12) N-(4'-ethynylbiphenyl-2-yl)-5-fluoro-1,3-dimethyl-1H-pyrazole-4-carboxamide (known from WO 2004/058723), (16.13) 2-chloro-N-(4'-ethynylbiphenyl-2-yl)pyridine-3-carboxamide (known from WO 2004/058723), (16.14) 2-chloro-N-[4'-(3,3-dimethylbut-1-yn-1-yl)biphenyl-2-yl]pyridine-3-carboxamide (known from WO 2004/058723), (16.15) 4-(difluoromethyl)-2-methyl-N-[4'-(trifluoromethyl)biphenyl-2-yl]-1,3-thiazole-5-carboxamide (known from WO 2004/058723), (16.16) 5-fluoro-N-[4'-(3-hydroxy-3-methylbut-1-yn-1-yl)biphenyl-2-yl]-1,3-dimethyl-1H-pyrazole-4-carboxamide (known from WO 2004/058723), (16.17) 2-chloro-N-[4'-(3-hydroxy-3-methylbut-1-yn-1-yl)biphenyl-2-yl]pyridine-3-carboxamide (known from WO 2004/058723), (16.18) 3-(difluoromethyl)-N-[4'-(3-methoxy-3-methylbut-1-yn-1-yl)biphenyl-2-yl]-1-methyl-1H-pyrazole-4-carboxamide (known from WO 2004/058723), (16.19) 5-fluoro-N-[4'-(3-methoxy-3-methylbut-1-yn-1-yl)biphenyl-2-yl]-1,3-dimethyl-1H-pyrazole-4-carboxamide (known from WO 2004/058723), (16.20) 2-chloro-N-[4'-(3-methoxy-3-methylbut-1-yn-1-yl)biphenyl-2-yl]pyridine-3-carboxamide (known from WO 2004/058723), (16.21) (5-bromo-2-methoxy-4-methylpyridin-3-yl)(2,3,4-trimethoxy-6-methylphenyl)methanone (known from EP-A 1 559 320), (16.22) N-[2-(4-{[3-(4-chlorophenyl)prop-2-yn-1-yl]oxy}-3-methoxyphenyl)ethyl]-N2-(methylsulfonyl)valinamide (220706-93-4), (16.23) 4-oxo-4-[(2-phenylethyl)amino]butanoic acid and (16.24) but-3-yn-1-yl {6-[({[(Z)-(1-methyl-1H-tetrazol-5-yl)(phenyl)methylene]amino}oxy)methyl]pyridin-2-yl}carbamate.

All named mixing partners of the classes (1) to (16) can, if their functional groups enable this, optionally form salts with suitable bases or acids.

Bactericides:

Bronopol, dichlorophen, nitrapyrin, nickel dimethyl dithiocarbamate, kasugamycin, octhilinone, furan-carboxylic acid, oxytetracyclin, probenazole, streptomycin, tecloftalam, copper sulfate and other copper preparations.

Insecticides/Acaricides/Nematicides:

(1) Acetylcholinesterase (AChE) inhibitors, for example carbamates, e.g. Alanycarb, Aldicarb, Bendiocarb, Benfuracarb, Butocarboxim, Butoxycarboxim, Carbaryl, Carbofuran, Carbosulfan, Ethiofencarb, Fenobucarb, Formetanate, Furathiocarb, Isoprocarb, Methiocarb, Methomyl, Metolcarb, Oxamyl, Pirimicarb, Propoxur, Thiodicarb, Thiofanox, Triazamate, Trimethacarb, XMC, and Xylylcarb; or organophosphates, e.g. Acephate, Azamethiphos, Azinphos-ethyl, Azinphos-methyl, Cadusafos, Chlorethoxyfos, Chlorfenvinphos, Chlormephos, Chlorpyrifos, Chlorpyrifos-methyl, Coumaphos, Cyanophos, Demeton-S-methyl, Diazinon, Dichlorvos/DDVP, Dicrotophos, Dimethoate, Dimethylvinphos, Disulfoton, EPN, Ethion, Ethoprophos, Famphur, Fenamiphos, Fenitrothion, Fenthion, Fosthiazate, Heptenophos, Imicyafos, Isofenphos, Isopropyl O-(methoxyaminothio-phosphoryl)salicylate, Isoxathion, Malathion, Mecarbam, Methamidophos, Methidathion, Mevinphos, Monocrotophos, Naled, Omethoate, Oxydemeton-methyl, Parathion, Parathion-methyl, Phenthoate, Phorate, Phosalone, Phosmet, Phosphamidon, Phoxim, Pirimiphos-methyl, Profenofos, Propetamphos, Prothiofos, Pyraclofos, Pyridaphenthion, Quinalphos, Sulfotep, Tebupirimfos, Temephos, Terbufos, Tetrachlorvinphos, Thiometon, Triazophos, Trichlorfon, and Vamidothion.

(2) GABA-gated chloride channel antagonists, for example
cyclodiene organochlorines, e.g. Chlordane and Endosulfan; or
phenylpyrazoles (fiproles), e.g. Ethiprole and Fipronil.

(3) Sodium channel modulators/voltage-dependent sodium channel blockers, for example
pyrethroids, e.g. Acrinathrin, Allethrin, d-cis-trans Allethrin, d-trans Allethrin, Bifenthrin, Bioallethrin, Bioallethrin S-cyclopentenyl isomer, Bioresmethrin, Cyloprothrin, Cyfluthrin, beta-Cyfluthrin, Cyhalothrin, lambda-Cyhalothrin, gamma-Cyhalothrin, Cypermethrin, alpha-Cypermethrin, beta-Cypermethrin, theta-Cypermethrin, zeta-Cypermethrin, Cyphenothrin [(1R)-trans isomers], Deltamethrin, Empenthrin [(EZ)-(1R) isomers), Esfenvalerate, Etofenprox, Fenpropathrin, Fenvalerate, Flucythrinate, Flumethrin, tau-Fluvalinate, Halfenprox, Imiprothrin, Kadethrin, Permethrin, Phenothrin [(1R)-trans isomer), Prallethrin, Pyrethrine (pyrethrum), Resmethrin, Silafluofen, Tefluthrin, Tetramethrin, Tetramethrin [(1R) isomers)], Tralomethrin, and Transfluthrin; or
DDT; or Methoxychlor.

(4) Nicotinic acetylcholine receptor (nAChR) agonists, for example
neonicotinoids, e.g. Acetamiprid, Clothianidin, Dinotefuran, Imidacloprid, Nitenpyram, Thiacloprid, and Thiamethoxam; or
Nicotine.

(5) Nicotinic acetylcholine receptor (nAChR) allosteric activators, for example
spinosyns, e.g. Spinetoram and Spinosad.

(6) Chloride channel activators, for example
avermectins/milbemycins, e.g. Abamectin, Emamectin benzoate, Lepimectin, and Milbemectin.

(7) Juvenile hormone mimics, for example
juvenile hormon analogues, e.g. Hydroprene, Kinoprene, and Methoprene; or
Fenoxycarb; or Pyriproxyfen.

(8) Miscellaneous non-specific (multi-site) inhibitors, for example
alkyl halides, e.g. Methyl bromide and other alkyl halides; or Chloropicrin; or Sulfuryl fluoride; or Borax; or Tartar emetic.

(9) Selective homopteran feeding blockers, e.g. Pymetrozine; or Flonicamid.

(10) Mite growth inhibitors, e.g. Clofentezine, Hexythiazox, and Diflovidazin; or
Etoxazole.

(11) Microbial disruptors of insect midgut membranes, e.g. *Bacillus thuringiensis* subspecies *israelensis*, *Bacillus sphaericus*, *Bacillus thuringiensis* subspecies *aizawai*, *Bacillus thuringiensis* subspecies *kurstaki*, *Bacillus thuringiensis* subspecies *tenebrionis*, and BT crop proteins: Cry1Ab, Cry1Ac, Cry1Fa, Cry2Ab, mCry3A, Cry3Ab, Cry3Bb, Cry34/35Ab1.

(12) Inhibitors of mitochondrial ATP synthase, for example Diafenthiuron; or
organotin miticides, e.g. Azocyclotin, Cyhexatin, and Fenbutatin oxide; or
Propargite; or Tetradifon.

(13) Uncouplers of oxidative phoshorylation via disruption of the proton gradient, for example Chlorfenapyr, DNOC, and Sulfluramid.

(14) Nicotinic acetylcholine receptor (nAChR) channel blockers, for example Bensultap, Cartap hydrochloride, Thiocyclam, and Thiosultap-sodium.

(15) Inhibitors of chitin biosynthesis, type 0, for example Bistrifluoron, Chlorfluazuron, Diflubenzuron, Flucycloxuron, Flufenoxuron, Hexaflumuron, Lufenuron, Novaluron, Noviflumuron, Teflubenzuron, and Triflumuron.

(16) Inhibitors of chitin biosynthesis, type 1, for example Buprofezin.

(17) Moulting disruptors, for example Cyromazine.

(18) Ecdysone receptor agonists, for example Chromafenozide, Halofenozide, Methoxyfenozide, and Tebufenozide.

(19) Octopamine receptor agonists, for example Amitraz.

(20) Mitochondrial complex III electron transport inhibitors, for example Hydramethylnon; or Acequinocyl; or Fluacrypyrim.

(21) Mitochondrial complex I electron transport inhibitors, for example
METI acaricides, e.g. Fenazaquin, Fenpyroximate, Pyrimidifen, Pyridaben, Tebufenpyrad, and Tolfenpyrad; or
Rotenone (Derris).

(22) Voltage-dependent sodium channel blockers, e.g. Indoxacarb; or Metaflumizone.

(23) Inhibitors of acetyl CoA carboxylase, for example
tetronic and tetramic acid derivatives, e.g. Spirodiclofen, Spiromesifen, and Spirotetramat.

(24) Mitochondrial complex IV electron transport inhibitors, for example
phosphines, e.g. Aluminium phosphide, Calcium phosphide, Phosphine, and Zinc phosphide; or Cyanide.

(25) Mitochondrial complex II electron transport inhibitors, for example Cyenopyrafen.

(28) Ryanodine receptor modulators, for example
diamides, e.g. Chlorantraniliprole and Flubendiamide.

Further active ingredients with unknown or uncertain mode of action, for example Amidoflumet, Azadirachtin, Benclothiaz, Benzoximate, Bifenazate, Bromopropylate, Chinomethionat, Cryolite, Cyantraniliprole (Cyazypyr), Cyflumetofen, Dicofol, Diflovidazin, Fluensulfone, Flufenerim, Flufiprole, Fluopyram, Fufenozide, Imidaclothiz, Iprodione, Meperfluthrin, Pyridalyl, Pyrifluquinazon, Tetramethylfluthrin, and iodomethane; furthermore products based on *Bacillus firmus* (including but not limited to strain CNCM I-1582, such as, for example, VOTiVO™, BioNem) or one of the following known active compounds: 3-bromo-N-{2-bromo-4-chloro-6-[(1-cyclopropylethyl)carbamoyl]phenyl}-1-(3-chloropyridin-2-yl)-1H-pyrazole-5-carboxamide (known from WO2005/077934), 4-{[(6-bromopyridin-3-yl)methyl](2-fluoroethyl)amino}furan-2(5H)-one (known from WO2007/115644), 4-{[(6-fluoropyridin-3-yl)methyl](2,2-difluoroethyl)amino}furan-2(5H)-one (known from WO2007/115644), 4-{[(2-chloro-1,3-thiazol-5-yl)methyl](2-fluoroethyl)amino}furan-2(5H)-one (known from WO2007/115644), 4-{[(6-chlorpyridin-3-yl)methyl](2-fluoroethyl)amino}furan-2(5H)-one (known from WO2007/115644), Flupyradifurone, 4-{[(6-chlor-5-fluoropyridin-3-yl)methyl](methyl)amino}furan-2(5H)-one (known from WO2007/115643), 4-{[(5,6-dichloropyridin-3-yl)methyl](2- fluoroethyl)amino}furan-2(5H)-one (known from WO2007/115646), 4-{[(6-chloro-5-fluoropyridin-3-yl)methyl](cyclopropyl)amino}furan-2(5H)-one (known from WO2007/115643), 4-{[(6-chloropyridin-3-yl)methyl](cyclopropyl)amino}furan-2(5H)-one (known from EP-A-0 539 588), 4-{[(6-chlorpyridin-3-yl)methyl](methyl)amino}furan-2(5H)-one (known from EP-A-0 539 588), {[1-(6-chloropyridin-3-yl)ethyl](methyl)oxido-λ$^4$-sulfanylidene}cyanamide (known from WO2007/149134) and its diastereomers {[(1R)-1-(6-chloropyridin-3-yl)ethyl]methyl)oxido-λ$^4$-sulfanylidene}cyanamide (A) and {[(1S)-1-(6-chloropyridin-3-yl)ethyl]methyl)oxido-λ$^4$-sulfanylidene}cyanamide (B) (also known from WO2007/149134) as well as Sulfoxaflor and its diastereomers [(R)-methyl(oxido){(1R)-1-[6-(trifluoromethyl)pyridin-3-yl]ethyl}-λ$^4$-sulfanylidene]cyanamide (A1) and [(S)-methyl(oxido){(1S)-1-[6-(trifluoromethyl)pyridin-3-yl]ethyl}-λ$^4$-sulfanylidene]cyanamide (A2), referred to as group of diastereomers A (known from WO2010/074747, WO2010/074751), [(R)-methyl(oxido){(1S)-1-[6-(trifluoromethyl)pyridin-3-yl]ethyl}-λ$^4$-sulfanylidene]cyanamide (B1) and [(S)-methyl(oxido){(1R)-1-[6-(trifluoromethyl)pyridin-3-yl]ethyl}-λ$^4$-sulfanylidene]cyanamide (B2), referred to as group of diastereomers B (also known from WO2010/074747, WO2010/074751), and 11-(4-chloro-2,6-dimethylphenyl)-12-hydroxy-1,4-dioxa-9-azadispiro[4.2.4.2]tetradec-11-en-10-one (known from WO2006/089633), 3-(4'-fluoro-2,4-dimethylbiphenyl-3-yl)-4-hydroxy-8-oxa-1-azaspiro[4.5]dec-3-en-2-one (known from WO2008/067911), 1-{2-fluoro-4-methyl-5-[(2,2,2-trifluoroethyl)sulfinyl]phenyl}-3-(trifluoromethyl)-1H-1,2,4-triazol-5-amine (known from WO2006/043635), [(3S,4aR,12R,12aS,12bS)-3-[(cyclopropylcarbonyl)oxy]-6,12-dihydroxy-4,12b-dimethyl-11-oxo-9-(pyridin-3-yl)-1,3,4,4a,5,6,6a,12,12a,12b-decahydro-2H,11H-benzo[f]pyrano[4,3-b]chromen-4-yl]methyl cyclopropanecarboxylate (known from WO2008/066153), 2-cyano-3-(difluoromethoxy)-N,N-dimethylbenzenesulfonamide (known from WO2006/056433), 2-cyano-3-(difluoromethoxy)-N-methylbenzenesulfonamide (known from WO2006/100288), 2-cyano-3-(difluoromethoxy)-N-ethyl-benzenesulfonamide (known from WO2005/035486), 4-(difluoromethoxy)-N-ethyl-N-methyl-1,2-benzothiazol-3-amine 1,1-dioxide (known from WO2007/057407), N-[1-(2,3-dimethylphenyl)-2-(3,5-dimethylphenyl)ethyl]-4,5-dihydro-1,3-thiazol-2-amine (known from WO2008/104503), {1-[(2E)-3-(4-chlorophenyl)prop-2-en-1-yl]-5-fluorospiro[indole-3,4'-piperidin]-1(2H)-yl}(2-chloropyridin-4-yl)methanone (known from WO2003/106457), 3-(2,5-dimethylphenyl)-4-hydroxy-8-methoxy-1,8-diazaspiro[4.5]dec-3-en-2-one (known from WO2009/049851), 3-(2,5-dimethylphenyl)-8-methoxy-2-oxo-1,8-diazaspiro[4.5]dec-3-en-4-ylethyl carbonate (known from WO2009/049851), 4-(but-2-yn-1-yloxy)-6-(3,5-dimethylpiperidin-1-yl)-5-fluoropyrimidine (known from WO2004/099160), (2,2,3,3,4,4,5,5-octafluoropentyl)(3,3,3-trifluoropropyl)malononitrile (known from WO2005/063094), (2,2,3,3,4,4,5,5-octafluoropentyl)(3,3,4,4,4-pentafluorobutyl)malononitrile (known from WO2005/063094), 8-[2-(cyclopropylmethoxy)-4-(trifluoromethyl)phenoxy]-3-[6-(trifluoromethyl)pyridazin-3-yl]-3-azabicyclo[3.2.1]octane (known from WO2007/040280), Flometoquin, PF1364 (CAS-Reg.No. 1204776-60-2) (known from JP2010/018586), 5-[5-(3,5-dichlorophenyl)-5-(trifluoromethyl)-4,5-dihydro-1,2-oxazol-3-yl]-2-(1H-1,2,4-triazol-1-yl)benzonitrile (known from WO2007/075459), 5-[5-(2-chloropyridin-4-yl)-5-(trifluoromethyl)-4,5-dihydro-1,2-oxazol-3-yl]-2-(1H-1,2,4-triazol-1-yl)benzonitrile (known from WO2007/075459), 4-[5-(3,5-dichlorophenyl)-5-(trifluoromethyl)-4,5-dihydro-1,2-oxazol-3-yl]-2-methyl-N-{2-oxo-2-[(2,2,2-trifluoroethyl)amino]ethyl}benzamide (known from WO2005/085216), 4-{[(6-chloropyridin-3-yl)methyl](cyclopropyl)amino}-1,3-oxazol-2(5H)-one, 4-{[(6-chloropyridin-3-yl)methyl](2,2-difluoroethyl)amino}-1,3-oxazol-2(5H)-one, 4-{[(6-chloropyridin-3-yl)methyl](ethyl)amino}-1,3-oxazol-2(5H)-one, 4-{[(6-chloropyridin-3-yl)methyl](methyl)amino}-1,3-oxazol-2(5H)-one (all known from WO2010/005692), NNI-0711 (known from WO2002/096882), 1-acetyl-N-[4-(1,1,1,3,3,3-hexafluoro-2-methoxypropan-2-yl)-3-isobutylphenyl]-N-isobutyryl-3,5-dimethyl-1H-pyrazole-4-carboxamide (known from WO2002/096882), methyl 2-[2-({[3-bromo-1-(3-chloropyridin-2-yl)-1H-pyrazol-5-yl]carbonyl}amino)-5-chloro-3-methylbenzoyl]-2-methylhydrazinecarboxylate (known from WO2005/085216), methyl 2-[2-({[3-bromo-1-(3-chloropyridin-2-yl)-1H-pyrazol-5-yl]carbonyl}amino)-5-cyano-3-methylbenzoyl]-2-ethylhydrazinecarboxylate (known from WO2005/085216), methyl 2-[2-({[3-bromo-1-(3-chloropyridin-2-yl)-1H-pyrazol-5-yl]carbonyl}amino)-5-cyano-3-methylbenzoyl]-2-methylhydrazinecarboxylate (known from WO2005/085216), methyl 2-[3,5-dibromo-2-({[3-bromo-1-(3-chloropyridin-2-yl)-1H-pyrazol-5-yl]carbonyl}amino)benzoyl]-1,2-diethylhydrazinecarboxylate (known from WO2005/085216), methyl 2-[3,5-dibromo-2-({[3-bromo-1-(3-chloropyridin-2-yl)-1H-pyrazol-5-yl]carbonyl}amino)benzoyl]-2-ethylhydrazinecarboxylate (known from WO2005/085216), (5RS,7RS;5RS,7SR)-1-(6-chloro-3-pyridylmethyl)-1,2,3,5,6,7-hexahydro-7-methyl-8-nitro-5-propoxyimidazo[1,2-a]pyridine (known from WO2007/101369), 2-{6-[2-(5-fluoropyridin-3-yl)-1,3-thiazol-5-yl]pyridin-2-yl}pyrimidine (known from WO2010/006713), 2-{6-[2-(pyridin-3-yl)-1,3-thiazol-5-yl]pyridin-2-yl}pyrimidine (known from WO2010/006713), 1-(3-chloropyridin-2-yl)-N-[4-cyano-2-methyl-6-(methylcarbamoyl)phenyl]-3-{[5-(trifluoromethyl)-1H-tetrazol-1-yl]methyl}-1H-pyrazole-5-carboxamide (known from WO2010/069502), 1-(3-chloropyridin-2-yl)-N-[4-cyano-2-methyl-6-(methylcarbamoyl)phenyl]-3-{[5-(trifluoromethyl)-2H-tetrazol-2-yl]methyl}-1H-pyrazole-5-carboxamide (known from WO2010/069502), N-[2-(tert-butylcarbamoyl)-4-cyano-6-methylphenyl]-1-(3-chloropyridin-2-yl)-3-{[5-(trifluoromethyl)-1H-tetrazol-1-yl]methyl}-1H-pyrazole-5-carboxamide (known from WO2010/069502), N-[2-(tert-butylcarbamoyl)-4-cyano-6-methylphenyl]-1-(3-chloropyridin-2-yl)-3-{[5-(trifluoromethyl)-2H-tetrazol-2-yl]methyl}-1H-pyrazole-5-carboxamide (known from WO2010/069502), (1E)-N-[(6-chloropyridin-3-yl)methyl]-N'-cyano-N-(2,2-difluoroethyl)ethanimidamide (known from WO2008/009360), N-[2-(5-amino-1,3,4-thiadiazol-2-yl)-4-chloro-6-methylphenyl]-3-bromo-1-(3-chloropyridin-2-yl)-1H-pyrazole-5-carboxamide (known from CN102057925), and methyl 2-[3,5-dibromo-2-({[3-bromo-1-(3-chloropyridin-2-yl)-1H-pyrazol-5-yl]carbonyl}amino)benzoyl]-2-ethyl-1-methylhydrazinecarboxylate (known from WO2011/049233).

A mixture with other known active compounds such as herbicides, or with fertilizers and growth regulators, safeners or semiochemicals is also possible.

In addition, the compounds of the formula (I) according to the invention also have very good antimycotic activity. They have a very broad antimycotic spectrum of action, in particular against dermatophytes and budding fungi, moulds and diphasic fungi (for example against *Candida* species such as *Candida albicans, Candida glabrata*) and *Epidermophyton*

*floccosum*, *Aspergillus* species such as *Aspergillus niger* and *Aspergillus fumigatus*, *Trichophyton* species such as *Trichophyton mentagrophytes*, *Microsporon* species such as *Microsporon canis* and *audouinii*. The enumeration of these fungi is no restriction whatsoever of the mycotic spectrum which can be controlled and is provided by illustration only.

The active compounds can be employed as such, in the form of their formulations or the use forms prepared therefrom, such as ready-to-use solutions, suspensions, wettable powders, pastes, soluble powders, dusts and granules. They are applied in the customary manner, for example by pouring, spraying, atomizing, broadcasting, dusting, foaming, painting on and the like. It is furthermore possible to apply the active compounds by the ultra-low-volume method, or to inject the active compound preparation or the active compound itself into the soil. The seed of the plants can also be treated.

When employing the active compounds according to the invention as fungicides, the application rates can be varied within a substantial range, depending on the type of application. In the treatment of plant parts, the application rates of active compound are generally between 0.1 and 10 000 g/ha, preferably between 10 and 1000 g/ha. For the treatment of seed, the application rates of active compound are generally between 0.001 and 50 g per kilogram of seed, preferably between 0.01 and 10 g per kilogram of seed. For treating the soil, the application rates of active compound are generally between 0.1 and 10 000 g/ha, preferably between 1 and 5000 g/ha.

According to the invention all plants and plant parts can be treated. By plants is meant all plants and plant populations such as desirable and undesirable wild plants, cultivars and plant varieties (whether or not protectable by plant variety or plant breeder's rights). Cultivars and plant varieties can be plants obtained by conventional propagation and breeding methods which can be assisted or supplemented by one or more biotechnological methods such as by use of double haploids, protoplast fusion, random and directed mutagenesis, molecular or genetic markers or by bioengineering and genetic engineering methods. By plant parts is meant all above ground and below ground parts and organs of plants such as shoot, leaf, blossom and root, whereby for example leaves, needles, stems, branches, blossoms, fruiting bodies, fruits and seed as well as roots, corms and rhizomes are listed. Crops and vegetative and generative propagating material, for example cuttings, corms, rhizomes, runners and seeds also belong to plant parts.

Among the plants that can be protected by the method according to the invention, mention may be made of major field crops like corn, soybean, cotton, *Brassica* oilseeds such as *Brassica napus* (e.g. canola), *Brassica rapa*, *B. juncea* (e.g. mustard) and *Brassica carinata*, rice, wheat, sugarbeet, sugarcane, oats, rye, barley, millet, triticale, flax, vine and various fruits and vegetables of various botanical taxa such as *Rosaceae* sp. (for instance pip fruit such as apples and pears, but also stone fruit such as apricots, cherries, almonds and peaches, berry fruits such as strawberries), *Ribesioidae* sp., *Juglandaceae* sp., *Betulaceae* sp., *Anacardiaceae* sp., *Fagaceae* sp., *Moraceae* sp., *Oleaceae* sp., *Actimidaceae* sp., *Lauraceae* sp., *Musaceae* sp. (for instance banana trees and plantings), *Rubiaceae* sp. (for instance coffee), *Theaceae* sp., *Sterculiceae* sp., *Rutaceae* sp. (for instance lemons, oranges and grapefruit); *Solanaceae* sp. (for instance tomatoes, potatoes, peppers, eggplant), *Liliaceae* sp., *Compositiae* sp. (for instance lettuce, artichoke and chicory—including root chicory, endive or common chicory), *Umbelliferae* sp. (for instance carrot, parsley, celery and celeriac), *Cucurbitaceae* sp. (for instance cucumber—including pickling cucumber, squash, watermelon, gourds and melons), *Affiaceae* sp. (for instance onions and leek), *Cruciferae* sp. (for instance white cabbage, red cabbage, broccoli, cauliflower, brussel sprouts, pak choi, kohlrabi, radish, horseradish, cress, Chinese cabbage), *Leguminosae* sp. (for instance peanuts, peas and beans beans—such as climbing beans and broad beans), *Chenopodiaceae* sp. (for instance mangold, spinach beet, spinach, beetroots), *Malvaceae* (for instance okra), *Asparagaceae* (for instance asparagus); horticultural and forest crops; ornamental plants; as well as genetically modified homologues of these crops.

The method of treatment according to the invention can be used in the treatment of genetically modified organisms (GMOs), e.g. plants or seeds. Genetically modified plants (or transgenic plants) are plants of which a heterologous gene has been stably integrated into genome. The expression "heterologous gene" essentially means a gene which is provided or assembled outside the plant and when introduced in the nuclear, chloroplastic or mitochondrial genome gives the transformed plant new or improved agronomic or other properties by expressing a protein or polypeptide of interest or by downregulating or silencing other gene(s) which are present in the plant (using for example, antisense technology, cosuppression technology or RNA interference—RNAi-technology). A heterologous gene that is located in the genome is also called a transgene. A transgene that is defined by its particular location in the plant genome is called a transformation or transgenic event.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the active compounds and compositions which can be used according to the invention, better plant growth, increased tolerance to high or low temperatures, increased tolerance to drought or to water or soil salt content, increased flowering performance, easier harvesting, accelerated maturation, higher harvest yields, bigger fruits, larger plant height, greener leaf color, earlier flowering, higher quality and/or a higher nutritional value of the harvested products, higher sugar concentration within the fruits, better storage stability and/or processability of the harvested products are possible, which exceed the effects which were actually to be expected.

At certain application rates, the active compound combinations according to the invention may also have a strengthening effect in plants. Accordingly, they are also suitable for mobilizing the defense system of the plant against attack by unwanted microorganisms. This may, if appropriate, be one of the reasons of the enhanced activity of the combinations according to the invention, for example against fungi. Plant-strengthening (resistance-inducing) substances are to be understood as meaning, in the present context, those substances or combinations of substances which are capable of stimulating the defense system of plants in such a way that, when subsequently inoculated with unwanted microorganisms, the treated plants display a substantial degree of resistance to these microorganisms. In the present case, unwanted microorganisms are to be understood as meaning phytopathogenic fungi, bacteria and viruses. Thus, the substances according to the invention can be employed for protecting plants against attack by the abovementioned pathogens within a certain period of time after the treatment. The period of time within which protection is effected generally extends from 1 to 10 days, preferably 1 to 7 days, after the treatment of the plants with the active compounds.

Plants and plant cultivars which are preferably to be treated according to the invention include all plants which have genetic material which impart particularly advantageous, useful traits to these plants (whether obtained by breeding and/or biotechnological means).

Plants and plant cultivars which are also preferably to be treated according to the invention are resistant against one or more biotic stresses, i.e. said plants show a better defense against animal and microbial pests, such as against nematodes, insects, mites, phytopathogenic fungi, bacteria, viruses and/or viroids.

Examples of nematode resistant plants are described in e.g. U.S. patent application Ser. Nos. 11/765,491, 11/765,494, 10/926,819, 10/782,020, 12/032,479, 10/783,417, 10/782, 096, 11/657,964, 12/192,904, 11/396,808, 12/166,253, 12/166,239, 12/166,124, 12/166,209, 11/762,886, 12/364, 335, 11/763,947, 12/252,453, 12/209,354, 12/491,396 or 12/497,221.

Plants and plant cultivars which may also be treated according to the invention are those plants which are resistant to one or more abiotic stresses. Abiotic stress conditions may include, for example, drought, cold temperature exposure, heat exposure, osmotic stress, flooding, increased soil salinity, increased mineral exposure, ozone exposure, high light exposure, limited availability of nitrogen nutrients, limited availability of phosphorus nutrients, shade avoidance.

Plants and plant cultivars which may also be treated according to the invention, are those plants characterized by enhanced yield characteristics. Increased yield in said plants can be the result of, for example, improved plant physiology, growth and development, such as water use efficiency, water retention efficiency, improved nitrogen use, enhanced carbon assimilation, improved photosynthesis, increased germination efficiency and accelerated maturation. Yield can furthermore be affected by improved plant architecture (under stress and non-stress conditions), including but not limited to, early flowering, flowering control for hybrid seed production, seedling vigor, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content, protein content, oil content and composition, nutritional value, reduction in anti-nutritional compounds, improved processability and better storage stability.

Examples of plants with the above-mentioned traits are non-exhaustively listed in Table A.

Plants that may be treated according to the invention are hybrid plants that already express the characteristic of heterosis or hybrid vigor which results in generally higher yield, vigor, health and resistance towards biotic and abiotic stresses). Such plants are typically made by crossing an inbred male-sterile parent line (the female parent) with another inbred male-fertile parent line (the male parent). Hybrid seed is typically harvested from the male sterile plants and sold to growers. Male sterile plants can sometimes (e.g. in corn) be produced by detasseling, i.e. the mechanical removal of the male reproductive organs (or males flowers) but, more typically, male sterility is the result of genetic determinants in the plant genome. In that case, and especially when seed is the desired product to be harvested from the hybrid plants it is typically useful to ensure that male fertility in the hybrid plants is fully restored. This can be accomplished by ensuring that the male parents have appropriate fertility restorer genes which are capable of restoring the male fertility in hybrid plants that contain the genetic determinants responsible for male-sterility. Genetic determinants for male sterility may be located in the cytoplasm. Examples of cytoplasmic male sterility (CMS) were for instance described in *Brassica* species (WO 92/05251, WO 95/09910, WO 98/27806, WO 05/002324, WO 06/021972 and U.S. Pat. No. 6,229,072). However, genetic determinants for male sterility can also be located in the nuclear genome. Male sterile plants can also be obtained by plant biotechnology methods such as genetic engineering. A particularly useful means of obtaining male-sterile plants is described in WO 89/10396 in which, for example, a ribonuclease such as barnase is selectively expressed in the tapetum cells in the stamens. Fertility can then be restored by expression in the tapetum cells of a ribonuclease inhibitor such as barstar (e.g. WO 91/02069).

Plants or plant cultivars (obtained by plant biotechnology methods such as genetic engineering) which may be treated according to the invention are herbicide-tolerant plants, i.e. plants made tolerant to one or more given herbicides. Such plants can be obtained either by genetic transformation, or by selection of plants containing a mutation imparting such herbicide tolerance.

Herbicide-resistant plants are for example glyphosate-tolerant plants, i.e. plants made tolerant to the herbicide glyphosate or salts thereof. Plants can be made tolerant to glyphosate through different means. For example, glyphosate-tolerant plants can be obtained by transforming the plant with a gene encoding the enzyme 5-enolpyruvylshikimate-3-phosphate synthase (EPSPS). Examples of such EPSPS genes are the AroA gene (mutant CT7) of the bacterium *Salmonella typhimurium* (Comai et al., 1983, Science 221, 370-371), the CP4 gene of the bacterium *Agrobacterium* sp. (Barry et al., 1992, Curr. Topics Plant Physiol. 7, 139-145), the genes encoding a Petunia EPSPS (Shah et al., 1986, Science 233, 478-481), a Tomato EPSPS (Gasser et al., 1988, J. Biol. Chem. 263, 4280-4289), or an *Eleusine* EPSPS (WO 01/66704). It can also be a mutated EPSPS as described in for example EP 0837944, WO 00/66746, WO 00/66747 or WO02/26995. Glyphosate-tolerant plants can also be obtained by expressing a gene that encodes a glyphosate oxido-reductase enzyme as described in U.S. Pat. Nos. 5,776,760 and 5,463,175. Glyphosate-tolerant plants can also be obtained by expressing a gene that encodes a glyphosate acetyl transferase enzyme as described in for example WO 02/36782, WO 03/092360, WO 05/012515 and WO 07/024,782. Glyphosate-tolerant plants can also be obtained by selecting plants containing naturally-occurring mutations of the above-mentioned genes, as described in for example WO 01/024615 or WO 03/013226. Plants expressing EPSPS genes that confer glyphosate tolerance are described in e.g. U.S. patent application Ser. Nos. 11/517,991, 10/739,610, 12/139,408, 12/352,532, 11/312, 866, 11/315,678, 12/421,292, 11/400,598, 11/651,752, 11/681,285, 11/605,824, 12/468,205, 11/760,570, 11/762, 526, 11/769,327, 11/769,255, 11/943,801 or 12/362,774. Plants comprising other genes that confer glyphosate tolerance, such as decarboxylase genes, are described in e.g. U.S. patent application Ser. Nos. 11/588,811, 11/185,342, 12/364, 724, 11/185,560 or 12/423,926.

Other herbicide resistant plants are for example plants that are made tolerant to herbicides inhibiting the enzyme glutamine synthase, such as bialaphos, phosphinothricin or glufosinate. Such plants can be obtained by expressing an enzyme detoxifying the herbicide or a mutant glutamine synthase enzyme that is resistant to inhibition, e.g. described in U.S. patent application Ser. No. 11/760,602. One such efficient detoxifying enzyme is an enzyme encoding a phosphinothricin acetyltransferase (such as the bar or pat protein from *Streptomyces* species). Plants expressing an exogenous phosphinothricin acetyltransferase are for example described in U.S. Pat. Nos. 5,561,236; 5,648,477; 5,646,024; 5,273,894; 5,637,489; 5,276,268; 5,739,082; 5,908,810 and 7,112,665.

Further herbicide-tolerant plants are also plants that are made tolerant to the herbicides inhibiting the enzyme hydroxyphenylpyruvatedioxygenase (HPPD). Hydroxyphenylpyruvatedioxygenases are enzymes that catalyze the reaction in which para-hydroxyphenylpyruvate (HPP) is transformed into homogentisate. Plants tolerant to HPPD-inhibitors can be transformed with a gene encoding a naturally-occurring resistant HPPD enzyme, or a gene encoding a mutated or chimeric HPPD enzyme as described in WO 96/38567, WO 99/24585, WO 99/24586, WO 2009/144079, WO 2002/046387, or U.S. Pat. No. 6,768,044. Tolerance to HPPD-inhibitors can also be obtained by transforming plants with genes encoding certain enzymes enabling the formation of homogentisate despite the inhibition of the native HPPD enzyme by the HPPD-inhibitor. Such plants and genes are described in WO 99/34008 and WO 02/36787. Tolerance of plants to HPPD inhibitors can also be improved by transforming plants with a gene encoding an enzyme having prephenate deshydrogenase (PDH) activity in addition to a gene encoding an HPPD-tolerant enzyme, as described in WO 2004/024928. Further, plants can be made more tolerant to HPPD-inhibitor herbicides by adding into their genome a gene encoding an enzyme capable of metabolizing or degrading HPPD inhibitors, such as the CYP450 enzymes shown in WO 2007/103567 and WO 2008/150473.

Still further herbicide resistant plants are plants that are made tolerant to acetolactate synthase (ALS) inhibitors. Known ALS-inhibitors include, for example, sulfonylurea, imidazolinone, triazolopyrimidines, pryimidinyoxy(thio)benzoates, and/or sulfonylaminocarbonyltriazolinone herbicides. Different mutations in the ALS enzyme (also known as acetohydroxyacid synthase, AHAS) are known to confer tolerance to different herbicides and groups of herbicides, as described for example in Tranel and Wright (2002, Weed Science 50:700-712), but also, in U.S. Pat. Nos. 5,605,011, 5,378,824, 5,141,870, and 5,013,659. The production of sulfonylurea-tolerant plants and imidazolinone-tolerant plants is described in U.S. Pat. Nos. 5,605,011; 5,013,659; 5,141,870; 5,767,361; 5,731,180; 5,304,732; 4,761,373; 5,331,107; 5,928,937; and 5,378,824; and international publication WO 96/33270. Other imidazolinone-tolerant plants are also described in for example WO 2004/040012, WO 2004/106529, WO 2005/020673, WO 2005/093093, WO 2006/007373, WO 2006/015376, WO 2006/024351, and WO 2006/060634. Further sulfonylurea- and imidazolinone-tolerant plants are also described in for example WO 07/024,782 and U.S. Patent Application No. 61/288,958.

Other plants tolerant to imidazolinone and/or sulfonylurea can be obtained by induced mutagenesis, selection in cell cultures in the presence of the herbicide or mutation breeding as described for example for soybeans in U.S. Pat. No. 5,084,082, for rice in WO 97/41218, for sugar beet in U.S. Pat. No. 5,773,702 and WO 99/057965, for lettuce in U.S. Pat. No. 5,198,599, or for sunflower in WO 01/065922.

Plants or plant cultivars (obtained by plant biotechnology methods such as genetic engineering) which may also be treated according to the invention are insect-resistant transgenic plants, i.e. plants made resistant to attack by certain target insects. Such plants can be obtained by genetic transformation, or by selection of plants containing a mutation imparting such insect resistance.

An "insect-resistant transgenic plant", as used herein, includes any plant containing at least one transgene comprising a coding sequence encoding:

1) an insecticidal crystal protein from *Bacillus thuringiensis* or an insecticidal portion thereof, such as the insecticidal crystal proteins listed by Crickmore et al. (1998, Microbiology and Molecular Biology Reviews, 62: 807-813), updated by Crickmore et al. (2005) at the *Bacillus thuringiensis* toxin nomenclature, online at: http://www.lifesci.sussex.ac.uk/Home/Neil_Crickmore/Bt/), or insecticidal portions thereof, e.g., proteins of the Cry protein classes Cry1Ab, Cry1Ac, Cry1B, Cry1C, Cry1D, Cry1F, Cry2Ab, Cry3Aa, or Cry3Bb or insecticidal portions thereof (e.g. EP 1999141 and WO 2007/107302), or such proteins encoded by synthetic genes as e.g. described in and U.S. patent application Ser. No. 12/249,016; or 2) a crystal protein from *Bacillus thuringiensis* or a portion thereof which is insecticidal in the presence of a second other crystal protein from *Bacillus thuringiensis* or a portion thereof, such as the binary toxin made up of the Cry34 and Cry35 crystal proteins (Moellenbeck et al. 2001, Nat. Biotechnol. 19: 668-72; Schnepf et al. 2006, Applied Environm. Microbiol. 71, 1765-1774) or the binary toxin made up of the Cry1A or Cry1F proteins and the Cry2Aa or Cry2Ab or Cry2Ae proteins (U.S. patent application Ser. No. 12/214,022 and EP 08010791.5); or 3) a hybrid insecticidal protein comprising parts of different insecticidal crystal proteins from *Bacillus thuringiensis*, such as a hybrid of the proteins of 1) above or a hybrid of the proteins of 2) above, e.g., the Cry1A.105 protein produced by corn event MON89034 (WO 2007/027777); or 4) a protein of any one of 1) to 3) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation, such as the Cry3Bb1 protein in corn events MON863 or MON88017, or the Cry3A protein in corn event MIR604; or 5) an insecticidal secreted protein from *Bacillus thuringiensis* or *Bacillus cereus*, or an insecticidal portion thereof, such as the vegetative insecticidal (VIP) proteins listed at: http://www.lifesci.sussex.ac.uk/home/Neil_Crickmore/Bt/vip.html, e.g., proteins from the VIP3Aa protein class; or 6) a secreted protein from *Bacillus thuringiensis* or *Bacillus cereus* which is insecticidal in the presence of a second secreted protein from *Bacillus thuringiensis* or *B. cereus*, such as the binary toxin made up of the VIP1A and VIP2A proteins (WO 94/21795); or 7) a hybrid insecticidal protein comprising parts from different secreted proteins from *Bacillus thuringiensis* or *Bacillus cereus*, such as a hybrid of the proteins in 1) above or a hybrid of the proteins in 2) above; or 8) a protein of any one of 5) to 7) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation (while still encoding an insecticidal protein), such as the VIP3Aa protein in cotton event COT102; or 9) a secreted protein from *Bacillus thuringiensis* or *Bacillus cereus* which is insecticidal in the presence of a crystal protein from *Bacillus thuringiensis*, such as the binary toxin made up of VIP3 and Cry1A or Cry1F (U.S. Patent Appl. No. 61/126,083 and 61/195,019), or the binary toxin made up of the VIP3 protein and the Cry2Aa or Cry2Ab or Cry2Ae proteins (U.S. patent application Ser. No. 12/214,022 and EP 08010791.5).

10) a protein of 9) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation (while still encoding an insecticidal protein)

Of course, an insect-resistant transgenic plant, as used herein, also includes any plant comprising a combination of genes encoding the proteins of any one of the above classes 1 to 10. In one embodiment, an insect-resistant plant contains more than one transgene encoding a protein of any one of the above classes 1 to 10, to expand the range of target insect species affected when using different proteins directed at different target insect species, or to delay insect resistance development to the plants by using different proteins insecticidal to the same target insect species but having a different mode of action, such as binding to different receptor binding sites in the insect.

An "insect-resistant transgenic plant", as used herein, further includes any plant containing at least one transgene comprising a sequence producing upon expression a double-stranded RNA which upon ingestion by a plant insect pest inhibits the growth of this insect pest, as described e.g. in WO 2007/080126, WO 2006/129204, WO 2007/074405, WO 2007/080127 and WO 2007/035650.

Plants or plant cultivars (obtained by plant biotechnology methods such as genetic engineering) which may also be treated according to the invention are tolerant to abiotic stresses. Such plants can be obtained by genetic transformation, or by selection of plants containing a mutation imparting such stress resistance. Particularly useful stress tolerance plants include:

1) plants which contain a transgene capable of reducing the expression and/or the activity of poly(ADP-ribose) polymerase (PARP) gene in the plant cells or plants as described in WO 00/04173, WO/2006/045633, EP 04077984.5, or EP 06009836.5.
2) plants which contain a stress tolerance enhancing transgene capable of reducing the expression and/or the activity of the PARG encoding genes of the plants or plants cells, as described e.g. in WO 2004/090140.
3) plants which contain a stress tolerance enhancing transgene coding for a plant-functional enzyme of the nicotineamide adenine dinucleotide salvage synthesis pathway including nicotinamidase, nicotinate phosphoribosyltransferase, nicotinic acid mononucleotide adenyl transferase, nicotinamide adenine dinucleotide synthetase or nicotine amide phosphorybosyltransferase as described e.g. in EP 04077624.7, WO 2006/133827, PCT/EP07/002,433, EP 1999263, or WO 2007/107326.

Plants or plant cultivars (obtained by plant biotechnology methods such as genetic engineering) which may also be treated according to the invention show altered quantity, quality and/or storage-stability of the harvested product and/or altered properties of specific ingredients of the harvested product such as:

1) transgenic plants which synthesize a modified starch, which in its physical-chemical characteristics, in particular the amylose content or the amylose/amylopectin ratio, the degree of branching, the average chain length, the side chain distribution, the viscosity behaviour, the gelling strength, the starch grain size and/or the starch grain morphology, is changed in comparison with the synthesised starch in wild type plant cells or plants, so that this is better suited for special applications. Said transgenic plants synthesizing a modified starch are disclosed, for example, in EP 0571427, WO 95/04826, EP 0719338, WO 96/15248, WO 96/19581, WO 96/27674, WO 97/11188, WO 97/26362, WO 97/32985, WO 97/42328, WO 97/44472, WO 97/45545, WO 98/27212, WO 98/40503, WO99/58688, WO 99/58690, WO 99/58654, WO 00/08184, WO 00/08185, WO 00/08175, WO 00/28052, WO 00/77229, WO 01/12782, WO 01/12826, WO 02/101059, WO 03/071860, WO 2004/056999, WO 2005/030942, WO 2005/030941, WO 2005/095632, WO 2005/095617, WO 2005/095619, WO 2005/095618, WO 2005/123927, WO 2006/018319, WO 2006/103107, WO 2006/108702, WO 2007/009823, WO 00/22140, WO 2006/063862, WO 2006/072603, WO 02/034923, EP 06090134.5, EP 06090228.5, EP 06090227.7, EP 07090007.1, EP 07090009.7, WO 01/14569, WO 02/79410, WO 03/33540, WO 2004/078983, WO 01/19975, WO 95/26407, WO 96/34968, WO 98/20145, WO 99/12950, WO 99/66050, WO 99/53072, U.S. Pat. No. 6,734,341, WO 00/11192, WO 98/22604, WO 98/32326, WO 01/98509, WO 01/98509, WO 2005/002359, U.S. Pat. No. 5,824,790, U.S. Pat. No. 6,013,861, WO 94/04693, WO 94/09144, WO 94/11520, WO 95/35026, WO 97/20936

2) transgenic plants which synthesize non starch carbohydrate polymers or which synthesize non starch carbohydrate polymers with altered properties in comparison to wild type plants without genetic modification. Examples are plants producing polyfructose, especially of the inulin and levan-type, as disclosed in EP 0663956, WO 96/01904, WO 96/21023, WO 98/39460, and WO 99/24593, plants producing alpha-1,4-glucans as disclosed in WO 95/31553, US 2002031826, U.S. Pat. No. 6,284,479, U.S. Pat. No. 5,712,107, WO 97/47806, WO 97/47807, WO 97/47808 and WO 00/14249, plants producing alpha-1,6 branched alpha-1,4-glucans, as disclosed in WO 00/73422, plants producing alternan, as disclosed in e.g. WO 00/47727, WO 00/73422, EP 06077301.7, U.S. Pat. No. 5,908,975 and EP 0728213, 3) transgenic plants which produce hyaluronan, as for example disclosed in WO 2006/032538, WO 2007/039314, WO 2007/039315, WO 2007/039316, JP 2006304779, and WO 2005/012529.

4) transgenic plants or hybrid plants, such as onions with characteristics such as 'high soluble solids content', 'low pungency' (LP) and/or 'long storage' (LS), as described in U.S. patent application Ser. No. 12/020,360 and 61/054,026.

Plants or plant cultivars (that can be obtained by plant biotechnology methods such as genetic engineering) which may also be treated according to the invention are plants, such as cotton plants, with altered fiber characteristics. Such plants can be obtained by genetic transformation, or by selection of plants contain a mutation imparting such altered fiber characteristics and include:

a) Plants, such as cotton plants, containing an altered form of cellulose synthase genes as described in WO 98/00549
b) Plants, such as cotton plants, containing an altered form of rsw2 or rsw3 homologous nucleic acids as described in WO 2004/053219
c) Plants, such as cotton plants, with increased expression of sucrose phosphate synthase as described in WO 01/17333
d) Plants, such as cotton plants, with increased expression of sucrose synthase as described in WO 02/45485
e) Plants, such as cotton plants, wherein the timing of the plasmodesmatal gating at the basis of the fiber cell is altered, e.g. through downregulation of fiber-selective β-1,3-glucanase as described in WO 2005/017157, or as described in EP 08075514.3 or U.S. Patent Appl. No. 61/128,938
f) Plants, such as cotton plants, having fibers with altered reactivity, e.g. through the expression of N-acetylglucosaminetransferase gene including nodC and chitin synthase genes as described in WO 2006/136351

Plants or plant cultivars (that can be obtained by plant biotechnology methods such as genetic engineering) which may also be treated according to the invention are plants, such as oilseed rape or related *Brassica* plants, with altered oil profile characteristics. Such plants can be obtained by genetic transformation, or by selection of plants contain a mutation imparting such altered oil profile characteristics and include:

a) Plants, such as oilseed rape plants, producing oil having a high oleic acid content as described e.g. in U.S. Pat. No. 5,969,169, U.S. Pat. No. 5,840,946 or U.S. Pat. No. 6,323,392 or U.S. Pat. No. 6,063,947
b) Plants such as oilseed rape plants, producing oil having a low linolenic acid content as described in U.S. Pat. No. 6,270,828, U.S. Pat. No. 6,169,190, or U.S. Pat. No. 5,965,755
c) Plant such as oilseed rape plants, producing oil having a low level of saturated fatty acids as described e.g. in U.S. Pat. No. 5,434,283 or U.S. patent application Ser. No. 12/668,303

Plants or plant cultivars (that can be obtained by plant biotechnology methods such as genetic engineering) which may also be treated according to the invention are plants, such as oilseed rape or related *Brassica* plants, with altered seed shattering characteristics. Such plants can be obtained by genetic transformation, or by selection of plants contain a mutation imparting such altered seed shattering characteristics and include plants such as oilseed rape plants with delayed or reduced seed shattering as described in U.S. Patent Appl. No. 61/135,230 WO09/068,313 and WO10/006,732.

Particularly useful transgenic plants which may be treated according to the invention are plants containing transformation events, or combination of transformation events, that are the subject of petitions for nonregulated status, in the United States of America, to the Animal and Plant Health Inspection Service (APHIS) of the United States Department of Agriculture (USDA) whether such petitions are granted or are still pending. At any time this information is readily available from APHIS (4700 River Road Riverdale, Md. 20737, USA), for instance on its internet site (URL http://www.aphis.usda.gov/brs/not_reg.html). On the filing date of this application the petitions for nonregulated status that were pending with APHIS or granted by APHIS were those listed in table B which contains the following information:

Petition: the identification number of the petition. Technical descriptions of the transformation events can be found in the individual petition documents which are obtainable from APHIS, for example on the APHIS website, by reference to this petition number. These descriptions are herein incorporated by reference.

Extension of Petition: reference to a previous petition for which an extension is requested.

Institution: the name of the entity submitting the petition.

Regulated article: the plant species concerned.

Transgenic phenotype: the trait conferred to the plants by the transformation event.

Transformation event or line: the name of the event or events (sometimes also designated as lines or lines) for which nonregulated status is requested.

APHIS documents: various documents published by APHIS in relation to the Petition and which can be requested with APHIS.

Additional particularly useful plants containing single transformation events or combinations of transformation events are listed for example in the databases from various national or regional regulatory agencies (see for example http://gmoinfo.jrc.it/gmp_browse.aspx and http://www.agbios.com/dbase.php).

Further particularly transgenic plants include plants containing a transgene in an agronomically neutral or beneficial position as described in any of the patent publications listed in Table C.

TABLE A

| Trait | Reference | |
|---|---|---|
| Water use efficiency | WO 2000/073475 | |
| Nitrogen use efficiency | WO 1995/009911 | WO 2007/076115 |
| | WO 1997/030163 | WO 2005/103270 |
| | WO 2007/092704 | WO 2002/002776 |
| Improved photosynthesis | WO 2008/056915 | WO 2004/101751 |
| Nematode resistance | WO 1995/020669 | WO 2003/033651 |
| | WO 2001/051627 | WO 1999/060141 |
| | WO 2008/139334 | WO 1998/012335 |
| | WO 2008/095972 | WO 1996/030517 |
| | WO 2006/085966 | WO 1993/018170 |
| Reduced pod dehiscence | WO 2006/009649 | WO 1997/013865 |
| | WO 2004/113542 | WO 1996/030529 |
| | WO 1999/015680 | WO 1994/023043 |
| | WO 1999/000502 | |
| Aphid resistance | WO 2006/125065 | WO 2008/067043 |
| | WO 1997/046080 | WO 2004/072109 |
| Sclerotinia resistance | WO 2006/135717 | WO 2005/000007 |
| | WO 2006/055851 | WO 2002/099385 |
| | WO 2005/090578 | WO 2002/061043 |
| Botrytis resistance | WO 2006/046861 | WO 2002/085105 |
| Bremia resistance | US 20070022496 | WO 2004/049786 |
| | WO 2000/063432 | |
| Erwinia resistance | WO 2004/049786 | |
| Closterovirus resistance | WO 2007/073167 | WO 2002/022836 |
| | WO 2007/053015 | |
| Stress tolerance (including drought tolerance) | WO 2010/019838 | WO2008/002480 |
| | WO 2009/049110 | WO2005/033318 |
| Tobamovirus resistance | WO 2006/038794 | |

TABLE B

Petitions of Nonregulated Status Granted or Pending by APHIS as of Mar. 31, 2010

Applicant Documents

| Petition | Extension of Petition Number *** | Institution | Regulated Article | Transgenic Phenotype | Transformation Event or Line |
|---|---|---|---|---|---|
| Petitions for Nonregulated Status Pending | | | | | |
| 10-070-01p | | Virginia Tech | Peanut | Sclerotinia blight resistant | N70, P39, and W171 |
| 09-349-01p | | Dow AgroSciences | Soybean | Herbicide Tolerant | DAS-68416-4 |
| 09-328-01p | | Bayer Crop Science | Soybean | Herbicide Tolerant | FG72 |
| 09-233-01p | | Dow | Corn | Herbicide Tolerant | DAS-40278-9 |
| 09-201-01p | | Monsanto | Soybean | | MON-87705-6 |
| 09-183-01p | | Monsanto | Soybean | | MON-87769 |
| 09-082-01p | | Monsanto | Soybean | Lepidopteran resistant | MON 87701 |
| 09-063-01p | | Stine Seed | Corn | Glyphosate tolerant | HCEM485 |
| 09-055-01p | | Monsanto | Corn | Drought Tolerant | MON 87460 |
| 09-015-01p | | BASF Plant Science, LLC | Soybean | Herbicide Tolerant | BPS-CV127-9 Soybean |
| 08-366-01p | | ArborGen | Eucalyptus | Freeze Tolerant, Fertility Altered | ARB-FTE1-08 |
| 08-340-01p | | Bayer | Cotton | Glufosinate Tolerant, Insect Resistant | T304-40XGHB119 |
| 08-338-01p | | Pioneer | Corn | Male Sterile, Fertility Restored, Visual Marker | DP-32138-1 |
| 08-315-01p | | Florigene | Rose | Altered Flower Color | IFD-52401-4 and IFD-52901-9 |
| 07-253-01p | | Syngenta | Corn | Lepidopteran resistant | MIR-162 Maize |
| 07-108-01p | | Syngenta | Cotton | Lepidopteran Resistant | COT67B |
| 06-354-01p | | Pioneer | Soybean | High Oleic Acid | DP-305423-1 |
| 05-280-01p | | Syngenta | Corn | Thermostable alpha-amylase | 3272 |
| 04-110-01p | | Monsanto & Forage Genetics | Alfalfa | Glyphosate Tolerant | J101, J163 |
| 03-104-01p | | Monsanto & Scotts | Creeping bentgrass | Glyphosate Tolerant | ASR368 |
| Petitions for Nonregulated Status Granted | | | | | |
| 07-152-01p | | Pioneer | Corn | glyphosate & Imidazolinone tolerant | DP-098140-6 |
| 04-337-01p | | University of Florida | Papaya | Papaya Ringspot Virus Resistant | X17-2 |
| 06-332-01p | | Bayer CropScience | Cotton | Glyphosate tolerant | GHB614 |
| 06-298-01p | | Monsanto | Corn | European Corn Borer resistant | MON 89034 |
| 06-271-01p | | Pioneer | Soybean | Glyphosate & acetolactate synthase tolerant | 356043 (DP-356043-5) |
| 06-234-01p | 98-329-01p | Bayer CropScience | Rice | Phosphinothricin tolerant | LLRICE601 |
| 06-178-01p | | Monsanto | Soybean | Glyphosate tolerant | MON 89788 |
| 04-362-01p | | Syngenta | Corn | Corn Rootworm Protected | MIR604 |
| 04-264-01p | | ARS | Plum | Plum Pox Virus Resistant | C5 |
| 04-229-01p | | Monsanto | Corn | High Lysine | LY038 |
| 04-125-01p | | Monsanto | Corn | Corn Rootworm Resistant | 88017 |
| 04-086-01p | | Monsanto | Cotton | Glyphosate Tolerant | MON 88913 |
| 03-353-01p | | Dow | Corn | Corn Rootworm Resistant | 59122 |
| 03-323-01p | | Monsanto | Sugar Beet | Glyphosate Tolerant | H7-1 |
| 03-181-01p | 00-136-01p | Dow | Corn | Lepidopteran Resistant & Phosphinothricin tolerant | TC-6275 |
| 03-155-01p | | Syngenta | Cotton | Lepidopteran Resistant | COT 102 |
| 03-036-01p | | Mycogen/Dow | Cotton | Lepidopteran Resistant | 281-24-236 |
| 03-036-02p | | Mycogen/Dow | Cotton | Lepidopteran Resistant | 3006-210-23 |
| 02-042-01p | | Aventis | Cotton | Phosphinothericin tolerant | LLCotton25 |

TABLE B-continued

Petitions of Nonregulated Status Granted or Pending by APHIS as of Mar. 31, 2010

Applicant Documents

| Petition | Extension of Petition Number *** | Institution | Regulated Article | Transgenic Phenotype | Transformation Event or Line |
|---|---|---|---|---|---|
| 01-324-01p | 98-216-01p | Monsanto | Rapeseed | Glyphosate tolerant | RT200 |
| 01-206-01p | 98-278-01p | Aventis | Rapeseed | Phosphinothricin tolerant & pollination control | MS1 & RF1/RF2 |
| 01-206-02p | 97-205-01p | Aventis | Rapeseed | Phosphinothricin tolerant | Topas 19/2 |
| 01-137-01p | | Monsanto | Corn | Corn Rootworm Resistant | MON 863 |
| 01-121-01p | | Vector | Tobacco | Reduced nicotine | Vector 21-41 |
| 00-342-01p | | Monsanto | Cotton | Lepidopteran resistant | Cotton Event 15985 |
| 00-136-01p | | Mycogen c/o Dow & Pioneer | Corn | Lepidopteran resistant phosphinothricin tolerant | Line 1507 |
| 00-011-01p | 97-099-01p | Monsanto | Corn | Glyphosate tolerant | NK603 |
| 99-173-01p | 97-204-01p | Monsanto | Potato | PLRV & CPB resistant | RBMT22-82 |
| 98-349-01p | 95-228-01p | AgrEvo | Corn | Phosphinothricin tolerant and Male sterile | MS6 |
| 98-335-01p | | U. of Saskatchewan | Flax | Tolerant to soil residues of sulfonyl urea herbicide | CDC Triffid |
| 98-329-01p | | AgrEvo | Rice | Phosphinothricin tolerant | LLRICE06, LLRICE62 |
| 98-278-01p | | AgrEvo | Rapeseed | Phosphinothricin tolerant & Pollination control | MS8 & RF3 |
| 98-238-01p | | AgrEvo | Soybean | Phosphinothricin tolerant | GU262 |
| 98-216-01p | | Monsanto | Rapeseed | Glyphosate tolerant | RT73 |
| 98-173-01p | | Novartis Seeds & Monsanto | Beet | Glyphosate tolerant | GTSB77 |
| 98-014-01p | 96-068-01p | AgrEvo | Soybean | Phosphinothricin tolerant | A5547-127 |
| 97-342-01p | | Pioneer | Corn | Male sterile & Phosphinothricin tolerant | 676, 678, 680 |
| 97-339-01p | | Monsanto | Potato | CPB & PVY resistant | RBMT15-101, SEMT15-02, SEMT15-15 |
| 97-336-01p | | AgrEvo | Beet | Phosphinothricin tolerant | T-120-7 |
| 97-287-01p | | Monsanto | Tomato | Lepidopteran resistant | 5345 |
| 97-265-01p | | AgrEvo | Corn | Phosphinothricin tolerant & Lep. resistant | CBH-351 |
| 97-205-01p | | AgrEvo | Rapeseed | Phosphinothricin tolerant | T45 |
| 97-204-01p | | Monsanto | Potato | CPB & PLRV resistant | RBMT21-129 & RBMT21-350 |
| 97-148-01p | | Bejo | *Cichorium intybus* | Male sterile | RM3-3, RM3-4, RM3-6 |
| 97-099-01p | | Monsanto | Corn | Glyphosate tolerant | GA21 |
| 97-013-01p | | Calgene | Cotton | Bromoxynil tolerant & Lepidopteran resistant | Events 31807 & 31808 |
| 97-008-01p | | Du Pont | Soybean | Oil profile altered | G94-1, G94-19, G-168 |
| 96-317-01p | | Monsanto | Corn | Glyphosate tolerant & ECB resistant | MON802 |
| 96-291-01p | | DeKalb | Corn | European Corn Borer resistant | DBT418 |
| 96-248-01p | 92-196-01p | Calgene | Tomato | Fruit ripening altered | 1 additional FLAVRSAVR line |
| 96-068-01p | | AgrEvo | Soybean | Phosphinothricin tolerant | W62, W98, A2704-12, A2704-21, A5547-35 |
| 96-051-01p | | Cornell U | Papaya | PRSV resistant | 55-1, 63-1 |
| 96-017-01p | 95-093-01p | Monsanto | Corn | European Corn Borer resistant | MON809 & MON810 |
| 95-352-01p | | Asgrow | Squash | CMV, ZYMV, WMV2 resistant | CZW-3 |

TABLE B-continued

Petitions of Nonregulated Status Granted or Pending by APHIS as of Mar. 31, 2010

Applicant Documents

| Petition | Extension of Petition Number *** | Institution | Regulated Article | Transgenic Phenotype | Transformation Event or Line |
|---|---|---|---|---|---|
| 95-338-01p | | Monsanto | Potato | CPB resistant | SBT02-5 & -7, ATBT04-6 &-27, -30, -31, -36 |
| 95-324-01p | | Agritope | Tomato | Fruit ripening altered | 35 1 N |
| 95-256-01p | | Du Pont | Cotton | Sulfonylurea tolerant | 19-51a |
| 95-228-01p | | Plant Genetic Systems | Corn | Male sterile | MS3 |
| 95-195-01p | | Northrup King | Corn | European Corn Borer resistant | Bt11 |
| 95-179-01p | 92-196-01p | Calgene | Tomato | Fruit ripening altered | 2 additional FLAVRSAVR lines |
| 95-145-01p | | DeKalb | Corn | Phosphinothricin tolerant | B16 |
| 95-093-01p | | Monsanto | Corn | Lepidopteran resistant | MON 80100 |
| 95-053-01p | | Monsanto | Tomato | Fruit ripening altered | 8338 |
| 95-045-01p | | Monsanto | Cotton | Glyphosate tolerant | 1445, 1698 |
| 95-030-01p | 92-196-01p | Calgene | Tomato | Fruit ripening altered | 20 additional FLAVRSAVR lines |
| 94-357-01p | | AgrEvo | Corn | Phosphinothricin tolerant | T14, T25 |
| 94-319-01p | | Ciba Seeds | Corn | Lepidopteran resistant | Event 176 |
| 94-308-01p | | Monsanto | Cotton | Lepidopteran resistant | 531, 757, 1076 |
| 94-290-01p | | Zeneca & Petoseed | Tomato | Fruit polygalacturonase level decreased | B, Da, F |
| 94-257-01p | | Monsanto | Potato | Coleopteran resistant | BT6, BT10, BT12, BT16, BT17, BT18, BT23 |
| 94-230-01p | 92-196-01p | Calgene | Tomato | Fruit ripening altered | 9 additional FLAVRSAVR lines |
| 94-228-01p | | DNA Plant Tech | Tomato | Fruit ripening altered | 1345-4 |
| 94-227-01p | 92-196-01p | Calgene | Tomato | Fruit ripening altered | Line N73 1436-111 |
| 94-090-01p | | Calgene | Rapeseed | Oil profile altered | pCGN3828-212/86- 18 & 23 |
| 93-258-01p | | Monsanto | Soybean | Glyphosate tolerant | 40-3-2 |
| 93-196-01p | | Calgene | Cotton | Bromoxynil tolerant | BXN |
| 92-204-01p | | Upjohn | Squash | WMV2 & ZYMV resistant | ZW-20 |
| 92-196-01p | | Calgene | Tomato | Fruit ripening altered | FLAVR SAVR |

NOTE:
To obtain the most up-to-date list of Crops No Longer Regulated, please look at the Current Status of Petitions. This list is automatically updated and reflects all petitions received to date by APHIS, including petitions pending, withdrawn, or approved.
Abbreviations:
CMV—cucumber mosaic virus; CPB—colorado potato beetle; PLRV—potato leafroll virus; PRSV—papaya ringspot virus; PVY—potato virus Y; WMV2—watermelon mosaic virus 2 ZYMV—zucchini yellow mosaic virus
*** Extension of Petition Number: Under 7CFR 340.6(e) a person may request that APHIS extend a determination of non-regulated status to other organisms based on their similarity of the previously deregulated article. This column lists the previously granted petition of that degregulated article.
**** Preliminary EA: The Environmental Assessment initially available for Public comment prior to finalization.

TABLE C

| Plant species | Event | Trait | Patent reference |
|---|---|---|---|
| Corn | PV-ZMGT32 (NK603) | Glyphosate tolerance | US 2007-056056 |
| Corn | MIR604 | Insect resistance (Cry3a055) | EP 1 737 290 |
| Corn | LY038 | High lysine content | U.S. Pat. No. 7,157,281 |
| Corn | 3272 | Self processing corn (alpha-amylase) | US 2006-230473 |
| Corn | PV-ZMIR13 (MON863) | Insect resistance (Cry3Bb) | US 2006-095986 |
| Corn | DAS-59122-7 | Insect resistance (Cry34Ab1/Cry35Ab1) | US 2006-070139 |
| Corn | TC1507 | Insect resistance (Cry1F) | U.S. Pat. No. 7,435,807 |
| Corn | MON810 | Insect resistance (Cry1Ab) | US 2004-180373 |
| Corn | VIP1034 | Insect resistance | WO 03/052073 |
| Corn | B16 | Glufosinate resistance | US 2003-126634 |
| Corn | GA21 | Glyphosate resistance | U.S. Pat. No. 6,040,497 |
| Corn | GG25 | Glyphosate resistance | U.S. Pat. No. 6,040,497 |
| Corn | GJ11 | Glyphosate resistance | U.S. Pat. No. 6,040,497 |
| Corn | FI117 | Glyphosate resistance | U.S. Pat. No. 6,040,497 |
| Corn | GAT-ZM1 | Glufosinate tolerance | WO 01/51654 |

TABLE C-continued

| Plant species | Event | Trait | Patent reference |
|---|---|---|---|
| Corn | MON87460 | Drought tolerance | WO 2009/111263 |
| Corn | DP-098140-6 | Glyphosate tolerance/ALS inhibitor tolerance | WO 2008/112019 |
| Wheat | Event 1 | Fusarium resistance (trichothecene 3-O-acetyltransferase) | CA 2561992 |
| Sugar beet | T227-1 | Glyphosate tolerance | US 2004-117870 |
| Sugar beet | H7-1 | Glyphosate tolerance | WO 2004-074492 |
| Soybean | MON89788 | Glyphosate tolerance | US 2006-282915 |
| Soybean | A2704-12 | Glufosinate tolerance | WO 2006/108674 |
| Soybean | A5547-35 | Glufosinate tolerance | WO 2006/108675 |
| Soybean | DP-305423-1 | High oleic acid/ALS inhibitor tolerance | WO 2008/054747 |
| Rice | GAT-OS2 | Glufosinate tolerance | WO 01/83818 |
| Rice | GAT-OS3 | Glufosinate tolerance | US 2008-289060 |
| Rice | PE-7 | Insect resistance (Cry1Ac) | WO 2008/114282 |
| Oilseed rape | MS-B2 | Male sterility | WO 01/31042 |
| Oilseed rape | MS-BN1/RF-BN1 | Male sterility/restoration | WO 01/41558 |
| Oilseed rape | RT73 | Glyphosate resistance | WO 02/36831 |
| Cotton | CE43-67B | Insect resistance (Cry1Ab) | WO 2006/128573 |
| Cotton | CE46-02A | Insect resistance (Cry1Ab) | WO 2006/128572 |
| Cotton | CE44-69D | Insect resistance (Cry1Ab) | WO 2006/128571 |
| Cotton | 1143-14A | Insect resistance (Cry1Ab) | WO 2006/128569 |
| Cotton | 1143-51B | Insect resistance (Cry1Ab) | WO 2006/128570 |
| Cotton | T342-142 | Insect resistance (Cry1Ab) | WO 2006/128568 |
| Cotton | event3006-210-23 | Insect resistance (Cry1Ac) | WO 2005/103266 |
| Cotton | PV-GHGT07 (1445) | Glyphosate tolerance | US 2004-148666 |
| Cotton | MON88913 | Glyphosate tolerance | WO 2004/072235 |
| Cotton | EE-GH3 | Glyphosate tolerance | WO 2007/017186 |
| Cotton | T304-40 | Insect-resistance (Cry1Ab) | WO2008/122406 |
| Cotton | Cot202 | Insect resistance (VIP3) | US 2007-067868 |
| Cotton | LLcotton25 | Glufosinate resistance | WO 2007/017186 |
| Cotton | EE-GH5 | Insect resistance (Cry1Ab) | WO 2008/122406 |
| Cotton | event 281-24-236 | Insect resistance (Cry1F) | WO 2005/103266 |
| Cotton | Cot102 | Insect resistance (Vip3A) | US 2006-130175 |
| Cotton | MON 15985 | Insect resistance (Cry1A/Cry2Ab) | US 2004-250317 |
| Bent Grass | Asr-368 | Glyphosate tolerance | US 2006-162007 |
| Brinjal | EE-1 | Insect resistance (Cry1Ac) | WO 2007/091277 |

The plants listed can be treated according to the invention in a particularly advantageous manner with the compounds of the general formula (I) or the active compound mixtures according to the invention. The preferred ranges stated above for the active compounds or mixtures also apply to the treatment of these plants. Particular emphasis is given to the treatment of plants with the compounds or mixtures specifically mentioned in the present text.

The invention further relates to a fungicide composition comprising, as an active ingredient, an effective amount of a compound of formula (I) according to the invention and an agriculturally acceptable support, carrier or filler.

The invention further relates to a method for controlling phytopathogenic fungi of crops, characterized in that an agronomically effective and substantially non-phytotoxic quantity of a compound according to the invention or a composition according to the invention is applied to the soil where plants grow or are capable of growing, to the leaves and/or the fruit of plants or to the seeds of plants.

The invention further relates to a method for controlling unwanted microorganisms, characterized in that (thio)carboxamides of the formula (I) according to the invention are applied to the microorganisms and/or their habitat.

The invention further relates to a process for preparing compositions for controlling unwanted microorganisms, characterized in that carboxamides of the formula (I) according to the invention are mixed with extenders and/or surfactants.

The invention further relates to the use of (thio)carboxamides of the formula (I) according to the invention for treating seed.

The invention further relates to the use of (thio)carboxamides of the formula (I) according to the invention for treating transgenic plants.

The preparation and the use of the active compounds (thio)carboxamides of the formula (I) according to the invention and the intermediates is illustrated by the examples below.

Procedure for Synthesizing Amides of the Formula (I) According to the Invention from Compounds of the Formula (II) and Compounds of the Formula (III) According to Process (a):

4 mL of a 0.15 molar solution (0.60 mmol) of an amine according to formula III as described above are initially charged in a 13 mL Chemspeed™ reaction tube in dichloromethane, followed by 0.72 mmol of triethylamine. At a rate of 1 mL/min, 2 mL of a 0.30 molar solution of the acyl chloride (IIb) or (IIe) (0.60 mmol) are added, and the mixture is stirred at room temperature overnight. 1 mL of water is then added, and the mixture is applied to a cartridge with basic alumina (weight 2 g) and eluted with dichloromethane. The solvent is removed and the reaction mixture is analyzed by LCMS and NMR. Impure products are purified further by preparative LCMS.

Procedure for Synthesizing the Carboxylic Acid Derivatives of the Formula (II) According to the Invention According to Process (c):

5-Chloro-3-(difluoromethyl)-1-methyl-1H-pyrazole-4-carboxylic acid (Example IIb)

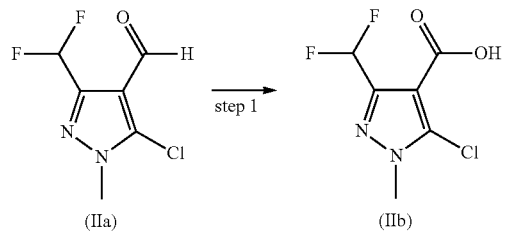

(IIa) → (IIb)

step 1

In a 500 mL round-bottom flask, 6.0 g (31 mmol) of 5-chloro-3-(difluoromethyl)-1-methyl-1H-pyrazole-4-carbaldehyde were taken up in 30 mL of toluene. A solution of 2.4 g (62 mmol) of sodium hydroxide in 6 mL of water was added to the reaction mixture, followed by 103 mL of a 30% strength solution of hydrogen peroxide in water. During the addition, the temperature was kept below 37° C. The reaction mixture was then stirred at 50° C. for 7 h. After cooling, the organic phase was extracted with 100 mL of water. The aqueous phase was acidified to pH 2 using dilute hydrochloric acid. The white precipitate formed was filtered off, washed twice with 20 mL of water and dried. This gave 3.2 g of 5-chloro-3-(difluoromethyl)-1-methyl-1H-pyrazole-4-carboxylic acid as a white solid.

$^1$H NMR (400 MHz, DMSO-$d_6$) δ ppm: 3.78 (s, 3H); 7.12 (t, 1H, $J_{HF}$=53.60 Hz); 13.19 (s, 1H);

IR (KBr): 1688 cm$^{-1}$ (C=O); 2200-3200 cm$^{-1}$ broad;

5-Chloro-3-(difluoromethyl)-1-methyl-1H-pyrazole-4-carbonyl chloride (Example IIc)

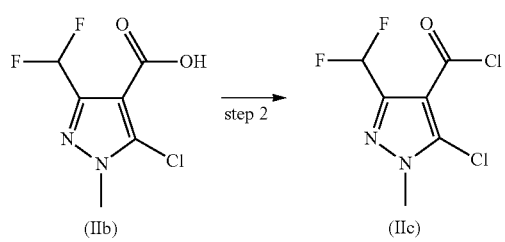

(IIb) → (IIc)

step 2

3.2 g of 5-chloro-3-(difluoromethyl)-1-methyl-1H-pyrazole-4-carboxylic acid and 44.3 mL of thionyl chloride were heated under reflux for 5 h. After cooling, the reaction mixture was concentrated under reduced pressure, giving 3.5 g of 5-chloro-3-(difluoromethyl)-1-methyl-1H-pyrazole-4-carbonyl chloride as a yellow oil.

$^1$H NMR (400 MHz, CHCl$_3$-$d_6$) δ ppm: 3.97 (s, 3H); 7.00 (t, J=52.01 Hz, 1H);

IR (TQ): 1759 and 1725 cm$^{-1}$ (C=O);

3-(Difluoromethyl)-5-fluoro-1-methyl-1H-pyrazole-4-carbonyl fluoride (Example IId)

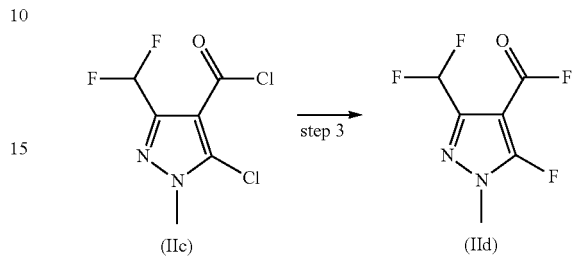

(IIc) → (IId)

step 3

At 100° C., a solution of 5.0 g (22 mmol) of 5-chloro-3-(difluoromethyl)-1-methyl-1H-pyrazole-4-carbonyl chloride in 15 mL of toluene was added to a dried solution of 4.0 g (70 mmol) of potassium fluoride in 21 mL of tetrahydrothiophene-1,1-dioxide. The reaction mixture was then stirred at 190-200° C. for 22 h. Removal of the solvent under reduced pressure gave 8 g of a solution (25% molar) of 3-(difluoromethyl)-5-fluoro-1-methyl-1H-pyrazole-4-carbonyl fluoride in tetrahydrothiophene-1,1-dioxide.

$^1$H NMR (250 MHz, CHCl$_3$-$d_6$) δ ppm: 3.87 (s, 3H); 6.79 (t, J=53.75 Hz, 1H);

$^{19}$F NMR (250 MHz, CHCl$_3$-$d_6$) δ ppm: 45.37 (s, COF); −117.5 (d, J=28.2 Hz); −131.6 (m);

5-Fluoro-3-(difluoromethyl)-1-methyl-1H-pyrazole-4-carboxylic acid (Example IIe)

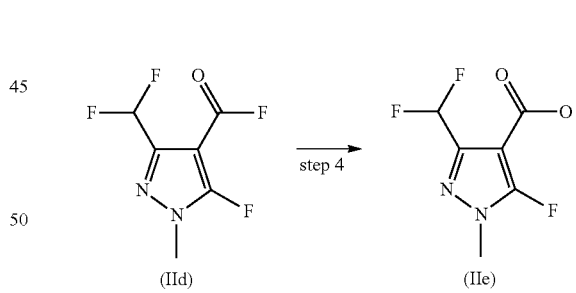

(IId) → (IIe)

step 4

67.5 g of a solution (10% molar) of 3-(difluoromethyl)-5-fluoro-1-methyl-1H-pyrazole-4-carbonyl fluoride in tetrahydrothiophene-1,1-dioxide were added dropwise to 400 mL of an aqueous 1N NaOH solution. During the addition, the temperature was kept below 20. After 2 h of stirring at room temperature, the mixture was carefully acidified to pH 2 using concentrated hydrochloric acid. The white precipitate formed was filtered off, washed with water and dried. This gave 6 g of 5-fluoro-3-(difluoromethyl)-1-methyl-1H-pyrazole-4-carboxylic acid as a white solid.

$^1$H NMR (400 MHz, DMSO-d$_6$) δ ppm: 3.90 (s, 3H); 7.22 (t, 1H, J$_{HF}$=53.55 Hz); 13.33 (s, 1H);

5-Fluoro-3-(difluoromethyl)-1-methyl-1H-pyrazole-4-carbonyl chloride (Example IIf)

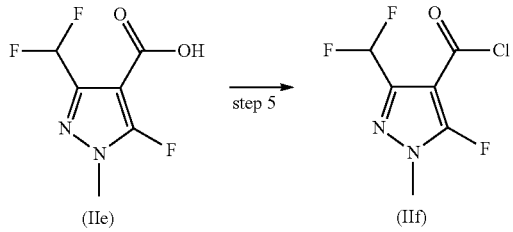

9.1 g of 5-fluoro-3-(difluoromethyl)-1-methyl-1H-pyrazole-4-carboxylic acid and 75.5 mL of thionyl chloride were heated under reflux for 1.5 h. After cooling, the reaction mixture was concentrated under reduced pressure, giving 10 g of 5-fluoro-3-(difluoromethyl)-1-methyl-1H-pyrazole-4-carbonyl chloride as a yellow oil.

GC-MS (M$^{+·}$)=212; fragments: (M$^{+·}$-Cl)=177 and (M$^{+·}$-F)= 193;

General Procedure for Synthesizing Thioamides of the Formula (I) According to the Invention from Amides of the Formula (I) According to Process (c):

In a 13 mL Chemspeed™ vial is weighed 0.27 mmol of phosphorous pentasulfide (P$_2$S$_5$). 3 mL of a 0.18 molar solution of the amide (I) (0.54 mmol) in dioxane is added and the mixture is heated at reflux for two hours. The temperature is then cooled to 80° C. and 2.5 mL of water are added. The mixture is heated at 80° C. for one more hour. 2 mL of water are then added and the reaction mixture is extracted twice by 4 mL of dichloromethane. The organic phase is deposited on a basic alumina cartridge (2 g) and eluted twice by 8 mL of dichloromethane. The solvents are removed and the crude thioamide derivative is analyzed by LCMS and NMR. Insufficiently pure compounds are further purified by preparative LCMS.

The following examples of compounds according to formula (I) are listed in Table 1 below:

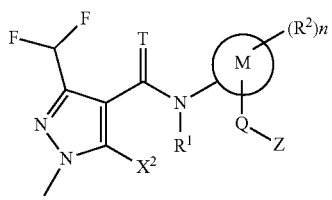

where n is equal to 0 and M has the following meaning:

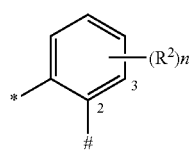

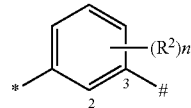

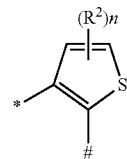

where the bond marked by * is attached to the amide while the bond marked # is attached to Q-Z;

TABLE 1

| Ex. | X$^2$ | T | R$^1$ | M | Q-Z | logP | Mass (M + H) |
|---|---|---|---|---|---|---|---|
| 1 | Cl | O | methyl | M-1 | 3,3-dimethylbutyl | 4.15 | |
| 2 | Cl | O | methyl | M-3 | 3,3-dimethylbutyl | 4.16 | 390 |
| 3 | Cl | O | methyl | M-3 | 2-ethylbutyl | 4.16 | 390 |
| 4 | F | O | ethyl | | (benzo[1,3]dioxol-5-yl) | 2.32 | 342 |
| 5 | Cl | O | ethyl | | (benzo[1,3]dioxol-5-yl) | 2.40 | 358 |
| 6 | F | O | methyl | M-3 | phenyl | 2.90 | 366 |
| 7 | F | O | methyl | M-1 | 2-methyphenyl | 3.19 | 374 |
| 8 | Cl | O | methyl | M-1 | 2-methyphenyl | 3.41 | 390 |
| 9 | F | O | methyl | M-1 | 3,5-dimethylphenyl | 3.67 | 388 |
| 10 | Cl | O | methyl | M-1 | 3,5-dimethylphenyl | 3.85 | 404 |
| 11 | F | O | methyl | M-1 | 3,5-difluorophenyl | 3.15 | 396 |
| 12 | Cl | O | methyl | M-1 | 3,5-difluorophenyl | 3.33 | 412 |
| 13 | F | O | methyl | M-1 | 3-isopropylphenyl | 4.01 | 402 |
| 14 | Cl | O | methyl | M-1 | 3-isopropylphenyl | 4.19 | 418 |
| 15 | F | O | methyl | M-1 | 4-isopropylphenyl | 4.01 | 402 |
| 16 | Cl | O | methyl | M-1 | 4-isopropylphenyl | 4.21 | 418 |
| 17 | F | O | methyl | M-1 | 3-chloro-4-fluorophenyl | 3.37 | 412 |
| 18 | Cl | O | methyl | M-1 | 3-chloro-4-fluorophenyl | 3.58 | 428 |
| 19 | F | O | methyl | M-1 | 4-tert-butylphenyl | 4.29 | 416 |
| 20 | Cl | O | methyl | M-1 | 4-tert-butylphenyl | 4.49 | 432 |
| 21 | F | O | methyl | M-1 | 3-isopropoxyphenyl | 3.60 | 418 |
| 22 | Cl | O | methyl | M-1 | 3-isopropoxyphenyl | 3.76 | 434 |
| 23 | F | O | methyl | M-1 | 4-isopropoxyphenyl | 3.60 | 418 |
| 24 | Cl | O | methyl | M-1 | 4-isopropoxyphenyl | 3.78 | 434 |
| 25 | F | O | methyl | M-1 | 2,3-dichlorophenyl | 3.48 | 428 |
| 26 | Cl | O | methyl | M-1 | 2,3-dichlorophenyl | 3.73 | 444 |
| 27 | F | O | methyl | M-1 | 2,4-dichlorophenyl | 3.67 | 428 |
| 28 | Cl | O | methyl | M-1 | 2,4-dichlorophenyl | 3.92 | 444 |
| 29 | F | O | methyl | M-1 | 3,5-dichlorophenyl | 3.83 | 428 |
| 30 | Cl | O | methyl | M-1 | 3,5-dichlorophenyl | 4.06 | 444 |
| 31 | F | O | methyl | M-1 | 4-(trifluoromethyl)phenyl | 3.51 | 428 |
| 32 | Cl | O | methyl | M-1 | 4-(trifluoromethyl)phenyl | 3.69 | 444 |
| 33 | F | O | methyl | M-1 | 4-[(1E)-N-methoxy ethanimidoyl]phenyl | 3.48 | 431 |
| 34 | Cl | O | methyl | M-1 | 4-[(1E)-N-methoxy ethanimidoyl]phenyl | 3.67 | 447 |
| 35 | F | O | methyl | M-1 | 3-(trimethylsilyl)phenyl | 4.61 | 432 |
| 36 | Cl | O | methyl | M-1 | 3-(trimethylsilyl)phenyl | 4.76 | 448 |
| 37 | F | O | methyl | M-1 | 4-(trimethylsilyl)phenyl | 4.63 | 432 |
| 38 | Cl | O | methyl | M-1 | 4-(trimethylsilyl)phenyl | 4.81 | 448 |
| 39 | Cl | O | methyl | M-1 | 4-isobutoxyphenyl | 4.44 | 448 |
| 40 | F | O | methyl | M-1 | 4-isobutoxyphenyl | 4.26 | 432 |
| 41 | F | O | methyl | M-1 | 3-(trifluoromethoxy) phenyl | 3.67 | 444 |
| 42 | Cl | O | methyl | M-1 | 3-(trifluoromethoxy) phenyl | 3.83 | 460 |

TABLE 1-continued

| Ex. | $X^2$ | T | $R^1$ | M | Q-Z | logP | Mass (M+H) |
|---|---|---|---|---|---|---|---|
| 43 | F | O | methyl | M-1 | 4-(trifluoromethoxy) phenyl | 3.67 | 444 |
| 44 | Cl | O | methyl | M-1 | 4-(trifluoromethoxy) phenyl | 3.85 | 460 |
| 45 | F | O | methyl | M-1 | 4-[(E)-(isopropoxyimino) methyl]phenyl | 4.06 | 445 |
| 46 | Cl | O | methyl | M-1 | 4-[(E)-(isopropoxyimino) methyl]phenyl | 4.24 | 461 |
| 47 | F | O | methyl | M-1 | 4-[(1E)-N-tert-butoxy ethanimidoyl]phenyl | 4.91 | 473 |
| 48 | Cl | O | methyl | M-1 | 4-[(1E)-N-tert-butoxy ethanimidoyl]phenyl | 5.08 | 489 |
| 49 | F | O | methyl | M-2 | 2-methyphenyl | 3.46 | 374 |
| 50 | Cl | O | methyl | M-2 | 2-methyphenyl | 3.59 | 390 |
| 51 | F | O | methyl | M-2 | 3,5-dimethylphenyl | 3.96 | 388 |
| 52 | Cl | O | methyl | M-2 | 3,5-dimethylphenyl | 4.09 | 404 |
| 53 | F | O | methyl | M-2 | 3,5-difluorophenyl | 3.39 | 396 |
| 54 | Cl | O | methyl | M-2 | 3,5-difluorophenyl | 3.53 | 412 |
| 55 | F | O | methyl | M-2 | 3-isopropylphenyl | 4.24 | 402 |
| 56 | Cl | O | methyl | M-2 | 3-isopropylphenyl | 4.36 | 418 |
| 57 | F | O | methyl | M-2 | 4-isopropylphenyl | 4.31 | 402 |
| 58 | Cl | O | methyl | M-2 | 4-isopropylphenyl | 4.44 | 418 |
| 59 | F | O | methyl | M-2 | 3-chloro-4-fluorophenyl | 3.69 | 412 |
| 60 | Cl | O | methyl | M-2 | 3-chloro-4-fluorophenyl | 3.80 | 428 |
| 61 | F | O | methyl | M-2 | 4-tert-butylphenyl | 4.61 | 416 |
| 62 | Cl | O | methyl | M-2 | 4-tert-butylphenyl | 4.73 | 432 |
| 63 | F | O | methyl | M-2 | 3-isopropoxyphenyl | 3.85 | 418 |
| 64 | Cl | O | methyl | M-2 | 3-isopropoxyphenyl | 3.96 | 434 |
| 65 | F | O | methyl | M-2 | 4-isopropoxyphenyl | 3.85 | 418 |
| 66 | Cl | O | methyl | M-2 | 4-isopropoxyphenyl | 3.96 | 434 |
| 67 | F | O | methyl | M-2 | 2,3-dichlorophenyl | 3.78 | 428 |
| 68 | Cl | O | methyl | M-2 | 2,3-dichlorophenyl | 3.94 | 444 |
| 69 | F | O | methyl | M-2 | 2,4-dichlorophenyl | 3.99 | 428 |
| 70 | Cl | O | methyl | M-2 | 2,4-dichlorophenyl | 4.16 | 444 |
| 71 | F | O | methyl | M-2 | 3,5-dichlorophenyl | 4.24 | 428 |
| 72 | Cl | O | methyl | M-2 | 3,5-dichlorophenyl | 4.39 | 444 |
| 73 | F | O | methyl | M-2 | 4-(trifluoromethyl)phenyl | 3.80 | 428 |
| 74 | Cl | O | methyl | M-2 | 4-(trifluoromethyl)phenyl | 3.92 | 444 |
| 75 | F | O | methyl | M-2 | 4-[(1E)-N-methoxy ethanimidoyl]phenyl | 3.76 | 431 |
| 76 | Cl | O | methyl | M-2 | 4-[(1E)-N-methoxy ethanimidoyl]phenyl | 3.89 | 447 |
| 77 | F | O | methyl | M-2 | 3-(trimethylsilyl)phenyl | 4.81 | 432 |
| 78 | Cl | O | methyl | M-2 | 3-(trimethylsilyl)phenyl | 4.93 | 448 |
| 79 | F | O | methyl | M-2 | 4-(trimethylsilyl)phenyl | 4.93 | 432 |
| 80 | Cl | O | methyl | M-2 | 4-(trimethylsilyl)phenyl | 5.03 | 448 |
| 81 | F | O | methyl | M-2 | 4-isobutoxyphenyl | 4.51 | 432 |
| 82 | Cl | O | methyl | M-2 | 4-isobutoxyphenyl | 4.63 | 448 |
| 83 | F | O | methyl | M-2 | 3-(trifluoromethoxy) phenyl | 3.89 | 444 |
| 84 | Cl | O | methyl | M-2 | 3-(trifluoromethoxy) phenyl | 4.01 | 460 |
| 85 | F | O | methyl | M-2 | 4-(trifluoromethoxy) phenyl | 3.94 | 444 |
| 86 | Cl | O | methyl | M-2 | 4-(trifluoromethoxy) phenyl | 4.06 | 460 |
| 87 | F | O | methyl | M-2 | 4-[(E)-(isopropoxyimino) methyl]phenyl | 4.31 | 445 |
| 88 | Cl | O | methyl | M-2 | 4-[(E)-(isopropoxyimino) methyl]phenyl | 4.46 | 461 |
| 89 | Cl | O | methyl | M-2 | 4-[(1E)-N-tert-butoxy ethanimidoyl]phenyl | 5.25 | 489 |
| 90 | F | O | methyl | M-2 | 4-[(1E)-N-tert-butoxy ethanimidoyl]phenyl | 5.17 | 473 |
| 91 | F | S | methyl | M-3 | phenyl | 3.62 | 382 |

In table 1, unless otherwise specified, M+H (Apcl+) means the molecular ion peak plus 1 a.m.u. (atomic mass unit) as observed in mass spectroscopy via positive atmospheric pressure chemical ionisation. In table 1, the logP values were determined in accordance with EEC Directive 79/831 Annex V.A8 by HPLC (High Performance Liquid Chromatography) on a reversed-phase column (C 18), using the method described below:

Temperature: 40° C.; Mobile phases: 0.1% aqueous formic acid and acetonitrile; linear gradient from 10% acetonitrile to 90% acetonitrile.

Calibration was carried out using unbranched alkan-2-ones (comprising 3 to 16 carbon atoms) with known logP values (determination of the logP values by the retention times using linear interpolation between two successive alkanones). lambda-max-values were determined using UV-spectra from 200 nm to 400 nm and the peak values of the chromatographic signals.

USE EXAMPLES

Example A

*Sphaerotheca* Test (Cucumber)/Preventive

Solvent: 49 parts by weight of N,N-dimethylformamide
Emulsifier: 1 part by weight of alkylarylpolyglycolether To produce a suitable preparation of active compound, 1 part by weight of active compound is mixed with the stated amounts of solvent and emulsifier, and the concentrate is diluted with water to the desired concentration.

To test for preventive activity, young plants are sprayed with the preparation of active compound at the stated rate of application. One day after this treatment, the plants are inoculated with an aqueous spore suspension of *Sphaerotheca fuliginea*. Then the plants are placed in a greenhouse at approximately 23° C. and a relative atmospheric humidity of approximately 70%.

The test is evaluated 7 days after the inoculation. 0% means an efficacy which corresponds to that of the untreated control, while an efficacy of 100% means that no disease is observed.

In this test the following compounds according to the invention showed high efficacy of 90% or even higher at a concentration of 500 ppm of active ingredient:

Example Number: 1 (95%); 7 (93%).

Under the same conditions, high (at least 90%) protection is observed at a dose of 500 ppm of active ingredient with compound 7, whereas poor (less than 20%) protection is observed with the compound of example 102 disclosed in patent application WO-2007/006806 as in table A.

TABLE A

| Example | dose (ppm) | Efficacy |
|---|---|---|
| 7 from this invention | 500 | 93 |
| 102 from WO-2007/006806 | 500 | 20 |

Example 102 disclosed in international patent WO-2007/006806 corresponds to 3-(difluoromethyl)-5-fluoro-1-methyl-N-(2'-methylbiphenyl-2-yl)-1H-pyrazole-4-carboxamide These results show that the compounds according to the invention have a better biological activity than the structurally closest compounds disclosed in WO-2007/006806.

Example B

*Alternaria* Test (Tomato)/Preventive

Solvent: 49 parts by weight of N,N-dimethylformamide
Emulsifier: 1 part by weight of alkylarylpolyglycolether To produce a suitable preparation of active compound, 1 part by weight of active compound is mixed with the stated amounts of solvent and emulsifier, and the concentrate is diluted with water to the desired concentration.

To test for preventive activity, young plants are sprayed with the preparation of active compound at the stated rate of application. One day after this treatment, the plants are inoculated with an aqueous spore suspension of *Alternaria solani*.

The plants remain for one day in an incubation cabinet at approximately 22° C. and a relative atmospheric humidity of 100%. Then the plants are placed in an incubation cabinet at approximately 20° C. and a relative atmospheric humidity of 96%.

The test is evaluated 7 days after the inoculation. 0% means an efficacy which corresponds to that of the untreated control while an efficacy of 100% means that no disease is observed.

In this test the following compounds according to the invention showed high efficacy of 90% or even higher at a concentration of 500 ppm of active ingredient:

Example Number: 1 (90%); 7 (100%).

Example C

*Pyrenophora* Test (Barley)/Preventive

Solvent: 49 parts by weight of N,N-dimethylformamide
Emulsifier: 1 part by weight of alkylarylpolyglycolether To produce a suitable preparation of active compound, 1 part by weight of active compound is mixed with the stated amounts of solvent and emulsifier, and the concentrate is diluted with water to the desired concentration.

To test for preventive activity, young plants are sprayed with the preparation of active compound at the stated rate of application. One day after this treatment, the plants are inoculated with an aqueous spore suspension of *Pyrenophora teres*. The plants remain for 48 hours in an incubation cabinet at 22° C. and a relative atmospheric humidity of 100%. Then the plants are placed in a greenhouse at a temperature of approximately 20° C. and a relative atmospheric humidity of approximately 80%.

The test is evaluated 7-9 days after the inoculation. 0% means an efficacy which corresponds to that of the untreated control while an efficacy of 100% means that no disease is observed.

In this test the following compounds according to the invention showed high efficacy of 90% or even higher at a concentration of 500 ppm of active ingredient:

Example Number: 1 (95%); 7 (100%); 8 (95%)

Example D

*Puccinia* Test (Wheat)/Preventive

Solvent: 49 parts by weight of N,N-dimethylformamide
Emulsifier: 1 part by weight of alkylarylpolyglycolether To produce a suitable preparation of active compound, 1 part by weight of active compound is mixed with the stated amounts of solvent and emulsifier, and the concentrate is diluted with water to the desired concentration.

To test for preventive activity, young plants are sprayed with the preparation of active compound at the stated rate of application. One day after this treatment, the plants are inoculated with an aqueous spore suspension of *Puccinia recondita*. The plants remain for 48 hours in an incubation cabinet at 22° C. and a relative atmospheric humidity of 100%. Then the plants are placed in a greenhouse at a temperature of approximately 20° C. and a relative atmospheric humidity of approximately 80%.

The test is evaluated 7-9 days after the inoculation. 0% means an efficacy which corresponds to that of the untreated control while an efficacy of 100% means that no disease is observed.

In this test the following compound according to the invention showed total efficacy at a concentration of 500 ppm of active ingredient:

Example Number: 1 (100%).

Example E

*Uromyces* Test (Beans)/Preventive

Solvent: 24.5 parts by weight of acetone
24.5 parts by weight of N,N-dimethylacetamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for preventive activity, young plants are sprayed with the preparation of active compound at the stated rate of application. After the spray coating has dried on, the plants are inoculated with an aqueous spore suspension of the causal agent of bean rust (*Uromyces appendiculatus*) and then remain for 1 day in an incubation cabinet at approximately 20° C. and a relative atmospheric humidity of 100%.

The plants are then placed in a greenhouse at approximately 21° C. and a relative atmospheric humidity of approximately 90%.

The test is evaluated 10 days after the inoculation. 0% means an efficacy which corresponds to that of the untreated control, while an efficacy of 100% means that no disease is observed.

In this test the following compound according to the invention showed high efficacy of 90% or even higher at a concentration of 100 ppm of active ingredient:

Example Number: 1 (96%).

Example F

*Phakopsora* Test (Soybeans)/Preventive

Solvent: 24.5 parts by weight of acetone
24.5 parts by weight of N,N-dimethylacetamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for preventive activity, young plants are sprayed with the preparation of active compound at the stated rate of application. After the spray coating has dried on, the plants are inoculated with an aqueous spore suspension of the casual agent of soybean rust. (*Phakopsora pachyrhizi*) and stay for 1 day without light on an incubation cabinet at approximately 23° C. and a relative atmospheric humidity of 95%. The plants remain in the incubation cabinet at approximately 23° C. and a relative atmospheric humidity of approximately 80% and a day/night interval of 12 hours.

The test is evaluated 7 days after the inoculation. 0% means an efficacy which corresponds to that of the untreated control, while an efficacy of 100% means that no disease is observed.

In this test the following compound according to the invention showed high efficacy of 90% or even higher at a concentration of 100 ppm of active ingredient.

Example Number: 1(98%).

The invention claimed is:
1. A (thio)carboxamide derivative of formula (I)

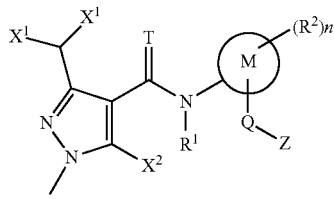

in which
T represents O (oxygen) or S (sulfur),
$X^1$ and $X^2$ which can be the same or different, represent a halogen atom;
$R^1$ represents a substituted or non-substituted $C_1$-$C_8$-alkyl; a $C_1$-$C_8$-halogenoalkyl having 1 to 5 halogen atoms; a non-substituted or substituted $C_3$-$C_7$-cycloalkyl; wherein, when substituted, $C_3$-$C_7$-cycloalkyl is substituted by up to 10 atoms or groups that can be the same or different and that can be selected from the group consisting of halogen atoms, cyano, $C_1$-$C_8$-alkyl, $C_1$-$C_8$-halogenoalkyl comprising up to 9 halogen atoms that can be the same or different, $C_1$-$C_8$-alkoxy, $C_1$-$C_8$-alkoxycarbonyl, $C_1$-$C_8$-halogenoalkoxycarbonyl comprising up to 9 halogen atoms that can be the same or different, $C_1$-$C_8$-alkylaminocarbonyl and di-$C_1$-$C_8$-alkylaminocarbonyl;
M represents a phenyl or thiophene ring
$R^2$ represents fluorine, chlorine, methyl, ethyl, methyl isopropyl, methylsulfanyl or trifluoromethyl,
n represents 0, 1, 2, 3 or 4
Q represents a direct bond, $C_1$-$C_4$-alkylene, $C_2$-$C_4$-alkenylene, O, S, SO, $SO_2$, C=O, $CF_2$ or $NR^3$,
$R^3$ represents hydrogen, $C_1$-$C_8$-alkyl, $C_1$-$C_4$-alkoxy-$C_1$-$C_4$-alkyl, $C_1$-$C_4$-alkylsulfanyl-$C_1$-$C_4$-alkyl, $C_2$-$C_8$-alkenyl, $C_2$-$C_8$-alkynyl, $C_1$-$C_6$-halogenoalkyl, $C_2$-$C_6$-halogenoalkenyl, $C_2$-$C_6$-halogenoalkynyl or $C_3$-$C_6$-cycloalkyl,
Z represents $Z^1$, $Z^2$, $Z^3$, $Z^4$ or $Z^5$,
$Z^1$ represents a phenyl which is optionally mono- to pentasubstituted by identical or different substituents $W^1$,
$Z^2$ represents pyridinyl which is optionally mono- to trisubstituted by identical or different substituents $W^2$,
$Z^3$ represents $C_3$-$C_7$-cycloalkyl or $C_4$-$C_{10}$-bicycloalkyl, each of which is optionally mono- or polysubstituted by identical or different substituents from the group consisting of halogen, alkyl and/or —$(CR^4R^5)_m SiR^6R^7R^8$,
$Z^4$ represents unsubstituted $C_1$-$C_{20}$-alkyl or represents $C_1$-$C_{20}$-alkyl which is mono- or polysubstituted by identical or different substituents from the group consisting of halogen, alkylsulfanyl, alkylsulfinyl, alkylsulfonyl, alkoxy, alkylamino, dialkylamino, halogenoalkylsulfanyl, halogenoalkylsulfinyl, halogenoalkylsulfonyl, halogenoalkoxy, halogenoalkylamino, di(halogenoalkyl)amino, —$SiR^6R^7R^8$ and $C_3$-$C_6$-cycloalkyl, where the cycloalkyl moiety for its part may optionally be mono- or polysubstituted by identical or different substituents from the group consisting of halogen and $C_1$-$C_4$-alkyl
$Z^5$ represents $C_2$-$C_{20}$-alkenyl or $C_2$-$C_{20}$-alkynyl, each of which is optionally mono- or polysubstituted by identical or different substituents from the group consisting of halogen, alkylsulfanyl, alkylsulfinyl, alkylsulfonyl, alkoxy, alkylamino, dialkylamino, halogenoalkylsulfanyl, halogenoalkylsulfinyl, halogenoalkylsulfonyl, halogenoalkoxy, halogenoalkylamino, di(halogenoalkyl)amino, —$SiR^6R^7R^8$ and $C_3$-$C_6$-cycloalkyl, where the cycloalkyl moiety for its part may optionally be mono- or polysubstituted by identical or different substituents from the group consisting of halogen and $C_1$-$C_4$-alkyl,
$R^4$ represents hydrogen or $C_1$-$C_4$-alkyl,
$R^5$ represents hydrogen or $C_1$-$C_4$-alkyl,
m represents 0, 1, 2 or 3,
$R^6$ and $R^7$ independently of one another represent hydrogen, $C_1$-$C_8$-alkyl, $C_1$-$C_8$-alkoxy, $C_1$-$C_4$-alkoxy-$C_1$-$C_4$-alkyl, $C_1$-$C_4$-alkylsulfanyl-$C_1$-$C_4$-alkyl or $C_1$-$C_6$-halogenoalkyl,
$R^8$ represents hydrogen, $C_1$-$C_8$-alkyl, $C_1$-$C_8$-alkoxy, $C_1$-$C_4$-alkoxy-$C_1$-$C_4$-alkyl, $C_1$-$C_4$-alkylsulfanyl-$C_1$-$C_4$-alkyl, $C_2$-$C_8$-alkenyl, $C_2$-$C_8$-alkynyl, $C_1$-$C_6$-halogenoalkyl, $C_2$-$C_6$-halogenoalkenyl, $C_2$-$C_6$-halogenoalkynyl, $C_3$-$C_6$-cycloalkyl, or represents in each case optionally substituted phenyl or phenylalkyl;
$W^1$ represents halogen, cyano, nitro, amino, hydroxyl, formyl, carboxy, carbamoyl, thiocarbamoyl; or
straight-chain or branched alkyl, hydroxyalkyl, oxoalkyl, alkoxy, alkoxyalkyl, alkylsulfanylalkyl, dialkoxyalkyl, alkylsulfanyl, alkylsulfinyl or alkylsulfonyl having in each case 1 to 8 carbon atoms; or straight-chain or branched alkenyl or alkenyloxy having in each case 2 to 6 carbon atoms; or
straight-chain or branched halogenoalkyl, halogenoalkoxy, halogenoalkylsulfanyl, halogenoalkylsulfinyl or halogenoalkylsulfonyl having in each case 1 to 6 carbon atoms and 1 to 13 identical or different halogen atoms; or
straight-chain or branched halogenoalkenyl or halogenoalkenyloxy having in each case 2 to 6 carbon atoms and 1 to 11 identical or different halogen atoms; or
straight-chain or branched alkylamino, dialkylamino, alkylcarbonyl, alkylcarbonyloxy, alkoxycarbonyl, alkylaminocarbonyl, dialkylaminocarbonyl, arylalkylaminocarbonyl, or dialkylaminocarbonyloxy having 1 to 6 carbon atoms in the respective hydrocarbon chains, or alkenylcarbonyl or alkynylcarbonyl, having 2 to 6 carbon atoms in the respective hydrocarbon chains; or cycloalkyl or cycloalkyloxy having in each case 3 to 6 carbon atoms; or doubly attached alkylene having 3 or 4 carbon atoms, oxyalkylene having 2 or 3 carbon atoms or dioxyalkylene having 1 or 2 carbon atoms, each of which radicals is optionally mono- to tetrasubstituted by identical or different substituents from the group consisting of fluorine, chlorine, oxo, methyl, trifluoromethyl and ethyl;
or the groupings —$(CR^4R^5)_m SiR^6R^7R^8$ or —$C(Q^2)$=N-$Q^3$, in which
$Q^2$ represents hydrogen, hydroxyl or alkyl having 1 to 4 carbon atoms, halogenoalkyl having 1 to 4 carbon atoms and 1 to 9 fluorine, chlorine and/or bromine atoms or cycloalkyl having 1 to 6 carbon atoms and
$Q^3$ represents hydroxyl, amino, methylamino, phenyl, benzyl or represents in each case optionally cyano-, hydroxyl-, alkoxy-, alkylsulfanyl-, alkylamino-, dialkylamino- or phenyl-substituted alkyl or alkoxy having 1 to 4 carbon atoms, or represents alkenyloxy or alkynyloxy having in each case 2 to 4 carbon atoms,
and also phenyl, phenoxy, phenylsulfanyl, benzoyl, benzoylethenyl, cinnamoyl, heterocyclyl or phenylalkyl, phenylalkyloxy, phenylalkylsulfanyl or heterocyclylalkyl having in each case 1 to 3 carbon atoms in the respective alkyl moieties, each of which radicals is optionally mono- to trisubstituted in the ring moiety by halogen and/or straight-chain or branched alkyl or alkoxy having 1 to 4 carbon atoms;
$W^2$ represents hydrogen, halogen, cyano, nitro, $C_1$-$C_6$-alkyl, $C_2$-$C_4$-alkenyl, $C_2$-$C_4$-alkynyl, $C_1$-$C_4$-alkoxy, $C_1$-$C_4$-alkylsulfanyl, $C_1$-$C_4$-alkylsulfinyl, $C_1$-$C_4$-alkylsulfonyl, $C_3$-$C_6$-cycloalkyl; represents $C_1$-$C_4$-halogenoalkyl, $C_1$-$C_4$-halogenoalkoxy, $C_1$-$C_4$-halogenoalkylsulfanyl, $C_1$-$C_4$- halogenoalkylsulfinyl, $C_1$-$C_4$-halogenoalkylsulfonyl having in each case 1 to 5 halogen atoms; represents —$SO_2NR^{10}R^{11}$, —C(=Y)$R^{12}$, —Si($R^{13}$)$_3$, $C_2$-$C_4$-alkenylene-Si($R^{13}$)$_3$, $C_2$-$C_4$-alkynylene-Si($R^{13}$)$_3$, —$NR^{15}R^{16}$, —$CH_2$—$NR^{15}R^{16}$, in which Y represents O (oxygen) or S (sulfur), $R^{10}$ represents hydrogen, $C_1$-$C_4$-alkyl or —C(=Y)$R^{12}$, $R^{11}$ represents hydrogen, $C_1$-$C_4$-alkyl or —C(=Y)$R^{12}$, or $R^{10}$ and $R^{11}$ together with the nitrogen atom to which they are attached form a saturated heterocycle which has 5 to 8 ring atoms and is optionally mono- or polysubstituted by identical or different substituents from the group consisting of halogen and $C_1$-$C_4$-alkyl, where the heterocycle may contain 1 or 2 further non-adjacent heteroatoms from the group consisting of oxygen, sulfur and $NR^{14}$, $R^{12}$ represents hydrogen, $C_1$-$C_4$-alkyl, $C_1$-$C_4$-alkoxy or —$NR^{15}R^{16}$, $R^{13}$ represents hydrogen, $C_1$-$C_8$-alkyl, $C_1$-$C_8$-alkoxy, $C_1$-$C_4$-alkoxy-$C_1$-$C_4$-alkyl, $C_1$-$C_4$-alkylsulfanyl-$C_1$-$C_4$-alkyl or $C_1$-$C_6$-halogenoalkyl, where the three radicals $R^{13}$ may in each case be identical or different, $R^{14}$ represents hydrogen or $C_1$-$C_6$-alkyl, $R^{15}$ represents hydrogen or $C_1$-$C_4$-alkyl, $R^{16}$ represents hydrogen or $C_1$-$C_4$-alkyl, or $R^{15}$ and $R^{16}$ together with the nitrogen atom to which they are attached form a saturated heterocycle having 5 to 8 ring atoms which is optionally mono- or polysubstituted by identical or different substituents from the group consisting of halogen and $C_1$-$C_4$-alkyl, where the heterocycle may contain 1 or 2 further non-adjacent heteroatoms from the group consisting of oxygen, sulfur and $NR^{14}$, where, unless indicated otherwise, a group or a substituent which is substituted according to the invention is substituted by one or more group selected from the group consisting of halogen; nitro, cyano, $C_1$-$C_{12}$-alkyl; $C_1$-$C_6$-haloalkyl having 1 to 9 identical or different halogen atoms; $C_1$-$C_6$-alkoxy; $C_1$-$C_6$-haloalkoxy having 1 to 9 identical or different halogen atoms; $C_1$-$C_6$-alkylsulfanyl; $C_1$-$C_6$-haloalkylsulfanyl having 1 to 9 identical or different halogen atoms; $C_1$-$C_6$-alkylsulfonyl; $C_1$-$C_6$-haloalkylsulfonyl having 1 to 9 identical or different halogen atoms; $C_2$-$C_{12}$-alkenyl; $C_2$-$C_{12}$-alkynyl; $C_3$-$C_7$-cycloalkyl; phenyl; tri($C_1$-$C_8$)alkylsilyl; tri($C_1$-$C_8$) alkylsilyl-$C_1$-$C_8$-alkyl.

2. A compound according to claim 1, wherein $X^1$ and $X^2$ independently from each other represents fluorine or chlorine.

3. A compound according to claim 1, wherein
$R^1$ represents a substituted or non-substituted $C_1$-$C_8$-alkyl, a $C_1$-$C_8$-halogenoalkyl having 1 to 5 halogen atoms or a non-substituted $C_3$-$C_7$-cycloalkyl.

4. A compound according to claim 3, wherein $R^1$ represents methyl or cyclopropyl.

5. A compound according to claim 1, wherein
M represents one of the cycles below:

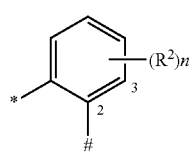
M-1

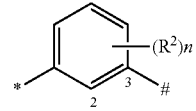
M-2

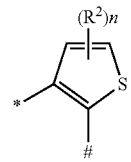
M-3

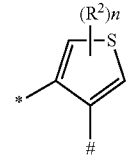
M-4

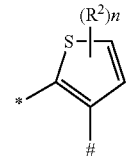
M-5

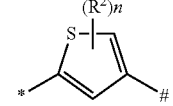
M-6 where the bond marked * is linked to the amide and the bond marked # is linked to the radical Q-Z and
n is 0 or 1.

6. A compound according to claim 5, wherein
M represents M-1 or M-3.

7. A compound according to claim 1, wherein
n is 0 or 1 and
$R^2$ represents fluorine.

8. A compound according to claim 1, wherein
Q represents a direct bond or O (oxygen).

9. A compound according to claim 1, wherein O represents $NR^3$ and
$R^3$ represents hydrogen, $C_1$-$C_6$-alkyl, $C_1$-$C_3$-alkoxy-$C_1$-$C_3$-alkyl, $C_1$-$C_3$-alkylsulfanyl-$C_1$-$C_3$-alkyl or $C_3$-$C_6$-cycloalkyl.

10. A compound according to claim 1, wherein Z represents Z1 which is mono- to pentasubstituted by identical or different substituents W1, wherein
$W^1$ represents fluorine, chlorine, bromine, methyl, ethyl, n- or i-propyl, n-, i-, s- or t-butyl, methoxy, ethoxy, n- or i-propoxy, trifluoromethyl, trifluoroethyl, difluoromethoxy, trifluoromethoxy, difluorochloromethoxy, trifluoroethoxy, in each case doubly attached difluoromethylenedioxy or tetrafluoroethylenedioxy, or the groupings —$CH_2Si(CH_3)_3$, —$Si(CH_3)_3$ or —C($Q^2$)=N-$Q^3$, in which
$Q^2$ represents hydrogen, methyl, ethyl or trifluoromethyl and
$Q^3$ represents hydroxyl, methoxy, ethoxy, propoxy or isopropoxy.

11. A compound according to claim 1, wherein Z represents Z2, wherein
$Z^2$ represents 2-pyridinyl, 3-pyridinyl or 4-pyridinyl, each of which is optionally mono- to trisubstituted by $W^2$, and W² represents hydrogen, fluorine, chlorine, bromine, cyano, nitro, methyl, ethyl, n- or isopropyl, n-, iso-, sec- or tert-butyl, allyl, propargyl, methoxy, ethoxy, n- or isopropoxy, n-, iso-, sec- or tert-butoxy, methylsulfanyl, ethysulfanyl, n- or isopropylsulfanyl, n-, iso-, sec- or tert-butylsulfanyl, methylsulfinyl, ethylsulfinyl, n- or isopropylsulfinyl, n-, iso-, sec- or tert-butylsulfinyl, methylsulfonyl, ethylsulfonyl, n- or iso-propylsulfonyl, n-, iso-, sec- or tert-butylsulfonyl, cyclopropyl, cyclopentyl, cyclohexyl, trifluoromethyl, difluoromethyl, trichloromethyl, trifluoroethyl, trifluoromethoxy, difluoromethoxy, trichloromethoxy, difluoromethylsulfanyl, difluorochloromethylsulfanyl, trifluoromethylsulfanyl, trifluoromethylsulfinyl, trifluoromethylsulfonyl, —SO₂NMe₂, —C(=Y)R¹², —Si(R¹³)₃, —CH=CH—Si(R¹³)₃, —CH₂—CH=CH—Si(R¹³)₃, —CH=CH—CH₂—Si(R¹³)₃, —C≡C—Si(R¹³)₃, —CH₂—C≡C—Si(R¹³)₃, or —C≡C—CH₂—, in which Y represents O (oxygen) or S (sulfur).

12. A compound according to claim 1, wherein Z represents Z3, and

Z³ represents C₃-C₇-cycloalkyl or C₄-C₁₀ bicycloalkyl having in each case 3 to 10 carbon atoms, each of which radicals is optionally mono- to tetrasubstituted by identical or different substituents from the group consisting of halogen, C₁-C₄-alkyl, —CH₂Si(CH₃)₃ and —Si(CH₃)₃.

13. A compound according to claim 12, wherein

Z³ represents chlorine- and methyl-substituted cyclopropyl.

14. A compound according to claim 1, wherein Z represents Z4 and

Z⁴ represents unsubstituted C₁-C₂₀-alkyl or C₁-C₂₀-alkyl which is substituted by fluorine, chlorine, methylsulfanyl, ethylsulfanyl, n- or isopropylsulfanyl, n-, iso-, sec-, tert-butylsulfanyl, pentylsulfanyl, hexylsulfanyl, methylsulfonyl, ethylsulfonyl, n- or isopropylsulfonyl, n-, iso-, sec-, tert-butylsulfonyl, methoxy, ethoxy, n- or isopropoxy, n-, iso-, sec-, tert-butoxy, methylamino, ethylamino, n- or isopropylamino, n-, iso-, sec-, tert-butylamino, dimethylamino, diisopropylamino, trifluoromethylsulfanyl, trifluoromethoxy, —SiR⁶R⁷R⁸, cyclopropyl, dichlorocyclopropyl, cyclobutyl, cyclopentyl or cyclohexyl.

15. A compound according to claim 1, wherein Z represents Z5 and

Z⁵ represents C₂-C₂₀-alkenyl or C₂-C₂₀-alkynyl, each of which is optionally substituted by fluorine, chlorine, bromine, iodine, C₁-C₆-alkylsulfanyl, C₁-C₄-alkylsulfinyl, C₁-C₄-alkylsulfonyl, C₁-C₄-alkoxy, C₁-C₄-alkylamino, di(C₁-C₄-alkyl)amino, C₁-C₄-halogenoalkylsulfanyl, C₁-C₄-halogenoalkylsulfinyl, C₁-C₄-halogenoalkylsulfonyl, C₁-C₄-halogenoalkoxy, C₁-C₄-halogenoalkylamino, di(C₁-C₄-halogenoalkyl)amino having in each case 1 to 9 fluorine, chlorine and/or bromine atoms, —SiR⁶R⁷R⁸, cyclopropyl, dichlorocyclopropyl, cyclobutyl, cyclopentyl or cyclohexyl.

16. A fungicide composition comprising, as an active ingredient, an effective amount of a compound according to claim 1, and an agriculturally acceptable support, carrier and/or filler.

17. A method for controlling phytopathogenic fungi of crops, comprising applying an agronomically effective and substantially non-phytotoxic quantity of a compound according to claim 1, to soil where a plant grows and/or is capable of growing, to leaves and/or fruit of plants and/or to seeds of a plant.

18. A method for controlling phytopathogenic fungi of crops, comprising applying a fungicide composition according to claim 16 to soil where a plant grows and/or is capable of growing, to leaves and/or fruit of a plant and/or to seeds of a plant.

19. A compound according to claim 1, wherein T is oxygen.

20. A compound according to claim 5, wherein M is M-1, M-2, or M-3, T is oxygen, n is zero, and R1 is methyl or ethyl.

* * * * *